(12) United States Patent
Stoit et al.

(10) Patent No.: US 8,252,930 B2
(45) Date of Patent: Aug. 28, 2012

(54) AZAINDOLE DERIVATIVES WITH A COMBINATION OF PARTIAL NICOTINIC ACETYL-CHOLINE RECEPTOR AGONISM AND DOPAMINE REUPTAKE INHIBITION

(75) Inventors: Axel Stoit, Weesp (NL); Hein K. A. C. Coolen, Weesp (NL); Martina A. W. Van Der Neut, Weesp (NL); Cornelis G. Kruse, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 0 days.

(21) Appl. No.: 12/940,271

(22) Filed: Nov. 5, 2010

(65) Prior Publication Data
US 2011/0053962 A1 Mar. 3, 2011

Related U.S. Application Data

(62) Division of application No. 11/773,111, filed on Jul. 3, 2007, now Pat. No. 7,964,728.

(60) Provisional application No. 60/818,507, filed on Jul. 6, 2006.

(51) Int. Cl.
*C07D 471/02* (2006.01)
(52) U.S. Cl. ........................................ 546/113
(58) Field of Classification Search ................... 546/113
See application file for complete search history.

(56) References Cited

U.S. PATENT DOCUMENTS 7,863,288 B2 * 1/2011 Ibrahim et al. ................ 514/300
2001/0053788 A1 12/2001 Lange et al.

FOREIGN PATENT DOCUMENTS

| EP | 0 870 768 A1 | 10/1998 |
| WO | WO 2003/026647 A1 | 4/2003 |
| WO | WO 2003/026648 A1 | 4/2003 |
| WO | WO 2006/017443 A2 | 2/2006 |
| WO | WO 2007/002433 A1 | 1/2007 |

OTHER PUBLICATIONS

West, Solid State Chemistry and Its Applications, John Wiley & Sons, 1984.*
Curtis et al. Bioorganic & Medicinal Chemistry Letters (1999), 9(4),585-588.*
Sinova Inc., Article XP-002449870, Abstract published Jun. 28, 2006, File CHEMCATS, Accession No. 2028292725, Order No. SL-01987, Sinova Product List, published Jun. 28, 2006.
Emad J. Siddiqui et al., Anti Cancer Research, vol. 25, pp. 4281-4286 (2005) "Growth Inhibitory Effect of Doxazosin on Prostate and Bladder Cancer Cells. Is the Serotonin Receptor Pathway Invovled?" pp. 4282-4286.
International Search Report and Written Opinion, dated Sep. 20, 2007, issued in PCT/EP2007/056792.
Database Chemcats [Online] Chemical Abstracts Service, Columbus, Ohio, US; Apr. 7, 2004, XP002465985, Database accession No. 672331-19-0 compound of Registry No. 672331-19-0.
J. Svetlik et al., "Unexpected Ring Closure Reaction of [Alpha], [Beta]-Unsaturated Ketones with Aminoguanidine. Entry into 1,3,5-trisubstituted Pyrazoles," Heterocyclic Chemistry, vol. 39, No. 2, (2002), pp. 363-366, XP002468177.
F. L. Scott et al., "Mechanism of Pyrazoline Formation from the Reactions of Substituted Hydrazines and Mannich Bases," Chemical Society, Section C: Organic Chemistry, Chemical Society. Letchworth, GB, 1971, pp. 80-86, XP009094752.
Database Chemcats [Online], Chemical Abstracts Service, Columbus, Ohio, US; Jun. 11, 1988, XP002468179, Database accession No. 114794-17-1 compound of Registry No. 114794-17-1.
Database Chemcats [Online] Chemical Abstracts Service, Columbus, Ohio, US; Sep. 2, 2003, XP002468180, Database accession No. 577791-34-5 compound of Registry No. 577791-34-5.
Scott et al., "Nitrogen Systems, Part XIV: The Synthesis of 1-Guaynl-Pyrazolines" Chimia, Aarau, Ch, vol. 12, 1958, pp. 148-150, XP009094703.
M. Morales et al., "Coexistence of serotonin 3 (5-HT3) and CB1 cannabinoid receptors in interneurons of hippocampus and dentate gyrus" Hippocampus, vol. 12, No. 6, (2002), pp. 756-764, XP002468178.
International Search Report and Written Opinion, dated Mar. 3, 2008, issued in PCT/EP2007/059944.

* cited by examiner

*Primary Examiner* — Nizal Chandrakumar
(74) *Attorney, Agent, or Firm* — Finnegan, Henderson, Farabow, Garrett & Dunner, LLP

(57) ABSTRACT

Azaindole derivatives of formula (I):

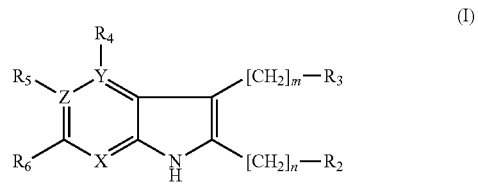

wherein the symbols have the meanings given in the specification, are described. These compounds have a combination of partial nicotinic acetylcholine receptor agonism and dopamine reuptake inhibition. The invention also relates to pharmaceutical compositions containing these compounds, to methods for preparing them, methods for preparing novel intermediates useful for their synthesis, methods for preparing compositions, and uses of such compounds and compositions, for example, their use in administering them to patients to achieve a therapeutic effect in disorders in which nicotinic receptors and/or dopamine transporters are involved, or that can be treated via manipulation of those receptors.

4 Claims, No Drawings

AZAINDOLE DERIVATIVES WITH A COMBINATION OF PARTIAL NICOTINIC ACETYL-CHOLINE RECEPTOR AGONISM AND DOPAMINE REUPTAKE INHIBITION

This is a divisional of U.S. application Ser. No. 11/773,111, filed Jul. 3, 2007 now U.S. Pat. No. 7,964,728, and claims the benefit of U.S. Provisional Application No. 60/818,507, filed Jul. 6, 2006, the content of each of which is incorporated herein by reference.

| CONTENTS | page |
|---|---|
| Title of the invention | 1 |
| Contents | 1 |
| Description of the invention | 9 |
| Definitions of chemical and other terms | 15 |
| Abbreviations | 20 |
| Examples | 23 |
| Example 1: Analytical methods | 23 |
| Example 2: General aspects of syntheses | 25 |
| Example 3: Syntheses of compounds of the invention | 40 |
| Example 4: Syntheses of compounds of EP 1 178 045 | 83 |
| Example 5: Pharmacological methods | 84 |
| Example 6: Pharmacological test results | 87 |
| Example 7: Pharmaceutical preparations | 88 |
| References, cited patents and patent applications | 92 |
| Claims | 95 |

Nicotine has been proposed to have a number of pharmacological effects (Pullan, 1994) (See the list of references on pages 95-97 of this application for full citations). Certain of those effects can be related to effects upon neurotransmitter release. Release of acetylcholine, dopamine, norepinephrine, serotonin and glutamate upon administration of nicotine has been reported (Toth, 1992). Confirmatory reports and additional recent studies have included the modulation in the CNS of glutamate, nitric oxide, GABA, takykinins, cytokines and peptides (Brioni, 1997). Furthermore, neuroprotective and various other beneficial pharmacological effects of nicotine have been proposed (Sjak-shie, 1993; Onaivi, 1994).

Various compounds that target nAChRs have been reported as being useful for treating a wide variety of conditions and disorders (Damaj, 1999; Bannon, 1998; Bencherif, 2002; Levin, 2002; O'Neill, 2002; Breining, 2005). Therapeutic indications discussed in the literature cited above include: CNS disorders such as neuroendocrine, neurological and neuropsychiatric disorders, schizophrenia, memory and learning disabilities, attention deficit hyperactivity disorder, anxiety disorders, depressive disorders, neurodegenerative disorders, Alzheimer's disease, addiction disorders, nicotine addiction, cocaine addiction, amphetamine addiction, eating disorders pain, inflammatory processes, convulsive disorders, ocular disorders, glaucoma, macular degeneration, diabetic retinopathy, cardiovascular and gastrointestinal disorders and cancer.

Nicotinic receptor antagonists have good potential as therapeutic agents, since they offer another means of modulating nicotinic receptor function. Nicotinic agonists rapidly desensitize these receptors, essentially inhibiting their function. Thus, inhibition of nicotinic receptor function may be the action, which confers clinical utility, indicating that nicotinic receptor antagonists could also be beneficial in the treatment of diseases for which nicotinic agonists are currently being developed. For example, schizophrenia and drug abuse have both been associated with hyperactivity of CNS dopaminergic systems, and inhibition of nicotinic receptors may be advantageous in reducing such hyperactivity.

CNS disorders, a type of neurological disorders, can be drug induced, can be attributed to genetic predisposition, infection or trauma, or can be of unknown etiology. They comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of acetylcholine, dopamine, norepinephrine and/or serotonin.

Relatively common CNS disorders include pre-senile dementia (early-onset Alzheimer's disease), senile dementia (dementia of the Alzheimer's type), micro-infarct dementia, AIDS-related dementia, vascular dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, epilepsy, mania, attention deficit disorder, anxiety, dyslexia, schizophrenia, depression, obsessive-compulsive disorders and Tourette's syndrome.

The action of many neuropharmacologically therapeutic agents involves the modulation of dopamine, norepinephrine and serotonin release, uptake and storage within its respective terminals in the CNS. Most neurotransmitters are stored in synaptic vesicles, which are prominent features of nerve terminals. Concentration into vesicles appears to be responsible for maintaining a ready supply of neurotransmitter available for neuronal exocytotic release into the synaptic cleft. Vesicles also serve the role of protecting the neurotransmitter from metabolic breakdown. One transport site on the vesicle membrane is the vesicular monoamine transporter-2 (VMAT2), whose role is to transport transmitter from the cytosol into the synaptic vesicle. Dihydrotetrabenazine, structurally related to methoxytetrabenazine, has been used as a radiolabel to probe the interaction of drugs with VMAT2. Both compounds act at the same site on VMAT2. Once the neurotransmitter is released from the terminal into the synaptic space, it interacts with postsynaptic receptors and subsequently is taken back up into the terminal via the plasma membrane transporter (e.g., the dopamine transporter and/or the serotonin transporter). Thus, transporter proteins modify the concentration of neurotransmitter in the cytosolic and vesicular storage pools, thereby having the ability to alter subsequent neurotransmission. Dopamine is a monoamine neurotransmitter that plays a critical role in the function of the hypothalamic-pituitary-adrenal axis and in the integration of information in sensory, limbic, and motor systems. The primary mechanism for termination of dopamine neurotransmission is through reuptake of released dopamine by $Na^+/Cl^-$ dependent plasma membrane transporters. Depending on the surrounding ionic conditions, the dopamine transporter can function as a mediator of both inward directed dopamine transport (i.e., "reuptake") and outward directed dopamine transport (Le., "release"). The functional significance of the dopamine transporter is its regulation of dopamine neurotransmission by terminating the action of dopamine in a synapse via reuptake.

Dopaminergic reward pathways have been implicated in disorders resulting from addictive behaviors. Variants of the dopamine $D_2$ receptor gene have been associated with alcoholism, obesity, pathological gambling, attention deficit hyperactivity disorder, Tourette syndrome, cocaine dependence, nicotine dependence, polysubstance abuse, and other drug dependency. Since reduced dopaminergic functions have been found in individuals with a minor A1 allele of the dopamine $D_2$ receptor, it has been suggested that the dopamine $D_2$ receptor may be a reinforcement or reward gene. Furthermore, several studies suggest that an associate of dopamine $D_2$ receptor gene polymorphisms are associated with impulsive-addictive-compulsive behavior, i.e., "Reward Deficiency Syndrome" (Blum, 1995).

The dopamine transporter is a presynaptically located macromolecule which plays an important role in pathophysiocological processes in the CNS. The dopamine transporter terminates dopaminergic neurotransmission by reaccumulation of released dopamine into presynaptic neurons. In cocaine addiction, binding of cocaine to the dopamine transporter and consequent blockage of dopamine uptake appears to be related to the reinforcing properties of the drug. Also associated with the transport function is concentration of neurotoxic chemicals in dopaminergic neurons which is implicated in Parkinson's disease. The transporter macromolecule may be a marker for Parkinson's, as evidenced by its absence in tissue sections of Parkinson's diseased putamen. The dopamine transporter further plays a crucial role in the neurotoxic action of 1-methyl-4-phenyl-1,2,3,6-tetrahydropyridine (MPTP) which induces idiopathic Parkinson's syndrome in humans. Consequently, potent yet selective ligands for the dopamine transporter have potential for in vivo monitoring of primary targets of cocaine in the brain, for characterization of cocaine binding sites, for pharmacotherapeutic agents for treatment of cocaine addition, and for monitoring of Parkinson's disease.

Many drugs can cause physical and/or psychological addiction. Those most well known drugs include opiates, such as heroin, opium and morphine; sympathomimetics, including cocaine and amphetamines; sedative-hypnotics, including alcohol, benzodiazepines and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change motivates the addicted individual to continue consuming the drug despite serious social, legal, physical and/or professional consequences. Cocaine addiction remains one of the major health problems in the United States. Fundamental studies from many laboratories have shown that cocaine blocks the uptake of dopamine from the synaptic cleft of the dopamine transporter.

Nomifensine and bupropion are two compounds used as pharmacological standards for dopamine transporter inhibitors. Both are used clinically as antidepressants, and bupropion is also one of the few compounds used in the therapy of nicotine addiction. The "GBR" class of compounds is known for its unusually high selectivity and potency for the dopamine transporter. Two of these compounds have affinities in the low nanomolar range (DeVries, 1997).

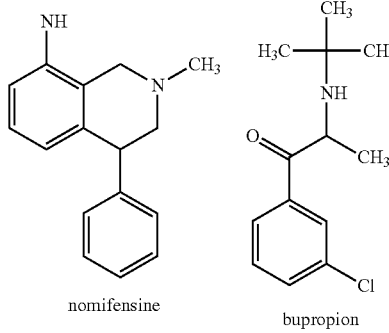

nomifensine bupropion vanoxerine (GBR 12909)

Radiolabeling of these compounds has facilitated elucidation of neuropharmacological activity. GBR 12909 (vanoxerine) dissociates very slowly from the DAT, and attenuates increase in extracellular dopamine levels induced by cocaine as measured by microdialysis. This compound was non-stimulatory in human volunteers, and has been shown to block cocaine self-administration behavior in the rhesus monkey (Dutta, 1993). Such studies raise the possibility that suitable compounds may serve as cocaine antagonists without being themselves addictive.

One of the effects of nicotine is release of dopamine. Inhibitors of the dopamine transporter have essentially the same effect, albeit by a completely different mechanism of action. Thus, in conditions in which elevation of endogenous dopamine levels would be required or desired, chances that a compound which has a dual mechanism of action will be efficacious, are higher than that of compounds having a single mode of action only. Compounds with such a dual mode of action are known. The first identified as such was—as so often in the history of modern medicine—a natural product.

α-Lobeline (lobeline), a lipophilic nonpyridino, alkaloidal constituent of Indian tobacco, is a major alkaloid in a family of structurally-related compounds found in *Lobelia inflata*. Lobeline has been reported to have many nicotine like effects, including tachycardia and hypertension, hyperalgesia and improvement of learning and memory. Lobeline has a high affinity for nicotinic receptors, but no obvious structural resemblance of lobeline to nicotine is apparent and structure function relationships between S(−)-nicotine and lobeline do not suggest a common pharmacophore. Also, differential effects of lobeline and nicotine suggest that these drugs may not be active through a common CNS mechanism, even though lobeline has been considered a mixed nicotinic agonist/antagonist.

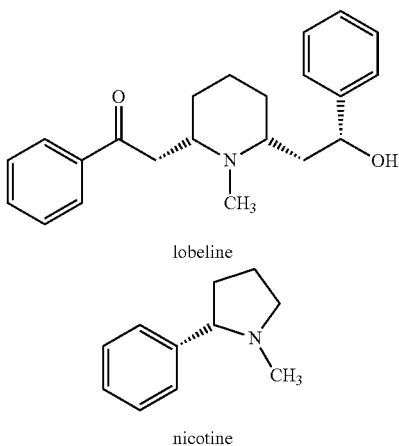

lobeline nicotine

Lobeline evokes dopamine release from rat striatal slices. However, lobeline evoked dopamine release is neither dependent upon extracellular calcium nor is it sensitive to mecamylamine, a noncompetitive nicotinic receptor antagonist. Thus, lobeline evoked dopamine release occurs via a different mechanism than does nicotine to evoke dopamine release. In this respect, lobeline also inhibits dopamine uptake into rat striatal synaptic vesicles via an interaction with the dihydrotetrabenazine site on the VMAT2, thus increasing the cytosolic dopamine available for reverse transport by the plasma membrane transporter (DAT) (Teng, 1997, 1998). Thus, lobeline interacts with nicotinic receptors and blocks nicotine-evoked dopamine release, but also interacts with dopamine transporter proteins (DAT and VMAT2) to modify the concentration of dopamine in the cytosolic and vesicular storage pools, thereby altering subsequent dopaminergic neurotransmission.

U.S. Publication No. 2003/0100547 and U.S. Publication No. 2004/0266824 disclose a series of 2,6-disubstituted piperidine and piperazine derivatives, which are structural analogs of lobeline:

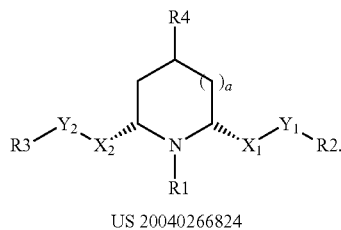

US 20040266824

The compounds were synthesized and tested for activity in the nicotinic receptor assays, and dopamine transporter and release assays, to assess the interaction of these compounds with these specific proteins on the presynaptic terminal of monoaminergic neurons in the CNS. Some of these compounds have greater selectivity for interaction with DAT than for interaction with nicotinic receptors, whereas other compounds interact with both nicotinic receptors and DAT, more similar to lobeline. Other compounds were more selective for the nicotinic receptor than for DAT. These combinations of pharmacological activity are considered to be beneficial for the treatment of psychostimulant abuse and withdrawal, eating disorders, and central nervous system diseases and pathologies.

Azaindole-ethylamine derivatives as nicotinic acetylcholine receptor binding agents, useful in treatment of conditions associated with depletion of nicotine receptors in mammals, notably nicotine addiction, are disclosed in EP 0 870 768 A1 and EP 1 178 045 A1. Some of the compounds disclosed are structurally related to the compounds of the present invention. They are potent displacers of [$^3$H]-nicotine, with $IC_{50}$-values of less than 2 μM, thus $pIC_{50}$-values of 5.7 or higher. No affinities of specific individual compounds were disclosed. The applications quoted above are silent about dopamine reuptake inhibition. Rightfully so, based on synthesis and testing of a number of compounds claimed in the above applications, it was revealed that they are devoid of activity as inhibitors of dopamine reuptake inhibition.

One goal of the invention was to provide further compounds with a dual mechanism of action: (partial) agonism on nicotinic acetylcholine receptors and inhibition of dopamine reuptake.

DESCRIPTION OF THE INVENTION

The present invention relates to a compound of formula (I):

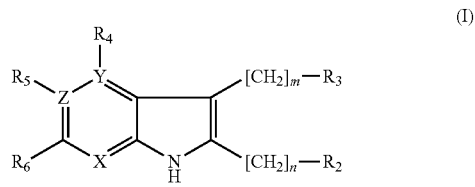

or a tautomer, stereoisomer, or N-oxide thereof, or a pharmacologically acceptable salt, hydrate or solvate of any of the foregoing,
wherein
X, Y and Z, which are the same or different, are chosen from N and C, with the proviso that at least one, and no more than two of X, Y, and Z is an N-atom;
m and n, which are the same or different, are chosen from 0 (zero) and 1, with the proviso that when Y and Z are carbon and X r is nitrogen, m is 0 (zero);
$R_2$ and $R_3$, which are the same or different, are chosen from a hydrogen atom, a halogen atom, a ($C_{1-3}$)alkyl group, a ($C_{1-3}$)alkynyl group, a NH($C_{1-3}$)alkyl group, a $CF_3$ group, a hydroxyl group, a ($C_{1-3}$)alkyloxy group, a piperidinyl group, a pyrrolidinyl group, a tetrahydropyridinyl group, a morpholinyl group, a azepanyl group, a 1-aza-bicyclo[2.2.2]octanyl group and a 1-aza-bicyclo[2.2.2]oct-2-enyl group, which group is either unsubstituted or substituted with at least one substituent chosen from a halogen atom, a ($C_{1-3}$)alkyl group, a phenyl group and a benzyl group; and
$R_4$, $R_5$ and $R_6$, which are the same or different, are chosen from a hydrogen atom, a halogen atom, a ($C_{1-3}$)alkyl group, a ($C_{2-3}$)alkynyl group, a $CF_3$ group, a NH($C_{1-3}$)alkyl group, a hydroxyl group and a ($C_{1-3}$)alkyloxy group, with the proviso that $R_4$ is only present when Y is carbon, and $R_5$ is only present when Z is carbon.

Surprisingly it was found that a compound of formula (I) or a tautomer, stereoisomer or N-oxide thereof, as well as a pharmacologically acceptable salt, hydrate or solvate of said compounds of formula (I) and its tautomers, stereoisomers and N-oxides, are new and have a combination of partial nicotinic acetylcholine receptor agonism and dopamine reuptake inhibition.

In one embodiment, the present invention relates to a compound of formula (I) in which $R_2$ and $R_3$, which are the same or different, are chosen from a hydrogen atom, a piperidinyl group, a pyrrolidinyl group, a tetrahydropyridinyl group, a morpholinyl group, a azepanyl group, a 1-aza-bicyclo[2.2.2] octanyl group and a 1-aza-bicyclo[2.2.2]oct-2-enyl group, which group is either unsubstituted or substituted with at least one substituent chosen from a halogen atom, a ($C_{1-3}$)alkyl group, a phenyl group and a benzyl group; $R_4$, $R_5$ and $R_6$, which are the same or different, are chosen from a hydrogen atom, a halogen atom, a ($C_{1-3}$)alkyl group, and a alkyl($C_{1-3}$) oxy group, with the proviso that $R_4$ is only present when Y is carbon, and that $R_5$ is only present when Z is carbon, and X, Y, Z, m and n have the meanings as given above.

The compounds of the invention of formula (I), as well as the pharmacologically acceptable salts thereof, have (partial) agonistic activity on nicotinic acetylcholine receptors and inhibit dopamine reuptake. They are useful in treating disorders involving abovementioned receptors, or treatable by manipulation of those receptors. For instance neuroendocrine, neurological and neuropsychiatric disorders, schizophrenia, memory and learning disabilities, attention deficit hyperactivity disorder, anxiety disorders, depressive disorders, neurodegenerative disorders, Alzheimer's disease, addiction disorders, nicotine addiction, cocaine addiction, amphetamine addiction, eating disorders pain, inflammatory processes, convulsive disorders, ocular disorders, glaucoma, macular degeneration, diabetic retinopathy, cardiovascular and gastrointestinal disorders and cancer.

Other embodiments of the present invention include, but are not limited to:

pharmaceutical compositions for treating, for example, a disorder or condition treatable by activating and/or blocking the receptors mentioned above, the composition comprising a compound of formula (I) or a pharmaceutically acceptable salt thereof, and a pharmaceutically acceptable carrier;

methods for treating a disorder or condition treatable by activating and/or blocking abovementioned receptors, the method comprising administering to a mammal in need of such treating a compound of formula (I) or a pharmaceutically acceptable salt thereof;

pharmaceutical compositions for treating, for example, a disorder or condition chosen from neuroendocrine, neurological and neuropsychiatric disorders, schizophrenia, memory and learning disabilities, attention deficit hyperactivity disorder, anxiety disorders, depressive disorders, neurodegenerative disorders, Alzheimer's disease, addiction disorders, nicotine addiction, cocaine addiction, amphetamine addiction, eating disorders pain, inflammatory processes, convulsive disorders, ocular disorders, glaucoma, macular degeneration, diabetic retinopathy, cardiovascular and gastrointestinal disorders and cancer;

methods for treating a disorder or condition chosen from the disorders listed above, the methods comprising administering to a mammal in need of such treating a compound of formula (I) or a pharmaceutically acceptable salt thereof;

pharmaceutical compositions for treating a disorder or condition chosen from the disorders listed above, the compositions comprising a compound of formula (I) or a pharmaceutically acceptable salt thereof, and a pharmaceutically acceptable carrier;

methods for treating a disorder or condition chosen from the conditions and disorders listed above, the methods comprising administering to a patient in need of such treating a compound of formula (I) or a pharmaceutically acceptable salt thereof; and methods of activating a nicotine receptor and/or inhibiting dopamine uptake that comprise administering to a subject in need thereof, an effective amount of a compound of formula (I).

Yet another embodiment of the invention comprises the use of a compound or salt according to formula (I) for the manufacture of a medicament. Still another embodiment of the invention relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for treating one or more of the conditions listed above. Such other therapeutic agent(s) may be administered prior to, simultaneously with, or following the administration of the compounds of the invention. The invention also provides compounds, pharmaceutical compositions, kits and methods for treating a disorder or condition chosen from the disorders and conditions listed above, the method comprising administering to a patient in need of such treating a compound of formula (I) or a pharmaceutically acceptable salt thereof.

The compounds of the invention possess (partial) agonistic activity on nicotinic acetylcholine receptors and inhibit dopamine reuptake. These activities are readily demonstrated, for example, using the assays described herein or known in the art.

The invention also provides methods of preparing the compounds of the invention and the intermediates used in those methods.

The compounds of the present invention may contain at least one asymmetric center and can thus occur, for example, as racemates and racemic mixtures, single enantiomers, diastereomeric mixtures and individual diastereomers. Depending on the nature of the various substituents, the molecule can have additional asymmetric centers. Each such asymmetric center will independently produce two optical isomers. All of the possible optical isomers and diastereomers, in mixtures and as pure or partially purified compounds, belong to this invention. The present invention comprises all such isomeric forms of these compounds. Formula (I) shows the structure of the class of compounds without any required stereochemistry. The independent syntheses of these diastereomers, or their chromatographic separations, may be achieved as known in the art by appropriate modification of the methodology disclosed therein. Their absolute stereochemistry may be determined by the X-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The coupling often consists of the formation of salts using an enantiomerically pure acid or base, for example (−)-di-p-toluoyl-D-tartaric acid and/or (+)-di-p-toluoyl-L-tartaric acid. The diasteromeric derivatives may then be converted to the pure enantiomers by cleavage of the added chiral residue. The racemic mixture of the compounds can also be separated directly by chromatographic methods utilizing chiral stationary phases: Methods well-known in the art. Alternatively, any enantiomer of a compound may be obtained by stereoselective synthesis using optically pure starting materials or reagents of known configuration by methods well-known in the art.

In one embodiment, the present invention relates to a tautomer of the compound of formula (I), or a pharmaceutically acceptable salt thereof.

In another embodiment, the present invention relates to a compound of formula (I) in any of its crystalline forms, for example, the compound may exist as a polymorph. In yet another embodiment, the compound of formula (I) may form solvates with water (i.e., hydrates), or common organic solvents.

In still another embodiment, the present invention relates to an isotopically-labeled compound of formula (I) or pharmaceutically acceptable salts thereof, including compounds of formula (I) isotopically-labeled to be detectable by PET or SPECT; this includes compounds of formula (I) labeled with

[$^{13}$C]—, [$^{14}$C]—, [$^{3}$H]—, [$^{18}$F]—, [$^{125}$I]— or other isotopically enriched atoms, suitable for receptor binding or metabolism studies.

Definitions of Chemical and Other Terms

The term 'alkyl' refers to straight or branched saturated hydrocarbon radicals. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, 2-butyl, isobutyl or 2-methyl-n-propyl'. The term 'alkenyl' denotes straight or branched hydrocarbon radicals having one or more carbon-carbon double bonds, such as vinyl, allyl, butenyl, etc., and, for example, ($C_{2-4}$)alkenyl. In 'alkynyl' groups the straight or branched hydrocarbon radicals have one or more carbon-carbon triple bonds, such as ethynyl, propargyl, 1-butynyl, 2-butynyl, etc., and, for example, ($C_{2-4}$)alkynyl. The term 'acyl' means alkyl($C_{1-3}$) carbonyl, arylcarbonyl or aryl-alkyl ($C_{1-3}$)carbonyl.

'Halo' or 'Halogen' means chloro, fluoro, bromo or iodo; 'hetero' as in 'heteroalkyl, heteroaromatic' etc. means containing one or more N, O or S atoms. 'heteroalkyl' includes alkyl groups with heteroatoms in any position, thus including N-bound O-bound or S-bound alkyl groups. The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

As used herein, unless otherwise noted, the term "leaving group" shall mean a charged or uncharged atom or group that departs during a substitution or displacement reaction. Suitable examples include, but are not limited to, Br, Cl, I, mesylate, tosylate, and the like.

N-oxides of the compounds mentioned above are within the scope of the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

With reference to substituents, the term "independently" means that when more than one of such substituents are possible, they may be the same or different from each other. To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Throughout the description and the claims of this specification the word "comprise" and variations of the word, such as "comprising" and "comprises" is not intended to exclude other additives, components, integers or steps.

Any compound metabolized in vivo to provide the bioactive agent (i.e., the compound of formula (I)) is a prodrug within the scope and spirit of the application. Prodrugs are therapeutic agents, inactive per se but transformed into one or more active metabolites. Thus, in the methods of treatment of the present invention, the term "administering" shall encompass treating the various disorders described with the compound specifically disclosed, or with a compound that is not specifically disclosed, but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism and targeting limitations (Bundgaard, 1985; King, 1994; Stella, 2004; Ettmayer, 2004; Järvinen, 2005). Prodrugs, i.e., compounds that when administered to humans by any known route, are metabolized to compounds having formula (I), are within the scope of the invention. In particular this relates to compounds with primary or secondary amino or hydroxy groups. Such compounds can be reacted with organic acids to yield compounds having formula (I) wherein an additional group is present that is easily removed after administration, for instance, but not limited to amidine, enamine, a Mannich base, a hydroxylmethylene derivative, an O-(acyloxymethylene carbamate) derivative, carbamate, ester, amide or enaminone.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Dose. The affinity of the compounds of the invention for nicotine receptors and dopamine uptake sites was determined as described below. From the binding affinity measured for a given compound of formula (I), one can estimate a theoretical lowest effective dose. At a concentration of the compound equal to twice the measured $K_i$-value, nearly 100% of the receptors likely will be occupied by the compound. By converting that concentration to mg of compound per kg of patient one obtains a theoretical lowest effective dose, assuming ideal bioavailability. Pharmacokinetic, pharmacodynamic, and other considerations may alter the dose actually administered to a higher or lower value. The dose of the compound to be administered will depend on the relevant indication, the age, weight and sex of the patient and may be determined by a physician. One example of a dose is a dosage in the range of from 0.01 mg/kg to 10 mg/kg. The typical daily dose of the active ingredients varies within a wide range and will depend on various factors such as the relevant indication, the route of administration, the age, weight and sex of the patient and may be determined by a physician. In general, oral and parenteral dosages will be in the range of 0.1 to 1,000 mg per day of total active ingredients.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids.

The term "treatment" as used herein refers to any treatment of a mammalian, for example, a human condition or disease, and includes: (1) inhibiting the disease or condition, i.e., arresting its development, (2) relieving the disease or condition, i.e., causing the condition to regress, or (3) stopping the symptoms of the disease.

As used herein, the term "medical therapy" intendeds to include prophylactic, diagnostic and therapeutic regimens carried out in vivo or ex vivo on humans or other mammals.

The term "subject" as used herein, refers to an animal, for example, a mammal, such as a human, who has been the object of treatment, observation or experiment.

| ABBREVIATIONS | |
|---|---|
| APT | attached proton test |
| 9-BBN | 9-borobicyclo[3.3.1]nonane |
| BOC | tert-butoxycarbonyl |
| n-BuLi | n-butyl lithium |
| CNS | central nervous system |
| CUR | curtain gas |
| DA | dopamine |
| DAT | dopamine transporter |
| DCM | dichloromethane |
| DF | deflector voltage |
| DHBE | dihydro-β-erythroidne |
| DMAP | 4-dimethylaminopyridin |
| DMC | 2-chloro-1,3-dimethylimidazolinium chloride |
| DME | 1,2-dimethoxyethane |
| DMF | N,N'-dimethylformamide |
| DMG | directed metalation group |
| DMSO | dimethylsulfoxide |
| DOM | directed ortho methylation |
| EP | entrance potential |
| EtOAc | ethylacetate |

| ABBREVIATIONS | |
|---|---|
| EtOH | ethanol |
| FAB | fast atom bombardment |
| FP | focusing potential |
| g | gram(s) |
| h | hour(s) |
| HMDS | hexamethyldisilazane |
| HPLC | high performance liquid chromatography |
| IS | ionspray voltage |
| LDA | lithium diisopropylamide |
| mCIPBA | metachloroperbenzoic acid |
| MeI | methyl iodide |
| MeOH | methanol |
| mg | milligram(s) |
| min | minute(s) |
| ml | milliliter(s) |
| m.p. | melting point c.q. melting range |
| MS | mass spectrometry |
| NaOEt | sodium ethoxide |
| NaOMe | sodium methoxide |
| NBS | N-bromosuccinimide |
| NEB | nebulizer gas |
| PE | petroleum ether (40-60) |
| PET | positron emission tomography |
| QTOF | Quadrupole Time-of-flight |
| $R_f$ | retention factor (thin layer chromatography) |
| $R_t$ | retention time (LC/MS) |
| SEMCl | 2-(trimethylsilyl)ethoxymethylchloride |
| SPECT | single photon emission computed tomography |
| TBAF | tetrabutylammonium fluoride |
| TEA | triethylamine |
| TEM | temperature |
| THF | tetrahydrofuran |
| TIPS | triisopropylsilyl |
| TIPSCl | triisopropylchlorosilane |
| TMEDA | tetramethylethylenediamine |
| TMSA | ethynyl-trimethylsilane |
| VMAT2 | vesicular monoamine transporter-2 |

EXAMPLES

Example 1

Analytical Methods

Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H; 125.7 MHz for $^{13}$C; 50.7 Mhz, 470.4 MHz for $^{19}$F) using a 5 mm SW probe. The spectra were determined in deuterated chloroform or dichloromethane obtained from Cambridge Isotope Laboratories Ltd. Chemical shifts (δ) are given in ppm downfield from tetramethylsilane (1H, 13C) or CCl3F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiple). NH and OH signals were identified after mixing the sample with a drop of $D_2O$.

Flash chromatography refers to purification using the indicated eluent and silica gel (either Acros: 0.030-0.075 mm or Merck silica gel 60: 0.040-0.063 mm).

Column chromatography was performed using silica gel 60 (0.063-0.200 mm, Merck).

Melting points were recorded on a Büchi B-545 melting point apparatus.

Mass spectra were recorded on a Micromass QTOF-2 instrument with MassLynx application software for acquisition and reconstruction of the data. Exact mass measurement was done of the quasimolecular ion [M+H]+. Accurate mass measurements were performed using a JEOL JMS-SX/SX 102 A Tandem Mass Spectrometer using Fast Atom Bombardement. A resolving power of 10,000 (10% valley definition) for high resolution FAB mass spectrometry was used.

All reactions involving moisture sensitive compounds or conditions were carried out under an anhydrous nitrogen atmosphere.

Reactions were monitored by using thin-layer chromatography (TLC) on silica coated plastic sheets (Merck precoated silica gel 60 F254) with the indicated eluent. Spots were visualised by UV light (254 nm) or $I_2$.

Extinction coefficients were determined with a HP 8453 UV-Vis spectrophotometer.

Analytical HPLC was performed on a C18 column (Inertsil ODS-3, particle size 3 mm; 4.6 mm 50 mm) using the following elution gradient: linear gradient of 5% to 95% aqueous $CH_3CN$ containing 0.04% $HCO_2H$ over 5 min, then 95% aqueous $CH_3CN$ containing 0.04% $HCO_2H$ for 2 min at 2.0 ml min$^{-1}$. Products were detected at λ=254 nm.

Liquid Chromatography-Mass Spectrometrry (LC-MS)

The LC-MS system consisted of 2 Perkin Omer series 200 micro pumps. The pumps were connected to each other by a 50 μl tee mixer, and connected to a Gilson 215 auto sampler. The following method was used:

| step | total time | flow (μl/min) | A (%) | B (%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH$_4$HCOO pH = +/−3
B = 100% ACN with 0.025% HCOOH The auto sampler that was used had a 2 μl injection loop. The auto sampler was connected to a Waters Atlantis C18 30*4.6 mm column with 3 μm particles. The column was thermo stated in a Perkin Elmer series 200 column oven at 40° C. The column was connected to a Perkin Elmer series 200 UV meter with a 2.7 μl flowcel. The wavelength was set to 254 nm. The UV meter was connected to a Sciex API 150EX mass spectrometer. The mass spectrometer that was used had the following parameters:

Scanrange: 150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10. The light scattering detector was connected to the Sciex API 150. The light scattering detector that was used was a Sedere Sedex 55 operating at 50° C. and 3 bar $N_2$. The complete system was controlled by a G3 powermac.

Example 2

General Aspects of Synthesis

Compounds of the general formula (I) were prepared from readily available starting materials. Substituted 1H-pyrrolo-[2,3-b]pyridines are available from commercial sources or are known in the chemical literature. (*Synthesis*, 1992; *Heterocycles*, 1999; US 2002/0061892; *Current Organic Chemistry*, 2001).

In one example of a general procedure (scheme 1) that was used to prepare a compound of formula (I), 1H-pyrrolo-[2,3-b]pyridine (7-azaindole (1)) was reacted with 1-benzyl-piperidin-3-one (2) in the presence of a base to produce the piperidin-3-ol compound 3 and not the benzyl analog of compound 5. (*Bioorganic & Medicinal Chemistry Letters*, 2002). The benzyl group was removed using well known methods. For example, in Scheme 1, ammonium formate and palladium hydroxide in methanol were used to produce compound 4, which was dehydrated (5) and reduced to give the desired 3-piperidin-3-yl-1H-pyrrolo[2,3-b]-pyridine (6).

Some specific compounds of structure 7 were formed using the procedure illustrated in scheme 1, starting from (4, 5 or 6) substituted 1H-pyrrolo-[2,3-b]pyridine. In specific examples, R was chosen from lower alkyl, alkyloxy and fluorine.

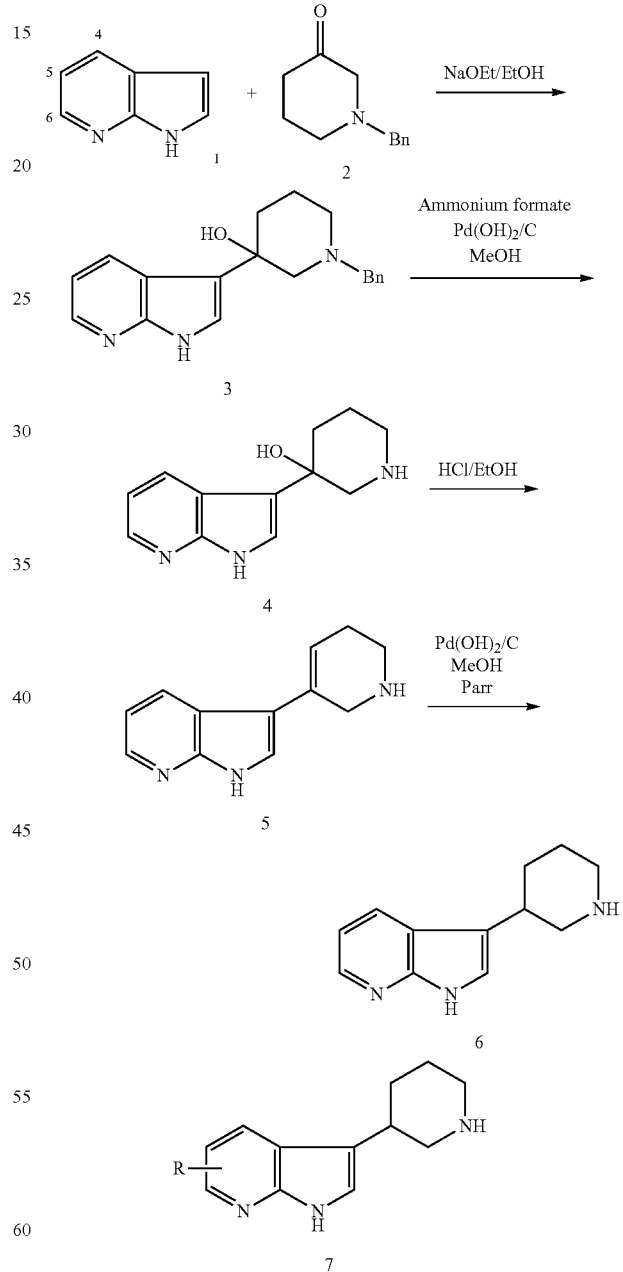

Scheme 1

Scheme 2 illustrates an alternate method of preparing compounds of structure 7. Specifically, the syntheses of 6-chloro-3-piperidin-3-yl-1H-pyrrolo-[2,3-b]pyridine (13). In Scheme 2, compound 6 was reacted with di-t-butyl-dicarbonate to form compound 9 in a two step sequence. Greene (1999) provides more information on addition and subsequent removal of protective groups in organic synthesis.

Selective chlorination of the 7-azaindole analog 9 at the 6-position was achieved by Reissert-Henze type reaction (through the N-oxide 10A) according to a known method (*Synthesis*, 1992).

The $N_1$-methoxycarbonyl compound 11, obtained from this reaction, was converted under basic conditions to compound 12. Then, the N-t-Boc group was removed, which produced compound 13.

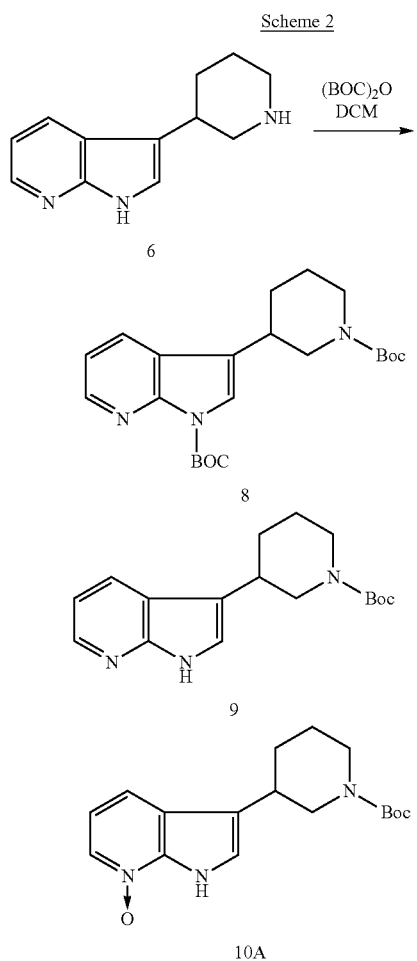

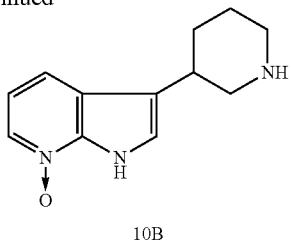

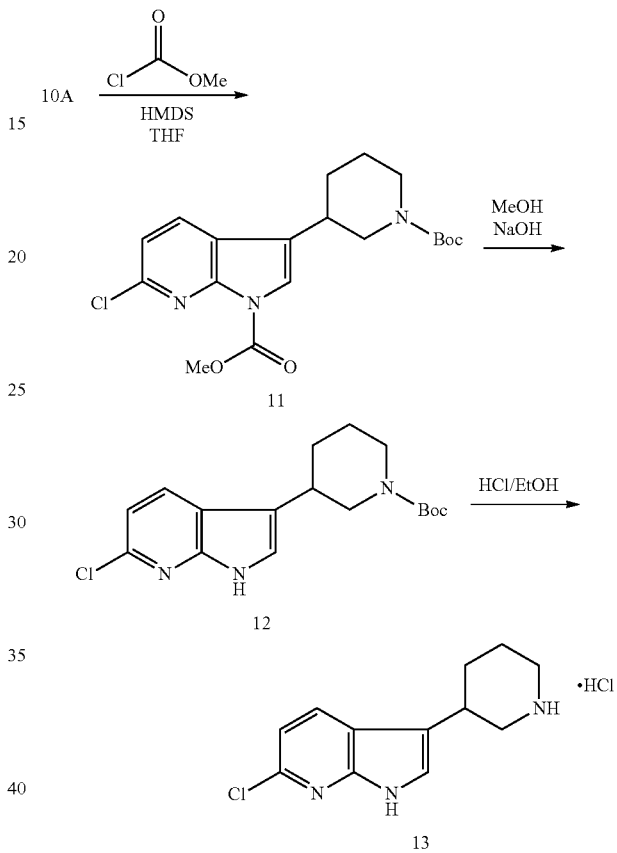

In yet another example of a general procedure for synthesizing compounds of formula (I) (scheme 3), 7-azaindole (1) was reacted with 1-aza-bicyclo[2,2,2]octan-3-one (14) to produce the dehydrated product 15; the dehydrated product 15 was reduced to yield the desired 3-(1H-pyrrolo[2,3-b]pyridine-3-yl)-1-aza-bicyclo[2,2,2]-octane (16).

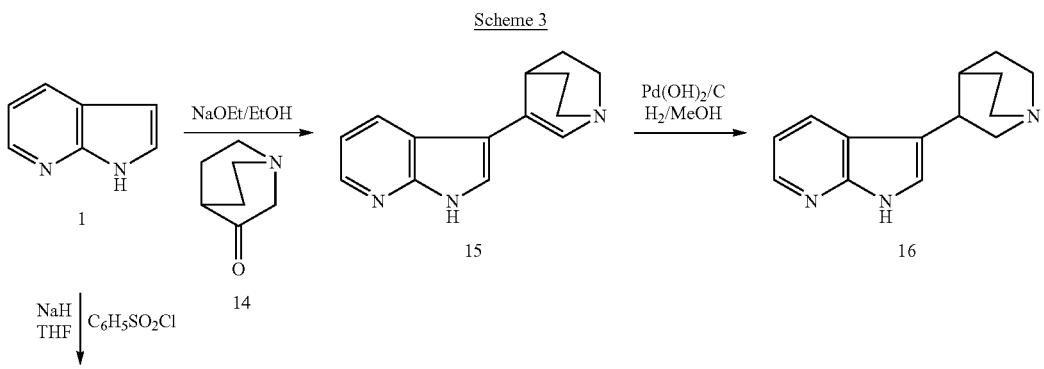

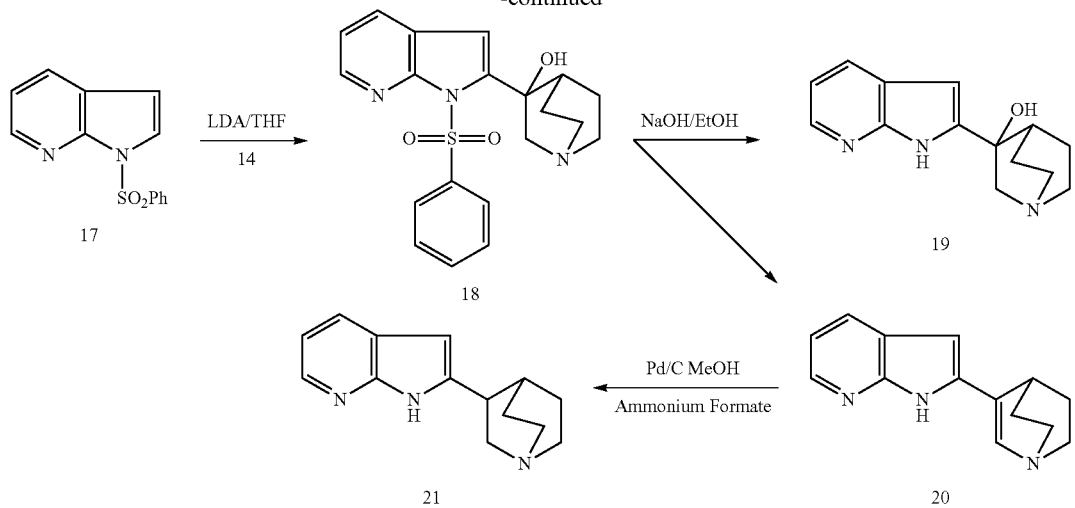

The generations of anions at the ortho position of the aromatic systems employed in the synthetic procedures described in this application is encompassed under a general synthetic strategy known to those skilled in the art as Directed Ortho Metalation (DOM). Within this area, a number of functional groups known as Directed Metalation Groups (DMG's) have been studied for this purposes. The 1-phenylsulfonyl group as DMG in the 1-position of azaindole analogs enables the lithiation of the 2-position and thereby its functionalization (*Synthesis*, 2005[2]; *Tetrahedron*, 1997).

The 2-lithioderivate of 17, which was prepared on multigram scale by α-metallation (1.1 equiv. LDA, THF, −10° C. to 0° C.) was trapped with 14, leading to compound 18, which was deprotected to produce a mixture of the anticipated alcohol 19 and enamine 20. Then the reduction of 20 was performed to yield 3-(1H-pyrolo[2,3-b]pyridine-2-yl)-1-aza-bicyclo[2,2,2]octane (21).

Scheme 4

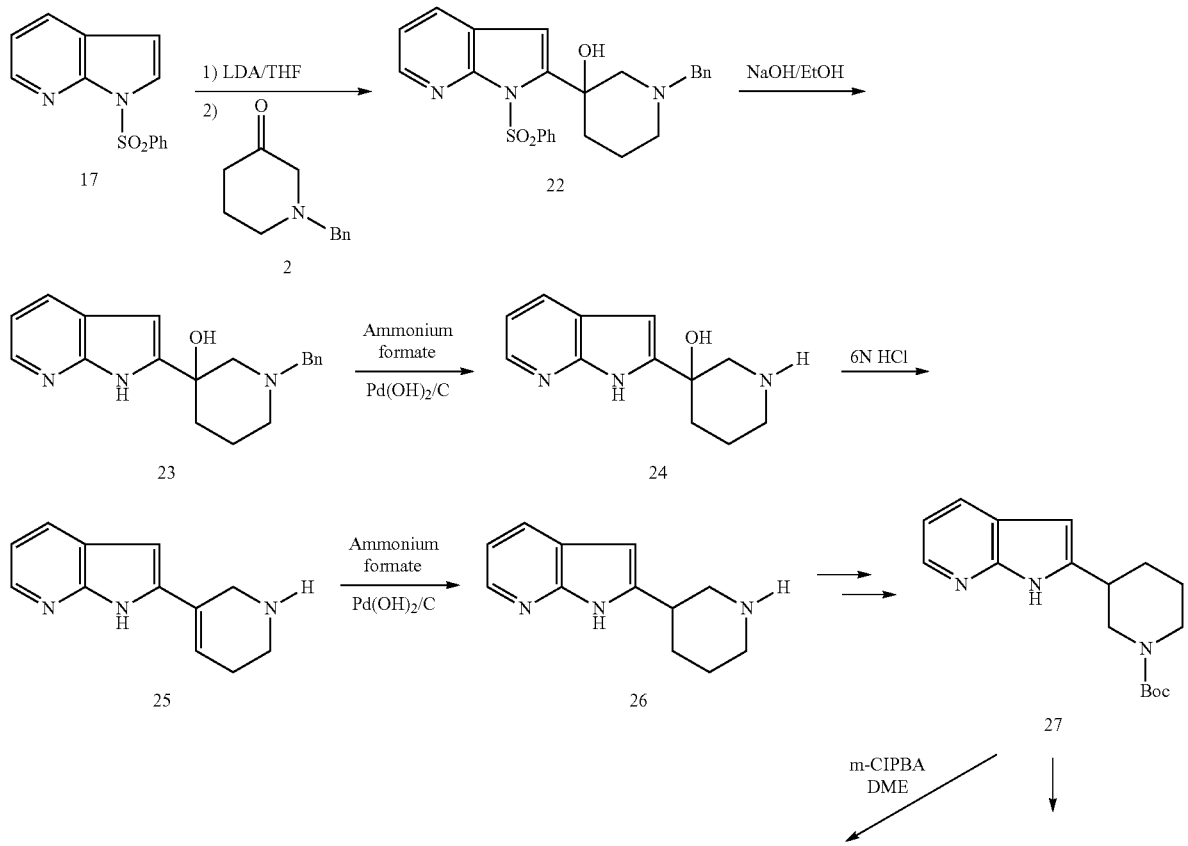

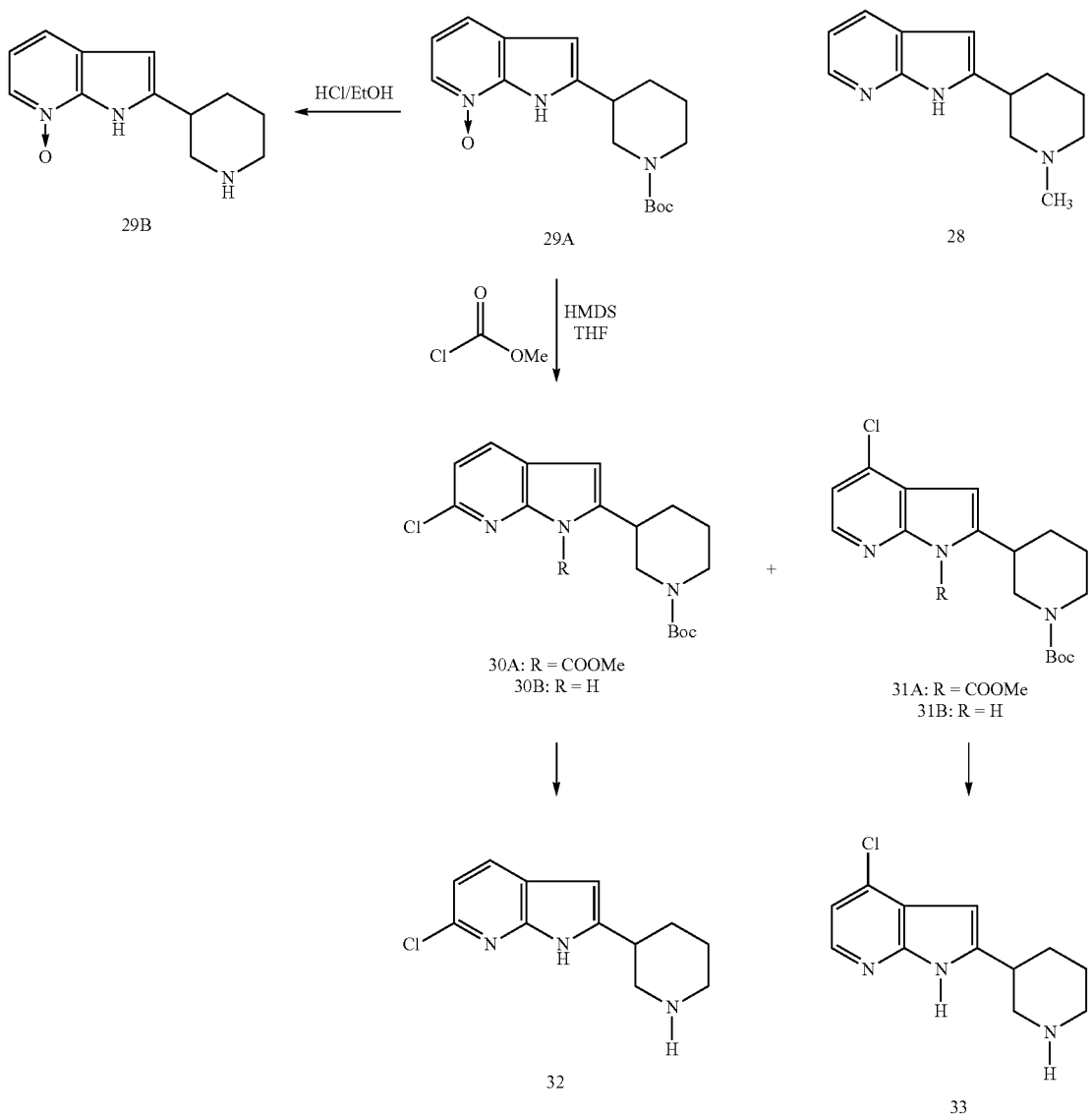

Referring to scheme 3, the starting material 17 was converted to compound 22 (scheme 4). The $N_1$-phenylsulfonyl group was hydrolyzed using NaOH/MeOH (23), the benzyl group was removed (24) and the compound was dehydrated (25). Reduction generated the desired compound 26 (2-piperidin-3-yl-1H-pyrrolo[2,3-b]-pyridine). Referring to scheme 2, reduction of 27 with a strong reducing agent, for example LiAlH$_4$, was used to generate the N—CH$_3$ compound (28).

Furthermore, by the sequence described in scheme 2, starting material 27 was converted into a separable mixture of 30 and 31 (scheme 4). The non-selectivity of this specific Reissert-Henze type reaction (through the N-oxide 29A) will be understood by those skilled in the art. Then, basic hydrolysis was performed, followed by removal of the N-t-Boc protecting group, which yielded the corresponding 6-(or 4)-chloro-2-piperidin-3-yl-1H-pyrrolo[2,3-b]pyridines (32 and 33).

Scheme 5

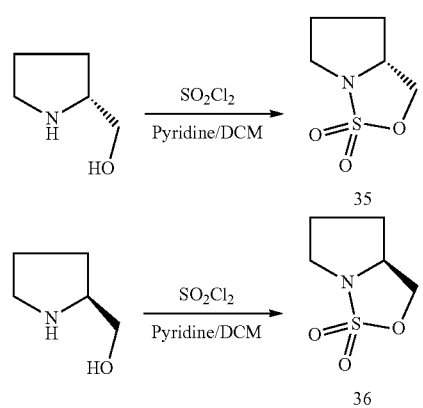

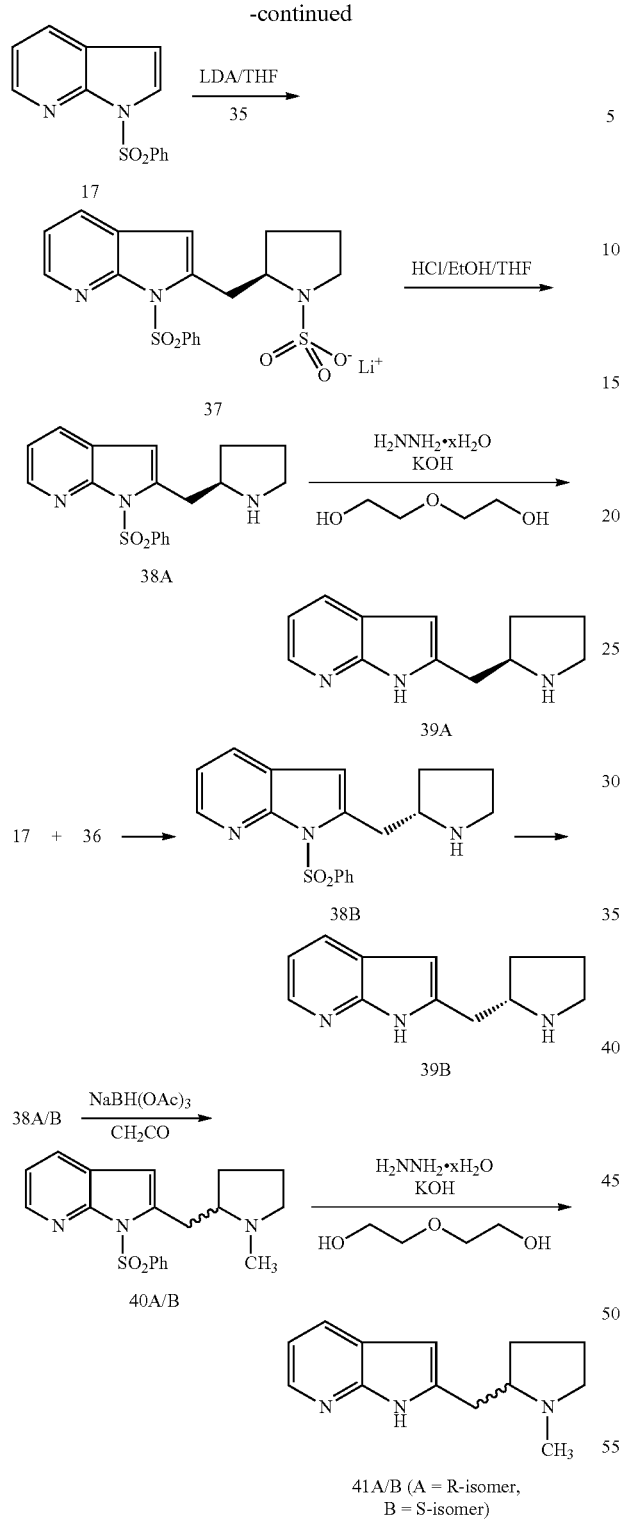

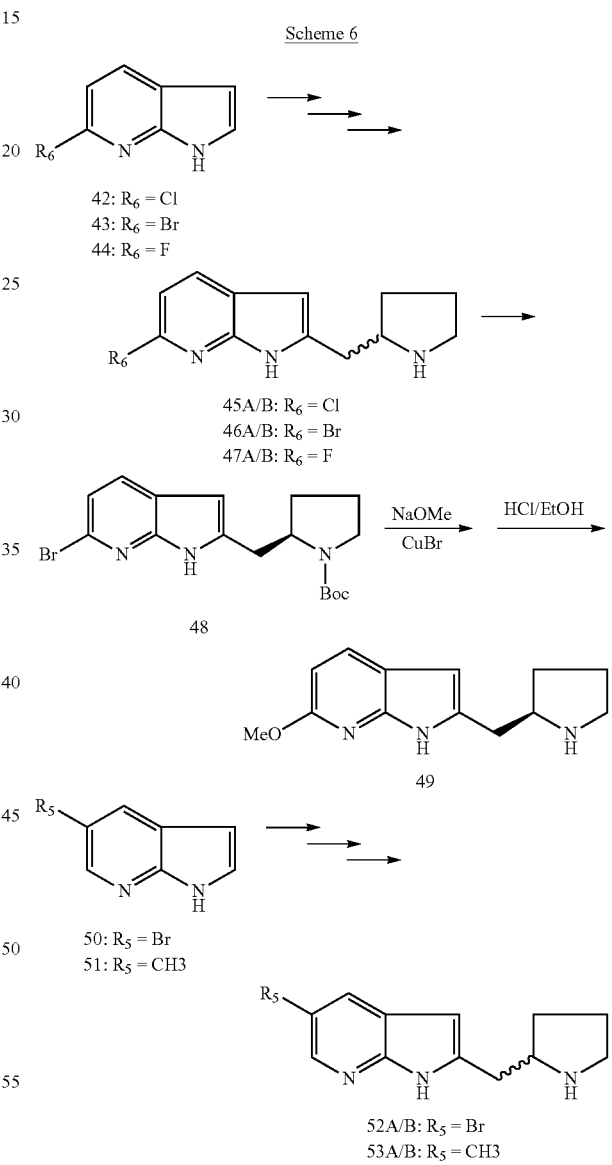

N1-phenylsulfonyl group was accomplished using well known methods, for example, compound 38A was reacted with potassium hydroxide in diethylene glycol in the presence of hydrazine, which generated (R)-2-pyrrolidin-2-ylmethyl-1-H-pyrrolo[2,3-b]pyridine (39A). De (S)-derivate 39B was obtained starting from the (S)-sulphamidate 36. Reductive alkylation of 39A to compound 41A (scheme 5) can be accomplished using different methods. Alternative to the conversion of 26 to 28 that was performed in scheme 4, in scheme 5 reductive methylation of 38A and subsequent removal of the N1-phenylsulfonyl group in compound 40A was performed to generate the desired (R)-2-(1-methyl-pyrrolidin-2ylmethyl)-1-H-pyrrolo[2,3-b]pyridine (41A).

In another aspect, 5-(R)-[3,3,0]-1-aza-2-thia-3-oxabicyclooctane-2,2-dioxide (compound 35, scheme 5) or the 5-(S)-analog (compound 36, *Tetrahedron Asymmetry*, 1990) was employed as starting materials for synthesizing compounds of formula I of the present invention, The 2-lithioderivate of 17 was reacted with (R)-sulphamidate 35 to produce the lithium-sulfonate 37, which was subsequently hydrolysed to generate 38A. Removal of the Scheme 6 illustrates the preparation of compounds of the formula I wherein $R_6$ and $R_6$, which are the same or different, are chosen from a halogen atom, a $(C_{1-3})$alkyl group and an alkyloxy group. The foregoing procedure (using the chiral sulphamidates 35 and 36) was used to convert 42 and 43 (*Synthesis*, 1992), 44 (scheme 7), 50 (*Heterocycles*, 1999) and 51 (*Current Organic Chemistry*, 2001) to the corresponding compounds 45A/B, 46A/B, 47A/B, 52A/B and 53A/B.

An example of functionalization of the 7-azaindole system at position 6, was performed by the Cu(I)bromide catalyzed conversion of 48 (and subsequent removal of the t-Boc protecting group) to afford (R)-6-methoxy-2-pyrrolidin-2-ylm-ethyl-1-H-pyrrolo[2,3-b]-pyridine (49).

It should be emphasized that the synthesis of 6-fluoro-7-azaindole (44) has not yet been reported. However, the present invention provides a method to generate compound 44 based on synthetic strategies known to those skilled in the art and illustrated in scheme 7.

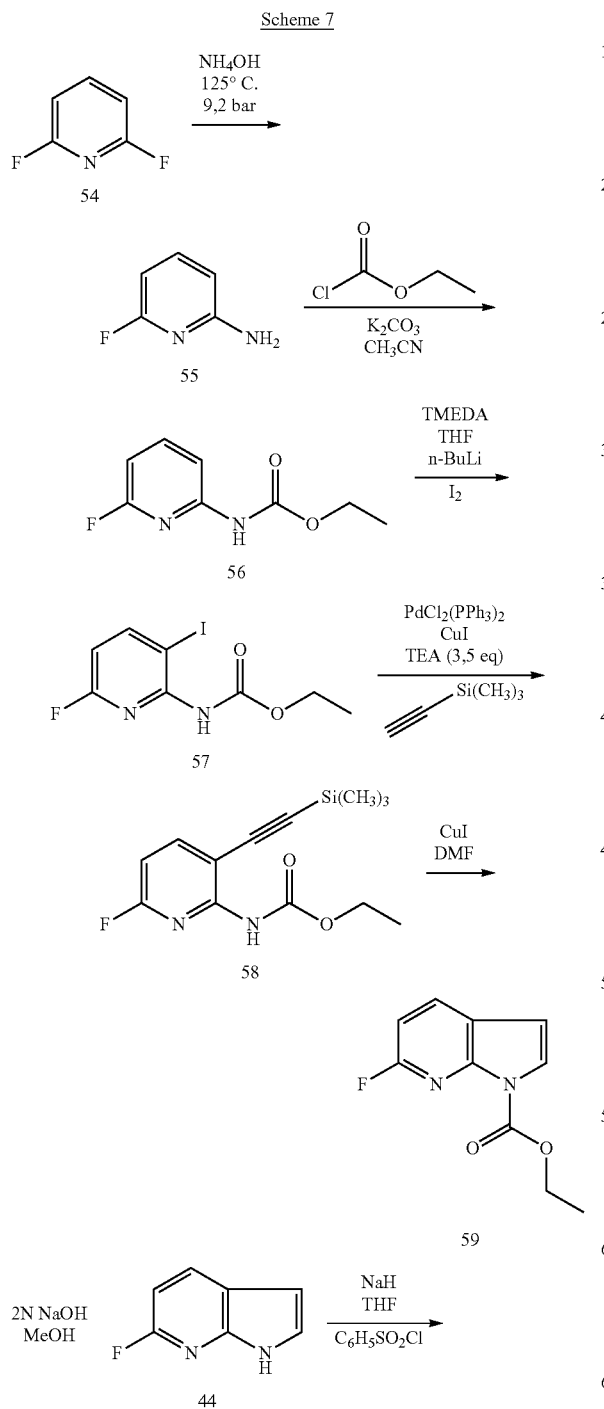

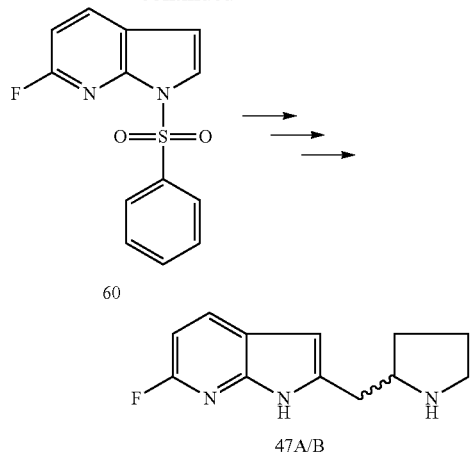

Commercially available 2,6-difluoropyridine (54) was converted to 2-amino-6-fluoro-pyridine (55, *Tetrahedron*, 2002). Different DMG groups were examined (for example the 2,2-dimethyl-propanamide, (*Heterocycles*, 1999; WO 2003/053970). It was found however, that a carbamate as DMG (*Chem. Pharm. Bull.*, 1987) was particularly useful for the selective iodination of compound 56 to generate compound 57 (6-fluoro-3-iodo-pyridin-2-yl)-carbamic acid ethyl ester.

Subsequent Sonogashira chemistry, followed by ring closure in the presence of Cu(I)iodide (*Synthesis*, 2005[1]) was performed, which afforded compound 59. Cleavage of the $N_1$-carbamate generated 6-fluoro-1H-pyrrolo[2,3-b]pyridine (44).

The synthesis of compounds 47A/B has been illustrated and performed in scheme 6 according to the procedures illustrated and performed in scheme 5.

Another illustration of a synthesis that was used to produce compounds of the present invention of formula I is shown in scheme 8.

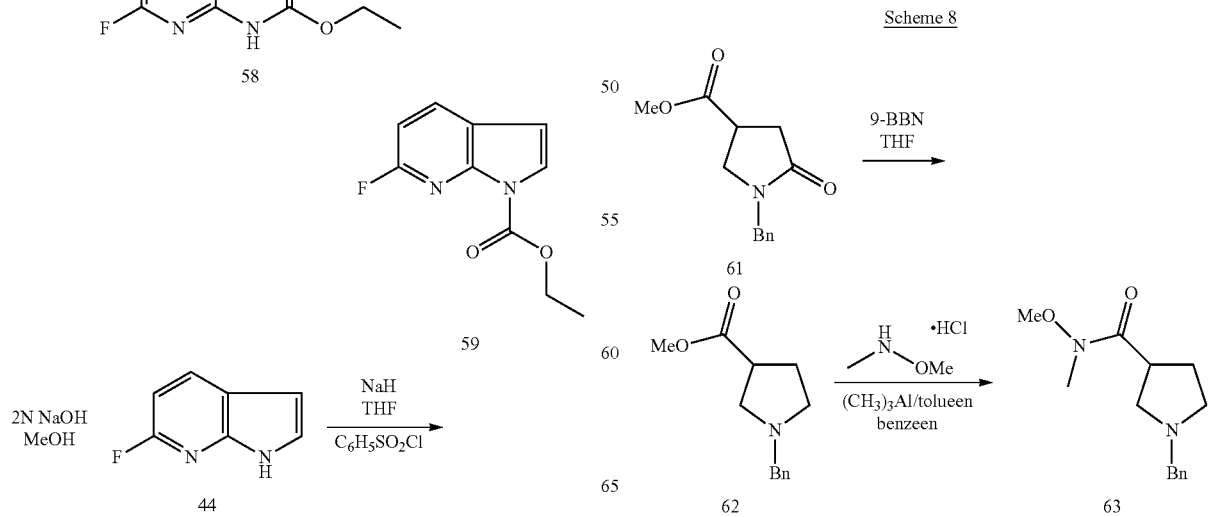

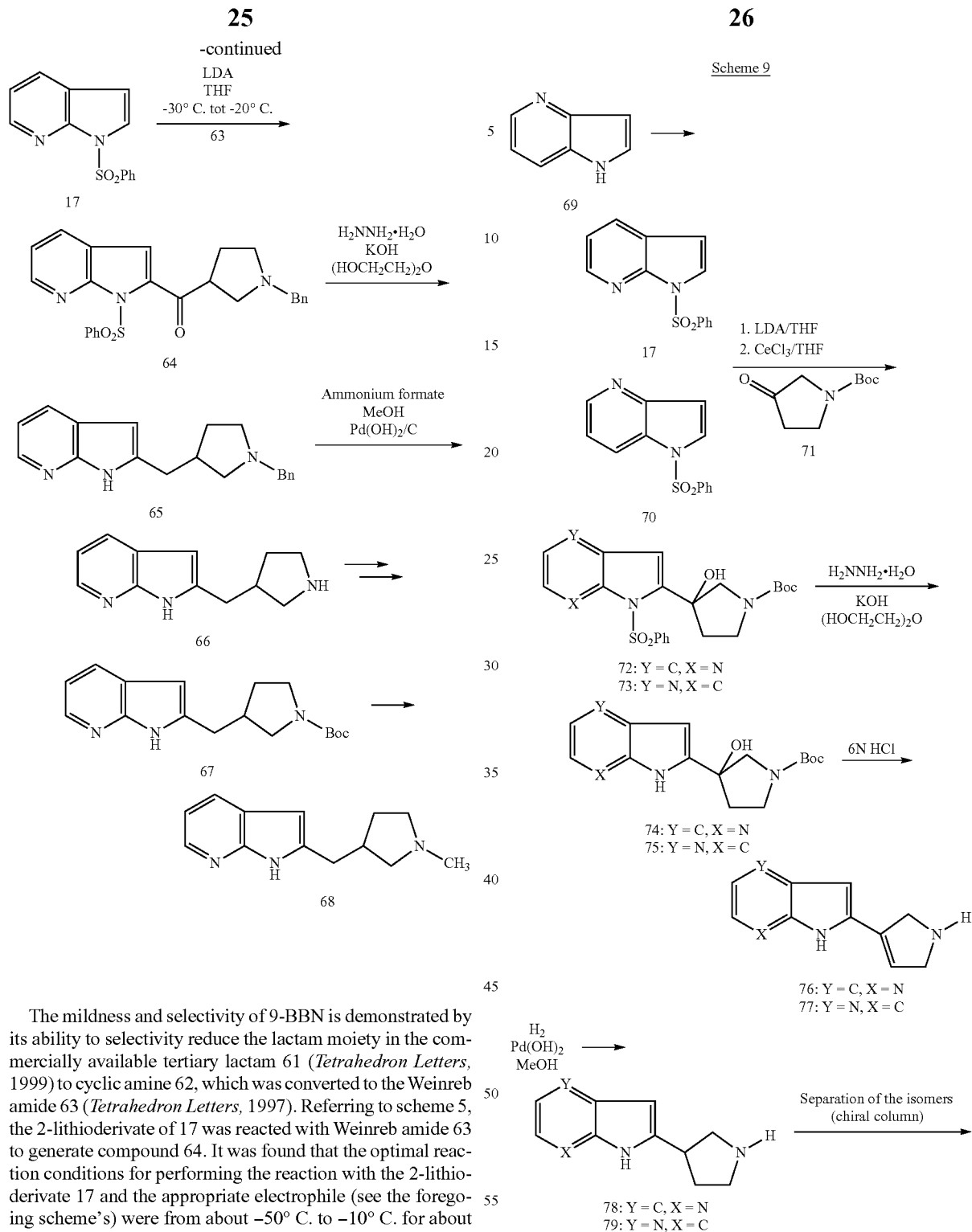

The mildness and selectivity of 9-BBN is demonstrated by its ability to selectivity reduce the lactam moiety in the commercially available tertiary lactam 61 (*Tetrahedron Letters*, 1999) to cyclic amine 62, which was converted to the Weinreb amide 63 (*Tetrahedron Letters*, 1997). Referring to scheme 5, the 2-lithioderivate of 17 was reacted with Weinreb amide 63 to generate compound 64. It was found that the optimal reaction conditions for performing the reaction with the 2-lithioderivate 17 and the appropriate electrophile (see the foregoing scheme's) were from about −50° C. to −10° C. for about 2 hours, or, for example, at −30° C. to −20° C. for about 2 hours.

Compound 64 was subjected to a Huang-Minlon reduction with concomitant cleavage of the $N_1$-phenylsulfonyl group to generate compound 65. Subsequent reductive cleavage of the benzyl group was accomplished under the conditions as described before (scheme 4) to generate 2-pyrrolidin-3-ylmethyl-1H-pyrrolo[2,3-b]pyridine (66).

Conversion of 66 to 67, using the methodology described in scheme 4, and subsequent reduction yielded compound 68.

In yet another example of the general procedure (scheme 9), the 2-lithioderivate of 17 (or 70) was reacted with Ce(III) chloride (*J. Med. Chem.*, 2002) and subsequently trapped with 3-oxo-pyrrolidin-1-carboxylic acid tert-butyl ester (71) to yield the corresponding tertiary alcohols (72, 73). Referring to scheme 5, the $N_1$-cleavage of the phenylsulfonyl group generated compounds 74, 75. An Acidic medium (for example, 6 M HCl) was used to catalyze the removal of the N-t-Boc protecting group; and subsequent dehydration generated compounds 76, 77, which were reduced to the desired 2-pyrrolidin-3-yl-1H-pyrrolo[2,3-b]pyridine (78) and 2-Pyrrolidin-3-yl-1H-pyrrolo[3,2-b]pyridine (79). Separation of the isomers was achieved using a chiral column.

For the preparation of 83 (scheme 10, European Journal of Medicinal Chemistry, 2004).

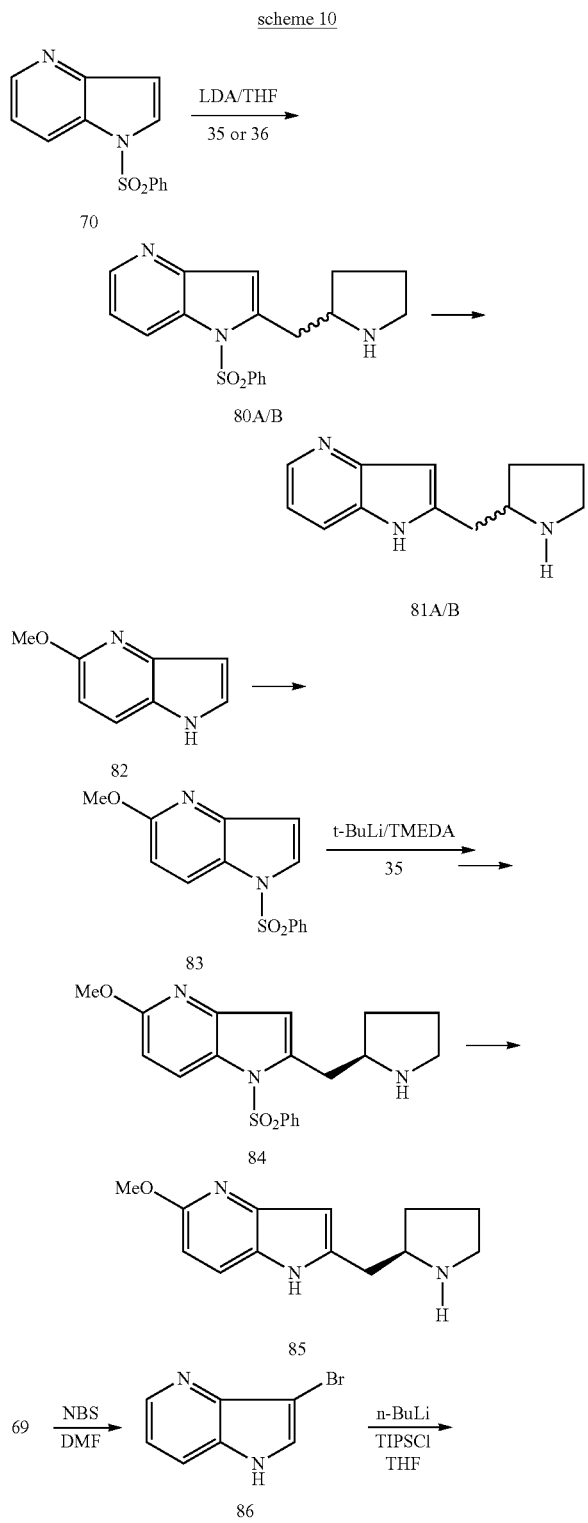

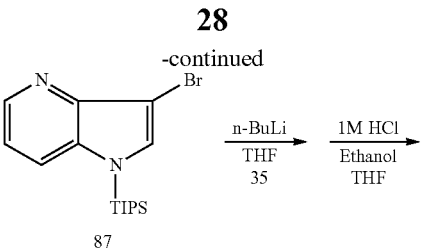

The 2-lithioderivate of 70 and or 83 (accomplished with, for example, t-BuLi/TMEDA in THF) was reacted with 35 or 36 to yield the corresponding compounds 80A/B and 84. Conversion of 80A/B and 84 to 81A/B and 85 was performed using the methodology described in scheme 5.

Bromination of the 3-position in the different isomeric azaindoles, can be accomplished by known methods (*Heterocycles*, 1999, 2000; *Tetrahedron Letters*, 1969; WO2004/078757). Surprisingly it was found, that, for example in scheme 10, when NBS/DMF was used, it allowed the bromination (of 69 to 86) to occur in almost quantitative yield. The proper choice of a protecting group, in particular the triisopropylsilyl group (TIPS), enabled the exchange of the 3-bromo to the 3-lithioderivate of 87, which was subsequently trapped with the (R)-sulphamidate (compound 35). Then, acidic removal of the TIPS followed by hydrolysis of the sulfonate group (referring to scheme 5) generated the desired (R)-3-pyrolidin-2ylmethyl-1H-pyrrolo[3,2-b]pyridine (88).

Another illustration of preparation of compounds of the present invention of formula I is shown in scheme 11.

Commercially available 4-chloro-7H-pyrrolo[2,3-d]pyrimidine (89) was reductively converted to 7H-pyrrolo[2,3-d]pyrimidine (90). The 2-(trimethylsilyl)ethoxy-methyl group as DMG in the 1-position of the indole derivates enabled the lithiation of the 2-position (*Helvetica Chimica Acta*, 1993).

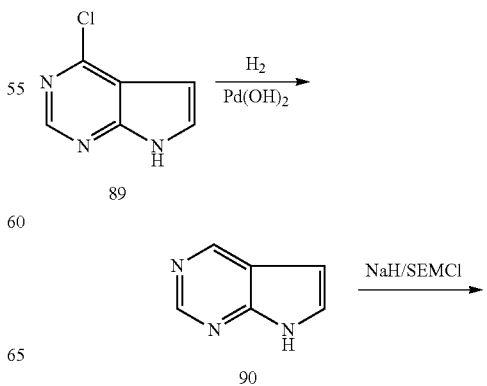

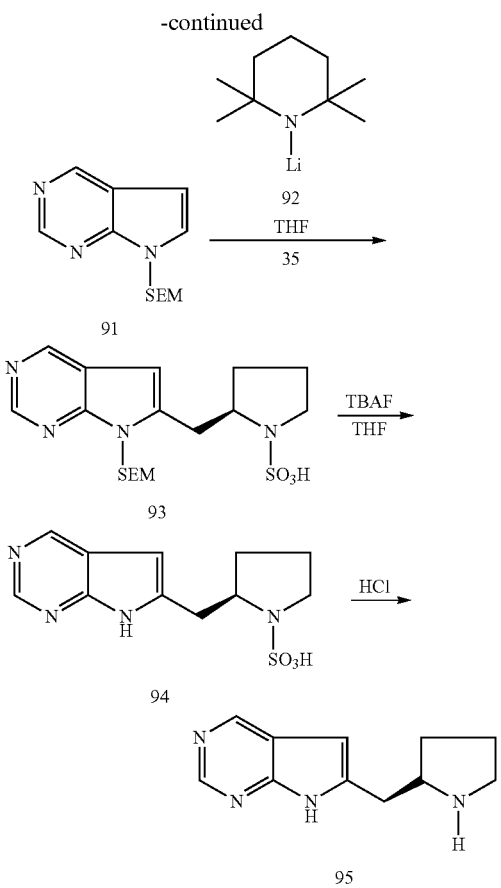

Using this well known methodology, the 2-lithioderivate of 91 was trapped with (for example) compound 35. To avoid the problems associated with the use of alkyllithiums or lithium dialkylamides, the proper choice in this instance was lithium tetramethylpiperidine (92). The 2-lithioderivate of 91 was reacted with (R)-sulphamidate (35) to generate compound 93. Subsequently the SEM protecting group was removed (94). Then, the sulfonate group was hydrolyzed under standard conditions, as described above, which yielded (R)-6-pyrrolidin-2-ylmethyl-7-H-pyrrolo[2,3-d]pyrimidine (95).

Pharmaceutically acceptable salts may be obtained using standard procedures well known in the art, for example by mixing a compound of the present invention with a suitable acid, for instance an inorganic acid or an organic acid.

Example 3

Synthesis of Specific Compounds

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

1-Benzyl-3-(1H-pyrrolo[2,3-b]pyridin-3-yl)-piperidin-3-ol. (compound 3)

A 60% dispersion of NaH in mineral oil (9.5 g, 179 mmol) was slowly added to 150 ml EtOH (0° C.). This solution was added to 7-azaindole (5.3 g, 44.9 mmol) and 11.25 g (44.9 mmol) 1-benzyl-piperidin-3-one (as HCl salt). The resulting mixture was stirred for 72 hours at room temperature. Ethylacetate was added to the mixture and the organic layer was washed three times with a saturated NaHCO$_3$ solution, dried (Na$_2$SO$_4$), filtered and concentrated. The resulting residue was purified by flash chromatography (diethyl ether/ethylacetate gradient (1:1 to pure ethylacetate)) to give compound 3 as an oil (10.3 g, 74.7%). $^1$H-NMR (400 MHz, CDCl$_3$): δ 10.0 (bs, 1H), 8.27 (dd, J=5 Hz, 2 Hz, 1H), 8.14 (dd, J=8 Hz, 2 Hz, 1H), 7.35-7.24 (m, 6H), 7.03 (dd, J=5 Hz, 8 Hz, 1H), 3.96-3.88 (bs, 1H), 3.60 (dd, J gem=13 Hz, 2H), 3.07-3.01 (m, 1H), 2.95-2.89 (m, 1H), 2.39 (d, J=10 Hz, 1H), 2.16-1.96 (m,2H), 1.92-1.78 (m, 2H), 1.72-1.65 (m, 1H). (TLC EtOAc R$_f$ 0.09).

3-(1H-Pyrrolo[2,3-b]pyridin-3-yl)-piperidin-3-ol. (compound 4)

Compound 3 (2.4 g, 7.8 mmol), 1.5 g ammonium formate (23.8 mmol) and 20% Pd(OH)$_2$/C (240 mg) were combined in MeOH (50 ml) and warmed to reflux for 2 hours. The mixture was cooled, filtered, concentrated and re-dissolved in MeOH. Filtration over 25 g SCX-2 (MeOH followed by 1 N NH$_3$/MeOH) gave the title compound (1.5 g, 6.9 mmol, 88%) as amorphous material, $^1$H-NMR (400 MHz, D$_6$DMSO): δ 11.3 (bs, 1H), 8.17-8.13 (m, 2H), 7.24 (s, 1H), 7.0-6.95 (m, 1H), 3.0-2.89 (m, 2H), 2.85 (d, J=13 Hz, 1H), 2.6-2.51 (m, 1H), 2.06-1.8 (m, 3H), 1.5-1.42 (m, 1H). (TLC MeOH/triethylamine (97/3 R$_f$ 0.16).

3-(1,2,5,6-Tetrahydro-pyridin-3-yl)-1H-pyrrolo[2,3-b]pyridine. (compound 5)

10 ml acetylchloride was slowly added to 200 ml of EtOH (−10° C.). After 15 minutes, this solution was added to compound 4 (5 g, 16.3 mmol) and heated to reflux for 1 hour. The mixture was cooled, concentrated and re-dissolved in MeOH. Filtration over 25 g SCX-2 (MeOH followed by 1 N NH$_3$/MeOH) gave the title compound (1.43 g, 7.18 mmol, 44.1%) as amorphous material. $^1$H-NMR (400 MHz, CDCl$_3$): δ 11.4-10.8 (bs, 1H), 8.32 (dd, J=5 Hz, 2 Hz, 1H), 8.2 (dd, J=8 Hz, 2 Hz, 1H), 7.15 (dd, J=8 Hz, J=5 Hz, 1H), 6.32-6.27 (m, 1H), 3.76-3.72 (m, 2H), 3.10-3.04 (m, 2H), 2.36-2.29 (m, 2H). (TLC MeOH/triethylamine (97/3 R$_f$ 0.25).

3-Piperidin-3-yl-1H-pyrrolo[2,3-b]pyridine. (compound 6)

10 ml acetylchloride was slowly added to 200 ml of MeOH (−10° C.). After 15 minutes, this solution was added to compound 5 (1.43 g, 7.18 mmol) and 20% Pd(OH)$_2$/C (130 mg). The mixture was hydrogenated at 50 psi for 1 hour. The mixture was filtered and concentrated. A subsequent filtration over SCX-2, followed by flash chromatography (MeOH/triethylamine (97/3) afforded compound 6 (0.81 g, 4.02 mmol, 55%) which was reacted with 1 equivalent of fumaric acid in EtOH and concentrated. Recrystallization from EtOH/ethylacetate afforded a solid (free base/fumaric acid (2:1)), mp>225° C. (decomposition). $^1$H-NMR (400 MHz, D$_2$O): δ 8.04 (bd, J=5 Hz, 1H), 7.93 (bd, J=8 Hz, 1H), 7.13 (bs, 1H), 7.01 (dd, J=8 Hz, 5 Hz, 1H), 6.36 (s, 1H), 3.46-3.40 (m, 1H), 3.37-3.31 (m, 1H), 3.14-3.04 (m, 1H), 2.92-2.82 (m, 2H), 2.0-1.87 (m, 2H), 1.8-1.54 (m, 2H).

3-(1H-Pyrrolo[2,3-b]pyridin-3-yl)-piperidine-1-carboxylic acid tert-butyl ester. (compound 9)

Compound 6 (0.3 g, 1.5 mmol), 1.0 g di-t-butyl-dicarbonate (4.58 mmol) and 0.5 ml triethylamine were combined in dichloromethane (20 ml) and warmed to reflux for 15 minutes. The mixture was cooled and concentrated in vacuo. The resulting residue was taken up in ethylacetate, washed with brine, dried (Na$_2$SO$_4$), filtered and concentrated in vacuo to afford compound 8 as an oily residue, which was used as in the next step (no further purification was needed). $^1$H-NMR (400 MHz, CDCl$_3$): δ 8.5 (dd, J=5 Hz, 2 Hz, 1H), 7.98-7.91 (bd, J=8 Hz, 1H), 7.39 (s, 1H), 7.18 (dd, J=8 Hz, 5 Hz, 1H), 4.48-4.04 (m, 2H), 2.97-2.75 (m, 3H), 2.2-2.14 (m, 1H), 1.84-1.63 (m, 3H), 1.67 (s, 9H), 1.49 (s, 9H). (TLC diethyl ether R$_f$ 0.39). This material (8) was dissolved in 10 ml MeOH and 3 ml 2 N NaOH. The reaction mixture was stirred for 0.5 hour at room temperature. Ethyl acetate was added to the mixture and the organic layer was washed three times with 2 N NaOH, dried (Na$_2$SO$_4$), filtered and concentrated. The resulting residue was purified by flash chromatography (diethyl ether) to afford compound 9 as an oil (0.25 g, 0.83 mmol, 55% (overall)). $^1$H-NMR (400 MHz, CDCl$_3$): δ 9.8 (bs, 1H), 8.3 (bd, J=5 Hz, 1H), 8.04-7.98 (bd, J=8 Hz, 1H), 7.13 (bs, 1H), 7.07 (dd, J=8 Hz, 5 Hz, 1H), 4.45-4.02 (m, 2H), 3.04-2.76 (m, 3H), 2.2-2.14 (m, 1H), 1.83-1.60 (m, 3H), 1.49 (s, 9H), (TLC diethyl ether R$_f$ 0.13).

3-(7-Oxy-1H-pyrrolo[2,3-b]pyridin-3-yl)-piperidine-1-carboxylic acid tert-butyl ester. (compound 10A)

Compound 9 (0.23 g, 0.76 mmol) and 0.23 g meta-chloroperbenzoic acid (1.4 eq., 1.07 mmol) were combined in dimethoxyethane (10 ml) and stirred for 10 minutes at room temperature. The mixture was concentrated on SiO$_2$ and purified by flash chromatography (ethyl acetate followed by ethyl acetate/MeOH/triethylamine (9010/1) to afford compound 10A (amorphous, 0.23 g, 0.72 mmol, 95%). $^1$H-NMR (400 MHz, CDCl$_3$): δ 8.2 (bd, J=5 Hz, 1H), 7.8-7.5 (bs, 1H), 7.22 (s, 1H), 7.04 (dd, J=8 Hz, 5 Hz, 1H), 4.44-4.02 (m, 2H), 2.99-2.78 (m, 3H), 2.2-2.12 (m, 1H), 1.81-1.60 (m, 3H), 1.48 (s, 9H).

3-Piperidin-3-yl-1H-pyrrolo[2,3-b]pyridine 7-oxide. (compound 10B)

0.4 ml acetylchloride was slowly added to 10 ml of EtOH (−10° C.). After 15 minutes, this HCl/EtOH solution was added to compound 10A (0.27 g, 0.85 mmol) and heated to reflux for 1 hour. The mixture was cooled and partly concentrated, ethyl acetate was added and the resulting precipitate was collected by filtration and washed with diisopropylether. The title compound (10B, as HCl salt) was obtained as a solid (220 mg, 100%). mp>145° C. (decomposition). $^1$H-NMR (400 MHz, D$_2$O): δ N$_1$—H was invisible, 8.21-8.18 (m, 1H), 8.15-8.12 (m, 1H), 7.40 (bs, 1H), 7.25-7.0 (m,1H), 3.56-3.49 (m, 1H), 3.41-3.34 (m, 1H), 3.31-3.22 (m, 1H), 3.04-2.90 (m, 2H), 2.14-2.06 (m, 1H), 2.05-1.94 (m, 1H), 1.86-1.66 (m, 2H).

6-Chloro-3-piperidin-3-yl-1H-pyrrolo[2,3-b]pyridine. (compound 13)

Compound 10A (0.22 g, 0.69 mmol) and 0.15 ml 1,1,1,3,3,3-hexamethyldisilazane (0.72 mmol) were combined in 10 ml THF. To this solution was added 0.14 ml (1.8 mmol) methyl chloroformate and the reaction mixture was stirred for 30 minutes at room temperature. The reaction was concentrated in vacuo. The resulting residue was taken up in ethyl acetate, washed with a 5% NaHCO$_3$ solution followed by brine, dried (Na$_2$SO$_4$), filtered and concentrated in vacuo. Purification by flash chromatography (diethyl ether/PA: 1/1) afforded compound 11 as an oil (0.16 g, 58.6%). $^1$H-NMR (400 MHz, CDCl$_3$) δ 7.95-7.84 (bd, J=8 Hz, 1H), 7.53 (s, 1H), 7.24 (d, J=8, 1H), 4.42-4.20 (m, 1H), 4.10-4.01 (m, 1H), 4.09 (s, 3H), 3.14-2.84 (m, 2H), 2.84-2.68 (m, 1H), 2.19-2.11 (m, 1H), 1.82-1.60 (m, 3H), 1.49 (s, 9H). (TLC diethyl ether/PE (1/1) R$_f$ 0.19).

Compound 11 (0.16 g) was dissolved in 25 ml MeOH containing 3 ml 2N NaOH and stirred for 18 hours at room temperature. The reaction was concentrated in vacuo. The resulting residue was taken up in dichloromethane, washed with a 5% NaHCO$_3$ solution followed by brine, dried (Na$_2$SO$_4$), filtered and concentrated in vacuo to yield compound 12 (0.13 g, 95%). $^1$H-NMR (400 MHz, CDCl$_3$) δ 7.99-7.91 (bd, J=8 Hz, 1H), 7.12-7.07 (m, 2H), 4.42-4.20 (m, 1H), 4.16-4.02 (m, 1H), 3.02-2.75 (m, 3H), 2.20-2.12 (m, 1H), 1.82-1.60 (m, 3H), 1.49 (s, 9H). (TLC diethyl ether/PE (1/1) R$_f$ 0.17).

0.2 ml acetylchloride was slowly added to 10 ml of EtOH (−10° C.). After 15 minutes, this solution was added to compound 12 (0.13 g, 0.39 mmol) and heated to reflux for 1.5 hour. The mixture was cooled and partly concentrated, ethyl acetate was added and the resulting precipitate was collected by filtration and washed with diisopropylether.

The title compound, 6-chloro-3-piperidin-3-yl-1H-pyrrolo [2,3-b]pyridine 13 (as HCl salt) was obtained as a solid (80 mg, 76%). mp>279° C. (decomposition). $^1$H-NMR (400 MHz, D$_2$O): δ 7.60 (d, J=8 Hz, 1H), 7.14 (s, 1H), 6.99 (d, J=8 Hz, 1H), 3.52-3.44 (m, 1H), 3.40-3.32 (m, 1H), 3.19-3.09 (m, 1H), 2.97-2.87 (m, 2H), 2.08-1.91 (m, 2H), 1.84-1.60 (m, 2H).

3-(1H-Pyrrolo[2,3-b]pyridin-3-yl)-1-aza-bicyclo [2.2.2]octane. (comp. 16)

A 60% dispersion of NaH in mineral oil (4 g, 75 mmol) was slowly added to 75 ml EtOH (0° C.). This solution was added to 7-azaindole (2 g, 16.9 mmol) and 3.4 g (21 mmol) 1-aza-bicyclo[2.2.2]octan-3-one (14) (as HCl salt). The resulting mixture was stirred for 24 hours at 60° C. The solution was allowed to attain room temperature. To the reaction mixture was added 0.5 ml H$_2$O and 25 g SiO$_2$ and subsequently concentrated in vacuo. The resulting residue was purified by flash chromatography (dichloromethane/MeOH/7N NH$_3$/MeOH (960/35/5 to 910/100/10)) to give compound 15 as a solid (2.5 g, 69%). mp 180° C. $^1$H-NMR (400 MHz, D$_6$DMSO): δ 11.8 (bs, 1H), 8.24 (dd, J=5 Hz, 2 Hz, 1H), 8.12 (dd, J=8 Hz, 2 Hz, 1H), 7.61 (s,1H), 7.08 (dd, J=5 Hz, 8 Hz, 1H), 6.87 (d, J=2 Hz, 1H), 3.14-3.09 (m, 1H), 3.01-2.91 (m, 2H), 2.64-2.54 (m, 2H), 1.78-1.69 (m,2H), 1.59-1.49 (m, 2H).

Compound 15 (1.9 g, 7.11.95 mmol) and 20% Pd(OH)$_2$/C (190 mg) were combined in MeOH (100 ml). The mixture was hydrogenated at 50 psi for 72 hour. The mixture was filtered and concentrated on 25 g of SiO$_2$. The resulting residue was purified by flash chromatography (dichloromethane/MeOH/7N NH$_3$/MeOH (960/35/5 to 910/100/10)) to give the title compound 16 as a solid (1.55 g, 57%). mp 185° C. $^1$H-NMR (400 MHz, D$_6$DMSO): δ 11.35 (bs, 1H), 8.17 (dd, J=5 Hz, 2 Hz, 1H), 7.85 (dd, J=8 Hz, 2 Hz, 1H), 7.31 (d, J=2 Hz, 1H), 6.98 (dd, J=5 Hz, 8 Hz, 1H), 3.32-3.24 (m, 1H), 3.22-2.95 (m, 1H), 3.0-2.83 (m, 4H), 2.78-2.68 (m, 1H), 1.95-1.91 (m, 1H), 1.84-1.54 (m, 3H), 1.35-1.24 (m, 1H).

3-(1-Benzenesulfonyl-1H-pyrrolo[2,3-b]pyridin-2-yl)-1-aza-bicyclo[2.2.2]octan-3-ol. (comp. 18)

LDA (2.0 M in THF/heptane) (5.5 ml, 11 mmol) was added to 100 ml anhydrous THF at −10° C. under N$_2$. A solution of anhydrous THF (10 ml) containing compound 17 (*Tetrahedron*, 1997) (2.58 g, 10 mmol) was added dropwise. After the addition, the resulting solution was stirred for 30 minutes at −10° C.-0° C. Then the temperature was lowered to −70° C. At this temperature, a solution of 14 (1.25 g, 10 mmol) in 10 ml THF was added dropwise. The free base of the HCl salt of commercially available 1-aza-bicyclo[2.2.2]octan-3-one (14) was obtained after filtration over SCX-2 (MeOH followed by 1 N NH$_3$/MeOH) and subsequent evaporation. After the addition of 14, the temperature was raised to −30° C.-25° C. and the resulting solution was stirred for 60 minutes. The solution was allowed to attain room temperature. To the reaction mixture was added 5 ml H$_2$O and 50 g SiO$_2$ and subsequently concentrated in vacuo. The resulting residue was purified by flash chromatography (dichloromethane/MeOH/ 7N NH$_3$/MeOH (960/35/5)) to give compound 18 as an oil (1.4 g, 37%). $^1$H-NMR (200 MHz, CDCl$_3$): δ 8.30 (dd, J=5 Hz, 2 Hz, 1H), 8.15-8.05 (m, 2H), 7.75 (dd, J=8 Hz, 2 Hz, 1H), 7.60-7.38 (m, 3H), 7.12 (dd, J=5 Hz, 8 Hz, 1H), 6.71 (s, 1H), 5.10-4.85 (bs, 1H), 3.20-2.74 (m, 6H), 2.45-2.25 (m, 1H), 2.08-1.92 (m, 2H), 1.74-1.44 (m, 2H). (TLC dichloromethane/MeOH/7N NH$_3$/MeOH (960/35/5)) R$_f$ 0.33).

3-(1H-Pyrrolo[2,3-b]pyridin-2-yl)-1-aza-bicyclo [2.2.2]octane. (comp. 21)

Compound 18 (2.4 g, 6.26 mmol) and 31 ml 2N NaOH were combined in EtOH (310 ml) and warmed to reflux for 2 hours. The mixture was cooled and concentrated. To the residue was added 50 g SiO$_2$ and 100 ml MeOH. This mixture was concentrated in vacuo and subsequently purified by flash chromatography (dichloromethane/MeOH/7N NH$_3$/MeOH (960/35/5)) to give compound 20 as an oil (0.54 g, 38.3%). $^1$H-NMR (200 MHz, CDCl$_3$): δ 11.3 (bs, 1H), 8.33 (dd, J=5 Hz, 2 Hz, 1H), 7.87 (dd, J=8 Hz, 2 Hz, 1H), 7.14-7.02 (m, 2H), 6.52 (bs, 1H), 3.25-2.65 (m, 5H), 1.95-1.40 (m, 4H) (TLC dichloromethane/MeOH/7N NH$_3$/MeOH (960/35/5)) R$_f$ 0.20). The second compound obtained during this chromatography (19) was obtained as a solid (0.71 g, 46.6%). mp 272° C. $^1$H-NMR (400 MHz, D$_6$DMSO): δ 11.38 (s, 1H), 8.17 dd, J=5 Hz, 2 Hz, 1H), 7.87 ((dd, J=8 Hz, 2 Hz, 1H), 7.02 (dd, J=8 Hz, 5 Hz, 1H), 6.43 (d, J=2 Hz, 1H), 5.32-5.28 (bs, 1H), 3.5-3.43 (m, 1H), 2.97-2.88 (m, 2H), 2.84-2.64 (m, 3H), 2.24-2.12 (m, 2H), 1.48-1.37 (m, 2H), 1.33-1.24 (m, 1H). (TLC dichloromethane/MeOH/7N NH$_3$/MeOH (960/35/5)) R$_f$ 0.09).

Compound 20 (0.54 g, 2.4 mmol), 0.76 g ammonium formate (12 mmol) and 20% Pd(OH)$_2$/C (54 mg) were combined in MeOH (50 ml) and warmed to reflux for 2 hours. The mixture was cooled, filtered, concentrated and re-dissolved in MeOH, followed by subsequent filtration over 5 g SCX-2 (MeOH followed by 1 N NH$_3$/MeOH). Purification by flash chromatography (dichloromethane/MeOH/7N NH$_3$/MeOH (960/35/5)) afforded compound 21 as a solid (0.25 g, 46%). mp 190° C. $^1$H-NMR (400 MHz, CDCl$_3$): δ 11.65 (bs, 1H), 8.21 (dd, J=5 Hz, 2 Hz, 1H), 7.88 (dd, J=8 Hz, 2 Hz, 1H), 7.06 (dd, J=8 Hz, 5 Hz, 1H), 6.34 (s, 1H), 3.46-3.37 (m, 1H), 3.29-3.20 (m, 2H), 3.03-2.93 (m, 3H), 2.91-2.80 (m, 1H), 2.27-2.21 (m, 1H), 1.90-1.78 (m, 2H), 1.70-1.60 (m, 1H), 1.43-1.33 (m, 1H).

1-Benzyl-3-(1H-pyrrolo[2,3-b]pyridin-2-yl)-piperidin-3-ol. (compound 23)

LDA (2.0 M in THF/heptane) (28 ml, 56 mmol) was added to 200 ml anhydrous THF at −10° C. under N$_2$. A solution of anhydrous THF (20 ml) containing compound 17 (14.54 g, 56 mmol) was added dropwise. After the addition, the resulting solution was stirred for 30 minutes at −10° C.-0° C. Then the temperature was lowered to −70° C. At this temperature, a solution of 2 (11.5 g, 60.8 mmol) in 25 ml THF was added dropwise (10 minutes). The free base of the HCl salt of commercially available 1-benzyl-piperidin-3-one (2) was obtained after filtration over SCX-2 (MeOH followed by 1 N NH$_3$/MeOH) and subsequent evaporation. After the addition of 2, the temperature was raised to −35° C.-30° C. and the resulting solution was stirred for 2 hours. The mixture was allowed to warm to ambient temperature and poured into a NH$_4$Cl solution (10 g/50 ml H$_2$O). Ethyl acetate was added and the organic layer was washed met a 5% NaHCO$_3$ solution, dried (Na$_2$SO$_4$), filtered and concentrated in vacuo. The resulting residue was purified by flash chromatography (diethyl ether/PA gradient 1:2 to pure diethyl ether) to give compound 22 as an oil (5.8 g, 23%). $^1$H-NMR (400 MHz, CDCl$_3$): δ 8.31 (dd, J=5 Hz, 2 Hz, 1H), 8.10-8.05 (m, 2H), 7.55 (dd, J=8 Hz, 2 Hz, 1H), 7.51-7.45 (m, 1H), 7.41-7.24 (m, 7H), 7.09 (dd, J=5 Hz, 8 Hz, 1H), 6.80 (s, 1H), 4.97-4.86 (bs, 1H), 3.69 and 3.59 (2×d, J gem=13 Hz, 2H), 3.12-2.87 (m, 2H), 2.58-2.38 (m, 2H), 2.14-2.04 (m, 1H), 1.96-1.83 (m, 1H), 1.68-1.44 (m, 2H). (TLC diethyl ether R$_f$ 0.2).

Compound 22 (1.49 g, 3.3 mmol) and 3.1 ml 2N NaOH were combined in MeOH (31 ml) and warmed to reflux for 2 hours. The mixture was cooled and concentrated. Ethyl acetate was added and the organic layer was washed met a 5% NaHCO$_3$ solution, dried (Na$_2$SO$_4$), filtered and concentrated in vacuo. The resulting residue was purified by flash chromatography (ethyl acetate) to give the title compound (23) as a solid. Recrystallization from ethyl acetate/diisopropylether. Yield 0.68 g, 66.5%. mp 122-126° C. $^1$H-NMR (400 MHz, CDCl$_3$): δ 10.9 (bs, 1H), 8.26 (dd, J=5 Hz, 2 Hz, 1H), 7.84 (dd, J=8 Hz, 2 Hz, 1H), 7.34-7.22 (m, 5H) 7.02 (dd, J=5 Hz, 8 Hz, 1H), 6.28 (d, J=2 Hz, 1H), 3.98-3.86 (bs, 1H),3.59 (dd, J gem=13 Hz, 2H), 2.93-2.83 (m, 2H), 2.45-2.39 (m, 1H), 2.25-1.95 (m, 1H), 2.04-1.80 (m, 3H), 1.75-1.66 (m, 1H) (TLC diethyl ether R$_f$ 0.2).

3-(1H-Pyrrolo[2,3-b]pyridin-2-yl)-piperidin-3-ol. (compound 24)

Compound 23 (3.07 g, 10 mmol), 3.5 g ammonium formate (58.3 mmol) and 20% Pd(OH)$_2$/C (340 mg) were combined in MeOH (100 ml) and warmed to reflux for 1 hour. The mixture was cooled, filtered, concentrated and re-dissolved in MeOH. Filtration over 40 g SCX-2 (MeOH followed by 1 N NH$_3$/MeOH) and subsequent purification by flash chromatography (MeOH/triethylamine (90/3) afforded the title compound 24 (amorphous, 1.73 g, 80%). $^1$H-NMR (400 MHz, D$_6$DMSO): δ 11.4 (bs, 1H), 8.15 (dd, J=5 Hz, 2 Hz, 1H), 7.84 (dd, J=8 Hz, 2 Hz, 1H), 7.01 (dd, J=8 Hz, J=5 Hz, 1H), 6.32 (bs, 1H), 5.24-5.0 (bs, 1H), 2.99-2.85 (m, 3H), 2.63-2.56 (m, 1H), 2.12-2.02 (m, 1H), 1.97-1.75 (m, 2H), 1.51-1.42 (m, 1H). (TLC MeOH/triethylamine (97/3 R$_f$ 0.26).

2-Piperidin-3-yl-1H-pyrrolo[2,3-b]pyridine. (compound 26)

Compound 24 (1.73 g, 7.97 mmol) dissolved in 75 ml 6N HCl was heated to reflux for 18 hours. The mixture was cooled and concentrated. Crystallization from ethyl acetate/ EtOH. afforded compound 25 (1.99 g, 92% (as di-HCl salt)). mp>275° C. (decomposition). $^1$H-NMR (400 MHz, D$_6$DMSO): δ 12.75 (bs, 1H), 8.33 (dd, J=5 Hz, 2 Hz, 1H), 8.24 (dd, J=8 Hz, 2 Hz, 1H), 7.30 (dd, J=8 Hz, J=5 Hz, 1H), 6.89-6.85 (m, 1H), 6.42 (bs, 1H), 4.10-4.04 (m, 2H), 3.34-3.27 (m, 2H), 2.65-2.58 (m, 2H). (TLC MeOH/triethylamine (97/3 $R_f$ 0.25).

Compound 25 (1.71 g, 6.3 mmol) and 20% Pd(OH)$_2$/C (210 mg) were combined in 100 ml MeOH and hydrogenated at 50 psi for 1 hour. The mixture was filtered and concentrated. A subsequent filtration over 30 g SCX-2 (MeOH followed by 1 N NH$_3$/MeOH), afforded the title compound 26 (1.06 g, 84%) which was reacted with 1 equivalent of fumaric acid in EtOH and concentrated. Recrystallization from EtOH/ ethyl acetate afforded a solid (free base/fumaric acid (1:1)), mp>211° C. (decomposition).

$^1$H-NMR (400 MHz, D$_6$DMSO): δ 12.75 (bs, 1H), 8.33 (dd, J=5 Hz, 2 Hz, 1H), 8.24 (dd, J=8 Hz, 2 Hz, 1H), 7.30 (dd, J=8 Hz, J=5 Hz, 1H), 6.89-6.85 (m, 1H), 6.42 (bs, 1H), 4.10-4.04 (m, 2H), 3.34-3.27 (m, 2H), 2.65-2.58 (m, 2H). (TLC MeOH/triethylamine (97/3) $R_f$ 0.14).

Separation of the enantiopure isomers was achieved using a chiral column (Chiralpak AD 20 μm, 250×4.6, MeOH/ EtOH 1/1, 2 ml/min, δ=220 nm, $R_t$: 5.6 min (26A), ([α]$_D^{25}$+4 (c 1, toluene) and $R_t$: 8.3 min (26B), ([α]$_D^{25}$–4 (c 1, toluene).

2-(1H-Pyrrolo[2,3-b]pyridin-3-yl)-piperidine-1-carboxylic acid tert-butyl ester. (compound 27)

Compound 26 (8.3 g, 41.29 mmol) was converted to the title compound (27) by the method as described for compound 9. Yield 10.9 gr (36.21 mmol, 87.7%). mp 144-145° C. (TLC diethyl ether $R_f$ 0.20).

2-(1-Methyl-piperidin-3-yl)-1H-Pyrrolo[2,3-b]pyridine. (compound 28)

Compound 27 (0.54 g, 1.8 mmol) was dissolved in 5 ml anhydrous THF. The resulting solution was slowly added to a stirred solution of LiAlH$_4$ (0.2 g, 5.2 mmol) in 25 ml anhydrous THF (60° C. under N$_2$). After stirring for 1.5 hours, the mixture was cooled.

To the resulting mixture was added subsequently 0.2 ml H$_2$O, 0.4 ml 2N NaOH and 0.2 ml H$_2$O and warmed at 60° C. under N$_2$. The mixture was cooled, filtered and washed with MeOH, followed by subsequent filtration over 5 g SCX-2 (MeOH followed by 1 N NH$_3$/MeOH). Purification by flash chromatography (MeOH/triethylamine (97/3)) afforded the title compound 28 as a solid (0.32 g, 83%), which was reacted with 1 equivalent of fumaric acid in EtOH and concentrated. Recrystallization from EtOH/ethyl acetate afforded a solid (0.47 g, free base/fumaric acid (1:1)), mp>218° C. (decomposition). $^1$H-NMR (400 MHz, D$_6$DMSO): δ 11.58 (bs, 1H), 8.13 (dd, J=5 Hz, 2 Hz, 1H), 7.83 (dd, J=8 Hz, 2 Hz, 1H), 7.00 (dd, J=8 Hz, 5 Hz, 1H), 6.56 (s, 2H), 6.20 (bs, 1H), 3.36-3.30 (m, 1H), 3.18-3.04 (m, 2H), 2.56-2.50 (m, 1H), 2.47 (s, 3H), 2.41-2.32 (m, 1H), 2.11-2.03 (m, 1H), 1.86-1.67 (m, 2H), 1.58-1.45 (m, 1H).

2-Piperidin-3-yl-1H-pyrrolo[2,3-b]pyridine 7-oxide (compound 29B)

Compound 27 (5.95 g, 19.7 mmol) and 5 g meta-chloroperbenzoic acid (23.2 mmol) were combined in dimethoxyethane (60 ml) and stirred for 10 minutes at room temperature. The reaction was concentrated in vacuo. The resulting residue was taken up in ethyl acetate, washed with 2N NaOH, dried (Na$_2$SO$_4$), filtered and concentrated in vacuo. The mixture was concentrated on SiO$_2$ and purified by flash chromatography (ethyl acetate/MeOH/triethylamine (90/10/1) to afford compound 29A (amorphous, 5.48 g, 87.5%). LCMS; $R_t$: 1.50 min, ([M+H]$^+$=318), (TLC MeOH/ethyl acetate/triethylamine (10/90/1 $R_f$ 0.46).

Compound 29A (0.44 g, 1.38 mmol) was converted to the title compound (29B) by the method as described for compound 10B. The title compound (298, as HCl salt) was obtained as a solid (0.33 g, 95%). mp>245° C. (decomposition). LCMS; $R_t$: 0.63 min, ([M+H]$^+$=218), $^1$H-NMR (400 MHz, D$_2$O): δ N$_1$—H was invisible, 8.20-8.16 (m, 1H), 8.10-8.05 (m, 1H), 7.25-7.20 (m,1H), 6.53 (bs, 1H), 3.64-3.57 (m, 1H), 3.40-3.33 (m, 1H), 3.31-3.22 (m, 1H), 3.10 (bt, J=10 Hz, 1H), 2.99-2.90 (m, 1H), 2.19-2.12 (m, 1H), 2.01-1.94 (m, 1H), 1.85-1.66 (m, 2H).

6-Chloro-2-piperidin-3-yl-1H-pyrrolo[2,3-b]pyridine (compound 32) and 4-Chloro-2-piperidin-3-yl-1H-pyrrolo[2,3-b]pyridine. (compound 33)

Compound 29A (4.87 g, 15.36 mmol) and 3.4 ml 1,1,1,3,3,3-hexamethyldisilazane (16.30 mmol) were combined in 100 ml THF. To this solution was added 3.2 ml (41.4 mmol) methyl chloroformate and the reaction mixture was stirred for 1.5 hours at reflux. The reaction was cooled and concentrated in vacuo. The resulting residue was taken up in ethyl acetate, washed with a 5% NaHCO$_3$ solution followed by brine, dried (Na$_2$SO$_4$), filtered and concentrated in vacuo. Purification by flash chromatography (diethyl ether/PA: 1/2, followed by ether) afforded compound 30A (amorphous, 2.08 g, 34.4%). (TLC diethyl ether/PE (1/1) $R_f$ 0.17). The second compound obtained during this chromatography (31A) was obtained as an oil (2.7 g, 44.6%) (TLC diethyl ether/PE (1/1) $R_f$ 0.08).

The basic cleavage of the N1-carbamate group was according to the method described for compound 12. Thus, compound 30A (2.08 g, 5.29 mmol) was dissolved in 75 ml MeOH containing 20 ml 2N NaOH and stirred for 18 hours at room temperature. The reaction mixture was concentrated in vacuo. The resulting residue was taken up in dichloromethane, washed with a 5% NaHCO$_3$ solution followed by brine, dried (Na$_2$SO$_4$), filtered and concentrated in vacuo. Purification by flash chromatography (diethyl ether/PE: 1/1) afforded compound 30B (amorphous, 1.74 g, 98%). (TLC diethyl ether/PE (1/1) $R_f$ 0.21). LCMS; $R_t$: 2.33 min, ([M+H]$^+$=336).

Compound 31A (0.35 g, 0.89 mmol) was dissolved in 8 ml MeOH containing 2 ml 2N NaOH and stirred for 18 hours at room temperature. The reaction was concentrated in vacuo. The resulting residue was taken up in dichloromethane, washed with a 5% NaHCO$_3$ solution followed by brine, dried (Na$_2$SO$_4$), filtered and concentrated in vacuo. Repeated purification by flash chromatography (diethyl ether/PE: 1/1) afforded compound 31B (amorphous, 0.1 g, 33%). (TLC diethyl ether $R_f$ 0.3). LCMS; $R_t$: 2.27 min, ([M+H]$^+$=336).

2 ml acetylchloride was slowly added to 40 ml of EtOH (−10° C.). After 15 minutes, this solution was added to compound 30B (1.67 g, 5 mmol) and heated to reflux for 1.5 hour. The mixture was cooled and partly concentrated, ethyl acetate was added and the resulting precipitate was collected by filtration and washed with diisopropylether.

The title compound, 6-chloro-2-piperidin-3-yl-1H-pyrrolo [2,3-b]pyridine 32 (as HCl salt) was obtained as a solid (1.29 g, 100%). mp>290° C. (decomposition). 1H-NMR (400 MHz, D6DMSO): δ 12.0 (bs, 1H), 7.93 (d, J=8 Hz, 1H), 7.08 (d, J=8 Hz, 1H), 6.31 (d, J=2 Hz, 1H), 3.58-3.49 (m, 1H), 3.34-3.24 (m, 2H), 3.15-3.02 (m, 1H), 2.92-2.79 (m, 1H), 2.18-2.10 (m, 1H), 1.94-1.80 (m, 2H), 1.78-1.64 (m, 1H).

Separation of the enantiopure isomers was achieved using a chiral column (Chiralpak AD-H 5 um, 250×4.6, 100%

EtOH+0.1% diethylamine, 0.5 ml/min, δ=220 nm, R$_t$: 18.4 min (32A), ([α]$_D^{25}$−10 (c 1, toluene) and R$_t$: 25.2 min (32B), ([α]$_D^{25}$+10 (c 1, toluene).

Both isomers were reacted with 1 equivalent of fumaric acid in EtOH and concentrated. Recrystallization from EtOH/ethyl acetate afforded a solid (free base/fumaric acid (1:1)), mp>206° C. (decomposition).

0.22 ml acetylchloride was slowly added to 5 ml of EtOH (−10° C.). After 15 minutes, this solution was added to compound 31B (0.1 g, 0.3 mmol) and heated to reflux for 1.5 hour. The mixture was cooled and partly concentrated, ethyl acetate was added and the resulting precipitate was collected by filtration and washed with diisopropylether to afford compound 33: 4-Chloro-2-piperidin-3-yl-1H-pyrrolo[2,3-b]pyridine (as HCl salt), (52 mg, 64%). mp>250° C. (decomposition). $^1$H-NMR (400 MHz, D$_2$O): δ N$_1$—H was invisible, 8.30 (bd, J=8 Hz, 1H), 7.39 (bd, J=8 Hz, 1H), 6.63 (bs, 1H), 3.66-3.58 (m, 1H), 3.42-3.23 (m, 2H), 3.16-3.06 (m, 1H), 3.0-2.90 (m, 1H), 2.23-2.14 (m, 1H), 2.04-1.92 (m, 1H), 1.86-1.67 (m, 2H).

(R)-2-Pyrrolidin-2-ylmethyl-1H-pyrrolo[2,3-b]pyridine. (compound 39A) and (S)-2-Pyrrolidin-2-ylmethyl-1H-pyrrolo[2,3-b]pyridine. (compound 39B)

To a solution of anhydrous THF (75 ml) containing compound 17 (6.2 g, 24 mmol) was added 12 ml (24 mmol) LDA (2.0 M in THF/heptane) dropwise at −10° C. under N$_2$. After the addition, the resulting solution was stirred for 30 minutes at −10° C.-0° C. Then the temperature was lowered to −70° C. At this temperature, a solution of 35 (4 g, 24.5 mmol) in 25 ml THF was added dropwise (10 minutes). After the addition of 35, the temperature was raised to −20° C. and the resulting solution was stirred for 2 hours. The mixture was allowed to warm to ambient temperature and stirred for another 2 hours.

The reaction mixture was concentrated and the residue was dissolved in 40 ml 1N HCl, 40 ml EtOH and 40 ml THF. The mixture was stirred at 80° C. for 18 hours. The reaction mixture was concentrated in vacuo. The resulting residue was taken up in ethyl acetate, washed with 2N NaOH, dried (Na$_2$SO$_4$), filtered and concentrated in vacuo. Purification by flash chromatography (MeOH/triethylamine 97/3) afforded compound 38A (amorphous, 3.63 g, 44%). $^1$H-NMR (400 MHz, CDCl$_3$): δ 8.35 (bd, J=5 Hz, 1H), 8.09 (bd, J=8 Hz, 2H), 7.67 (bd, J=8 Hz, 1H), 7.57-7.41 (m, 3H), 7.12 (dd, J=8 Hz, 5 Hz, 1H), 6.46 (s, 1H), 3.70-3.58 (m, 1H), 3.39-3.31 (m, 1H), 3.23-3.15 (m, 1H), 3.13-3.03 (m, 1H), 2.98-2.86 (m, 1H), 2.10-1.70 (m, 3H), 1.57-1.44 (m, 1H). (TLC MeOH/triethylamine 97/3 R$_f$ 0.18). LCMS; R$_t$: 1.27 min, ([M+H]$^+$=342).

Compound 38A (3.63 g, 10.6 mmol), 11 g KOH and 22 ml hydrazine monohydrate were combined in 2-(2-hydroxyethoxy)-ethanol (100 ml) and stirred 1 hour at 100° C. To the cooled reaction was added ethyl acetate and the resulting organic layer was washed with 2N NaOH, dried (Na$_2$SO$_4$), filtered and concentrated in vacuo. The mixture was dissolved in MeOH and filtrated over 40 g SCX-2 (MeOH followed by 1 N NH$_3$/MeOH). Subsequent purification by flash chromatography (MeOH/triethylamine (98/2) afforded the title compound 39A. LCMS; R$_t$: 0.91 min, ([M+H]$^+$=202). (amorphous, 1.42 g, 66%). ([α]$_D^{25}$−50 (c 1, toluene), which was reacted with 1 equivalent of fumaric acid in EtOH and concentrated. Recrystallization from EtOH/ethyl acetate afforded a solid (free base/fumaric acid (1:1)), mp>163° C. (decomposition). $^1$H-NMR (400 MHz, D$_6$DMSO): δ 11.7 (bs, 1H), 8.13 (dd, J=5 Hz, 2 Hz, 1H), 7.84 (dd, J=8 Hz, 2 Hz, 1H), 7.0 (dd, J=8 Hz, 5 Hz, 1H), 6.51 (s, 2H), 6.32 (s, 1H), 3.85-3.77 (m, 1H), 3.26-3.04 (m, 4H), 2.09-1.80 (m, 3H), 1.71-1.61 (m, 1H).

(S)-2-Pyrrolidin-2-ylmethyl-1H-pyrrolo[2,3-b]pyridine (compound 39B) was obtained using the methodology described for compound 39A, by using the sulphamidate 36. ([α]$_D^{25}$+50 (c 1, toluene).

(R)-2-(1-Methyl-pyrrolidin-2-ylmethyl)-1H-pyrrolo[2,3-b]pyridine. (compound 41A) and (S)-2-(1-Methyl-pyrrolidin-2-ylmethyl)-1H-pyrrolo[2,3-b]pyridine. (compound 41B)

Compound 38A (0.39 g, 1.14 mmol), 0.5 g NaBH(OAc)$_3$ and 0.2 ml formaldehyde (37%) were combined in dichloroethane (15 ml) and stirred 1 hour at room temperature. The reaction was concentrated in vacuo. The resulting residue was taken up in ethyl acetate, washed with 2N NaOH, dried (Na$_2$SO$_4$), filtered and concentrated in vacuo which afforded 40A (amorphous, 0.40 g, 98%), $^1$H-NMR (400 MHz, CDCl$_3$): δ 8.35 (dd, J=5 Hz, 2 Hz, 1H), 8.12-8.07 (m, 2H), 7.69 (dd, J=8 Hz, 2 Hz, 1H), 7.56-7.41 (m, 3H), 7.12 (dd, J=8 Hz, 5 Hz, 1H), 6.40 (s, 1H), 3.73-3.67 (m, 1H), 3.16-3.10 (m, 1H), 2.87-2.73 (m, 2H), 2.47 (s, 3H), 2.33-2.25 (m, 1H), 1.95-1.50 (m, 4H).

Compound 40A (0.4 g, 11.2 mmol), 1.1 g KOH and 2.2 ml hydrazine monohydrate were combined in 2-(2-hydroxyethoxy)-ethanol (10 ml) and stirred 1 hour at 100° C. To the cooled reaction was added ethyl acetate and the resulting organic layer was washed with 2N NaOH, dried (Na$_2$SO$_4$), filtered and concentrated in vacuo. The mixture was dissolved in MeOH and filtrated over 40 g SCX-2 (MeOH followed by 1 N NH$_3$/MeOH). Subsequent purification by flash chromatography (MeOH/triethylamine (99/1) afforded the title compound 41A (solid, 0.19 g, 76%). ([α]$_D^{25}$+44 (c 1, toluene).

$^1$H-NMR (400 MHz, CDCl$_3$): δ 10.4 (bs, 1H), 8.18 (dd, J=5 Hz, 2 Hz, 1H), 7.79 (dd, J=8 Hz, 2 Hz, 1H), 6.99 (dd, J=8 Hz, 5 Hz, 1H), 6.18 (bs, 1H), 3.18-3.07 (m, 2H), 2.90-2.83 (m, 1H), 2.61-2.53 (m, 1H), 2.45 (s, 3H), 2.25-2.17 (m, 1H), 1.89-1.79 (m, 1H), 1.69-1.43 (m, 3H).

(S)-2-(1-Methyl-pyrrolidin-2-ylmethyl)-1H-pyrrolo[2,3-b]pyridine. (compound 41B) was obtained using the methodology described for compound 41A. ([α]$_D^{25}$−42 (a 1, toluene). mp 130-131° C., (R)-6-Chloro-2-pyrrolidin-2-ylmethyl-1H-pyrrolo[2,3-b]pyridine. (compound 45A) and (S)-6-Chloro-2-pyrrolidin-2-ylmethyl-1H-pyrrolo[2,3-b]pyridine. (compound 45B)

6-Chloro-7-azaindole (9.3 g, 61.1 mmol), prepared as described (*Synthesis*, 1992), was dissolved in 100 ml anhydrous THF under N$_2$. At 0° C., a 60% dispersion of NaH 3.5 g (65.9 mmol) in mineral oil was added. After stirring for 1 hour at room temperature, the mixture was cooled (0° C.) and 8.7 ml (67.2 mmol) benzenesulfonyl chloride dissolved in 20 ml anhydrous THF was added. The reaction mixture was stirred at room temperature for 1 hour. Ethyl acetate was added to the mixture and the organic layer was washed three times with a saturated NaHCO$_3$ solution, dried (Na$_2$SO$_4$), filtered and concentrated. The resulting residue was purified by flash chromatography (diethyl ether/PE gradient (1:4 to pure diethyl ether) to give 1-benzenesulfonyl-6-chloro-1H-pyrrolo[2,3-b]pyridine (amorphous, 14.4 g, 80.7%) (TLC diethyl ether/PE (1/1) R$_f$ 0.37). LCMS; R$_t$: 1.98 min, ([M+H]$^+$=293).

To a solution of anhydrous THF (100 ml) containing compound 1-benzenesulfonyl-6-chloro-1H-pyrrolo[2,3-b]pyridine (2.52 g, 8.6 mmol) was added 4.3 ml (24 mmol) LDA (2.0 M in THF/heptane) dropwise at −78° C. under $N_2$. After the addition, the resulting solution was stirred for 60 minutes at −78° C. At this temperature, a solution of 35 (1.4 g, 8.6 mmol) in 10 ml THF was added dropwise (5 minutes). After the addition of 35, the temperature was raised to −20° C. and the resulting solution was stirred for 2 hours. The mixture was allowed to warm to ambient temperature and stirred for another 2 hours.

The reaction mixture was concentrated and the residue was dissolved in 40 ml 1N HCl, 40 ml EtOH and 40 ml THF. The mixture was stirred at 80° C. for 18 hours. The reaction mixture was concentrated in vacuo. The resulting residue was taken up in ethyl acetate, washed with 2N NaOH, dried ($Na_2SO_4$), filtered and concentrated in vacuo. Purification by flash chromatography (MeOH/triethylamine 98/2) afforded (R)-1-benzenesulfonyl-6-chloro-2-pyrrolidin-2-ylmethyl-1H-pyrrolo[2,3-b]pyridine (amorphous, 1.01 g, 31%) (TLC MeOH/triethylamine 98/2 $R_f$ 0.32).

(R)-1-Benzenesulfonyl-6-chloro-2-pyrrolidin-2-ylmethyl-1H-pyrrolo[2,3-b]pyridine (1.01 g, 2.69 mmol), 20 ml 2N NaOH and 30 ml isopropanol were combined and stirred 3 hours at 100° C. To the cooled reaction was added ethyl acetate and the resulting organic layer was washed with 2N NaOH, dried ($Na_2SO_4$), filtered and concentrated in vacuo. The mixture was dissolved in MeOH and filtrated over 10 g SCX-2 (MeOH followed by 1 N $NH_3$/MeOH). Subsequent purification by flash chromatography (MeOH/triethylamine (98/2) afforded the title compound 45A (solid, 366 mg, 58%). ($[α]_D^{25}$−48 (c 1, toluene). $^1$H-NMR (400 MHz, CDCl$_3$): δ 11.0-10.0 (bs, 1H), 7.52 (d, J=8 Hz, 1H), 7.01 (d, J=8 Hz, 1H), 6.16 (s, 1H), 3.50-3.42 (m, 1H), 3.02-2.90 (m, 3H), 2.81-2.73 (m, 1H), 1.95-1.85 (m, 1H), 1.82-1.64 (m, 2H), 1.43-1.33 (m, 1H). Compound 45 A was reacted with 1 equivalent of fumaric acid in EtOH and concentrated. Recrystallization from EtOH/ethyl acetate afforded a solid (free base/fumaric acid (2:1)), mp>222° C. (decomposition).

(S)-6-Chloro-2-pyrrolidin-2-ylmethyl-1H-pyrrolo[2,3-b]pyridine (compound 45B) was obtained (from 36) using the methodology described for compound 45A. ($[α]_D^{25}$+44 (c 1, toluene). Compound 45B was reacted with 1 equivalent of fumaric acid in EtOH and concentrated. Recrystallization from EtOH/ethyl acetate afforded a solid (free base/fumaric acid (1:1)), mp 189-190° C.

(R)-6-Bromo-2-pyrrolidin-2-ylmethyl-1H-pyrrolo[2,3-b]pyridine. (compound 46A) and (S)-6-Bromo-2-pyrrolidin-2-ylmethyl-1H-pyrrolo[2,3-b]pyridine. (compound 46B)

6-Bromo-7-azaindole (4.65 g, 23.6 mmol), prepared as described (Synthesis, 1992), was converted to 1-benzenesulfonyl-6-bromo-1H-pyrrolo[2,3-b]pyridine using the methodology described above.(solid, mp 121-124° C.). (7.57 g, 95%)

$^1$H-NMR (400 MHz, CDCl$_3$): δ 8.28-8.22 (m, 2H), 7.70-7.50 (m, 5H), 7.32 (d, J=8 Hz, 1H), 6.56 (d, J=4 Hz, 1H). (TLC diethyl ether $R_f$ 0.55).

1-Benzenesulfonyl-6-bromo-1H-pyrrolo[2,3-b]pyridine (2.07 g, 6.1 mmol) was converted to (R)-1-benzenesulfonyl-6-bromo-2-pyrrolidin-2-ylmethyl-1H-pyrrolo[2,3-b]pyridine using the methodology described above (amorphous, 1.24 g, 48%) $^1$H-NMR (400 MHz, CDCl$_3$): δ 8.21-7.97 (m, 2H), 7.61-7.47 (m, 5H), 7.25 (d, J=8 Hz, 1H), 6.46 (s, 1H), 3.65-3.57 (m, 1H), 3.37-3.31 (m, 1H), 3.09-3.03 (m, 1H), 2.96-2.89 (m, 1H), 2.06-1.73 (m, 3H), 1.54-1.45 (m, 1H). (TLC MeOH/triethylamine 97/3 $R_f$ 0.22).

(R)-1-Benzenesulfonyl-6-bromo-2-pyrrolidin-2-ylmethyl-1H-pyrrolo[2,3-b]pyridine (1.24 g, 2.95 mmol), 30 ml 2N NaOH and 50 ml MeOH were combined and stirred for 30 minutes hours at 60° C. To the cooled reaction was added ethyl acetate and the resulting organic layer was washed with 2N NaOH, dried ($Na_2SO_4$), filtered and concentrated in vacuo. The mixture was dissolved in MeOH and filtrated over 10 g SCX-2 (MeOH followed by 1 N $NH_3$/MeOH). Subsequent purification by flash chromatography (MeOH/triethylamine (97/3) afforded the title compound 46A (amorphous, 630 mg, 76%). ($[α]_D^{25}$−50 (c 1, toluene), which was converted to its salt (free base/fumaric acid (1:1)), $^1$H-NMR (400 MHz, D$_6$DMSO): δ $N_1$—H invisible, 7.82 (d, J=8 Hz, 1H), 7.18 (d, J=8 Hz, 1H), 6.49 (s, 2H), 6.38 (s, 1H), 3.82-3.72 (m, 1H), 3.27-3.05 (m, 4H), 2.09-1.80 (m, 3H), 1.70-1.60 (m, 1H).

(S)-6-Bromo-2-pyrrolidin-2-ylmethyl-1H-pyrrolo[2,3-b]pyridine (compound 46B) was obtained (from 36) using the methodology described for compound 46A. ($[α]_D^{25}$+50 (c 1, toluene).

(R)-6-Fluoro-2-pyrrolidin-2-ylmethyl-1H-pyrrolo[2,3-b]pyridine. (compound 47A) and (S)-6-Fluoro-2-pyrrolidin-2-ylmethyl-1H-pyrrolo[2,3-b]pyridine. (compound 47B)

Compound 55 (18 g, 161 mmol), 70 g $K_2CO_3$ (506 mmol) and 15.4 ml (161 mmol) ethyl-chloroformate were combined in $CH_3CN$ (400 ml) and stirred for 4 days at 40° C. TLC showed a moderate conversion. An additional 15.4 ml ethyl-chloroformate was added and stirring was continued for 2 days. The mixture was cooled. Ethyl acetate was added to the mixture and the organic layer was washed with a saturated $NaHCO_3$ solution, dried ($Na_2SO_4$), filtered and concentrated. The resulting residue was purified by flash chromatography (diethyl ether/PE (1:3)) and afforded (6-fluoro-pyridin-2yl)-carbamic acid ethyl ester (56) (amorphous, 19.68 g, 66.5%). $^1$H-NMR (400 MHz, CDCl$_3$): δ 7.83 (dd, J=8 Hz, 2 Hz, 1H), 7.80-7.73 (m, 1H), 7.50-7.40 (bs, 1H), 6.61-6.57 (m, 1H), 4.25 (q, J=8 Hz, 2H), 1.32 (t, J=8 Hz, 3H). (TLC diethyl ether/PE 1/1 $R_f$ 0.5).

28.6 ml (0.18 mol) TMEDA was added to a solution of compound 56 (13.41 g, 72.9 mmol) dissolved in 300 ml anhydrous THF. The mixture was cooled to −78° C. (under $N_2$). To the stirred reaction mixture was added 76 ml (2.5 M n-BuLi) and the mixture was stirred for 2 hours at −78° C. After the addition of $I_2$(48 g, 0.17 mol), the mixture was stirred for 1 hour at −78° C. The reaction mixture was subsequently quenched with a saturated $Na_2S_2O_3$ solution and allowed to warm to ambient temperature. Ethyl acetate was added to the mixture and the organic layer was washed with a saturated $NaHCO_3$ solution, dried ($Na_2SO_4$), filtered and concentrated. The resulting residue was purified by flash chromatography (diethyl ether/PE (1/3) to 1/1) and afforded (6-fluoro-3-iodo-pyridin-2yl)-carbamic acid ethyl ester (57) (amorphous, 15.86 g, 70%). $^1$H-NMR (400 MHz, CDCl$_3$): δ 8.07 (bt, J=8 Hz, 1H), 7.24-7.14 (bs, 1H), 6.49 (dd, J=8 Hz, 3 Hz, 1H), 4.29 (q, J=8 Hz, 2H), 1.35 (t, J=8 Hz, 3H). (TLC diethyl ether/PE 1/1 $R_f$ 0.27).

A mixture of compound 57 (4 g, 12.9 mmol), 3.3 ml (23.4 mmol) TMSA (ethynyl-trimethyl-silane), 246 mg (1.29 mmol) Cu(I)iodide, 454 mg (0.65 mmol) PdCl$_2$(PPh$_3$)$_2$ (454 mg, 0.64 mmol) and triethylamine (6.3 ml) was stirred and degassed ($N_2$). The resulting reaction mixture was stirred for 10 hours at 100° C. (closed vessel), cooled and poured into ethyl acetate and H$_2$O. The organic layer was washed with H$_2$O, dried (Na$_2$SO$_4$), filtered and concentrated. The residue was purified by flash chromatography (diethyl ether/PE (1/3)) to afford (6-fluoro-3-trimethylsilanylethynyl-pyridin-2yl)-carbamic acid ethyl ester (58) (oil, 1.5 g, 42%). $^1$H-NMR (200 MHz, CDCl$_3$) δ 7.76 (bt, J=8 Hz, 1H), 7.68-7.60 (bs, 1H), 6.56 (dd, J=8 Hz, 3 Hz, 1H), 4.29 (q, J=8 Hz, 2H), 1.34 (t, J=8 Hz, 3H), 0.3 (s, 9H). (TLC diethyl ether/PE 1/1 R$_f$ 0.39).

A mixture of compound 58 (6 g, 21.4 mmol) and 8.2 g (43 mmol) Cu(I)iodide were dissolved in 100 ml DMF and degassed for 0.5 hour. The reaction mixture was stirred at 150° C. (preheated oil bath) for 30 minutes. The mixture was cooled and diluted with ethyl acetate and filtered. The residue was washed with H$_2$O, dried (Na$_2$SO$_4$), filtered and concentrated. Subsequent purification by flash chromatography (diethyl ether/PE (1/1)) yielded compound 59 (amorphous, 2.58 g, 12.4 mmol, 57.9%), $^1$H-NMR (200 MHz, CDCl$_3$): δ 7.95 (bt, J=8 Hz, 1H), 7.69 (d, J=4 Hz, 1H), 6.87 (dd, J=8 Hz, 2 Hz, 1H), 6.57 (d, J=4 Hz, 1H), 4.55 (q, J=8 Hz, 2H), 1.49 (t, J=8 Hz, 3H). (TLC diethyl ether/PE 1/1 R$_f$ 0.42).

Compound 59 (2.58 g, 12.4 mmol) was dissolved in 50 ml MeOH and 20 ml 2 N NaOH. The reaction mixture was stirred for 30 minutes at room temperature. Ethyl acetate was added to the mixture and the organic layer was washed with a 5% aqueous NaHCO$_3$ solution, dried (Na$_2$SO$_4$), filtered and concentrated to afford 6-fluoro-1H-pyrrolo[2,3-b]pyridine (6-fluoro-7-azaindole, compound 44) as a semi solid (1.68 g, 12.3 mmol, 99%). $^1$H-NMR (400 MHz, CDCl$_3$): δ 9.6 (bs, 1H), 7.95 (bt, J=8 Hz, 1H), 7.31-7.27 (m, 1H), 6.75 (dd, J=8 Hz, 2 Hz, 1H), 6.55-6.50 (m, 1H). (TLC diethyl ether/PE (1/1) R$_f$ 0.34). LCMS; R$_t$: 1.39 min, ([M+H]$^+$=137).

6-Fluoro-7-azaindole (compound 44, 1.72 g, 12.6 mmol) was reacted with benzene-sulfonyl chloride as described for the synthesis of 45A/B to give 1-benzenesulfonyl-6-fluoro-1H-pyrrolo[2,3-b]pyridine (compound 60), (solid, 3.03 g, 86.6%) mp 130-132° C. (TLC diethyl ether/PE (1/1) R$_f$ 0.29). LCMS; R$_t$: 1.79 min, ([M+H]$^+$=277).

1-Benzenesulfonyl-6-fluoro-1H-pyrrolo[2,3-b]pyridine (0.8 g, 2.9 mmol) was converted to (R)-1-benzenesulfonyl-6-fluoro-2-pyrrolidin-2-ylmethyl-1H-pyrrolo[2,3-b]pyridine using the methodology as described for 45A/B (amorphous, 0.31 g, 30%). (TLC MeOH/triethylamine (97/3) R$_f$ 0.28).

(R)-1-Benzenesulfonyl-6-fluoro-2-pyrrolidin-2-ylmethyl-1H-pyrrolo[2,3-b]pyridine (0.26 g, 0.72 mmol) was converted to (R)-6-fluoro-2-pyrrolidin-2-ylmethyl-1H-pyrrolo[2,3-b]pyridine (compound 47A, 90 mg, 57%) using the conditions described for 45A/B.

The title compound 47A (amorphous), $[α]_D^{25}$ -38 (c 1, toluene), was converted to its (amorphous) salt (free base/fumaric acid (1:1)), $^1$H-NMR (400 MHz, D$_6$DMSO): δ 12.2-11.7 (bs, 1H), 8.0 (bt, J=8 Hz, 1H), 6.76 (bd, J=8 Hz, 1H), 6.51 (s, 2H), 6.37 (s, 1H), 3.83-3.74 (m, 1H), 3.26-3.03 (m, 4H), 2.10-1.79 (m, 3H), 1.71-1.61 (m, 1H). (TLC MeOH/triethylamine (97/3) R$_f$ 0.22).

(S)-6-Fluoro-2-pyrrolidin-2-ylmethyl-1H-pyrrolo[2,3-b]pyridine (compound 47B) was obtained (from 36) using the methodology described for compound 47A. $[α]_D^{25}$ +38 (c 1, toluene).

(R)-6-Methoxy-2-pyrrolidin-2-ylmethyl-1H-pyrrolo[2,3-b]pyridine. (compound 49)

(R)-6-Bromo-2-pyrrolidin-2-ylmethyl-1H-pyrrolo[2,3-b]pyridine. (46A, 0.67 g, 2.39 mmol) was converted to the Pyrrolidine (Boc protected) analog 48 (amorphous, 0.72 g, 79% overall), using the methodology described for compound 9.

$^1$H-NMR (400 MHz, CDCl$_3$): δ 9.4 (bs, 1H), 7.66 (bd, J=8 Hz, 1H), 7.18 (bd, J=8 Hz, 1H), 6.19 (bs, 1H), 4.10-4.03 (m, 1H), 3.42-3.25 (m, 2H), 3.16-3.07 (m, 1H), 3.04-2.88 (m, 1H), 2.0-1.89 (m, 1H), 1.8-1.63 (m, 3H).

Compound 48 (0.34 g, 0.89 mmol) was dissolved in 4 ml DMF and 2.5 ml MeOH (under N$_2$). To this mixture was added 1.6 g (29.6 mmol) NaOMe and 0.25 g (1.74 mmol) Cu(I)Bromide and the mixture was stirred for 1 hour at room temperature. Ethyl acetate was added and the organic layer was washed met a 5% NaHCO$_3$ solution, dried (Na$_2$SO$_4$), filtered and concentrated in vacuo. The resulting residue was purified by flash chromatography (diethyl ether) to give the Pyrrolidine (Boc protected) precursor of 49 as an oil (0.32 g, 56%). (TLC diethyl ether R$_f$ 0.8). $^1$H-NMR (400 MHz, CDCl$_3$): δ 8.7 (bs, 1H), 7.68 (bd, J=8 Hz, 1H), 6.52 (bd, J=8 Hz, 1H), 6.1 (bs, 1H), 4.11-4.01 (m, 1H), 3.94 (s, 3H), 3.46-3.23 (m, 2H), 3.18-2.96 (m, 1H), 2.93-2.78 (m, 1H), 1.97-1.84 (m, 1H), 1.83-1.71 (m, 3H), 1.51 (s, 9H), which was deprotected (HCl/EtOH as described before) to generate the title compound (49) as a HCl salt (amorphous, hygroscopic). Yield 0.180 mg (80%), $[α]_D^{25}$ -12 (c 1, MeOH). LCMS; R$_t$: 1.17 min, ([M+H]$^+$=232). Compound 49 (free base obtained after filtration of the HCl salt over SCX-2), was converted to its salt (using the methodology described before) (free base/fumaric acid (1:1), amorphous), $^1$H-NMR (400 MHz, D$_6$DMSO): δ 11.61 (bs, 1H), 7.75 (d, J=8 Hz, 1H), 6.49 (s, 2H), 6.47 (d, J=8 Hz, 1H), 6.21 (s, 1H), 3.84 (s, 3H), 3.78-3.71 (m, 1H), 3.23-3.18 (m, 1H), 3.14-3.08 (m, 1H), 3.01-2.95 (m, 1H), 2.05-1.80 (m, 3H), 1.67-1.59 (m, 1H).

(R)-5-Bromo-2-pyrrolidin-2-ylmethyl-1H-pyrrolo[2,3-b]pyridine. (compound 52A) and (S)-5-Bromo-2-pyrrolidin-2-ylmethyl-1H-pyrrolo[2,3-b]pyridine. (compound 52B)

5-Bromo-7-azaindole (5.19 g, 26.3 mmol), commercially available, was converted to 1-benzenesulfonyl-5-bromo-1H-pyrrolo[2,3-b]pyridine using the methodology described for 45A/B. solid, mp 141-142° C. (6.9 g, 78%) $^1$H-NMR (400 MHz, CDCl$_3$): δ 8.45 (d, J=2 Hz, 1H), 8.19-8.15 (m, 2H), 7.98 (d, J=2 Hz, 1H), 7.74 (d, J=4 Hz, 1H), 7.62-7.47 (m, 3H), 6.55 (d, J=4 Hz, 1H). LCMS; R$_t$: 1.92 min, ([M+H]$^+$=337).

1-Benzenesulfonyl-5-bromo-1H-pyrrolo[2,3-b]pyridine (5.52 g, 16.3 mmol) was converted to (R)-1-benzenesulfonyl-5-bromo-2-pyrrolidin-2-ylmethyl-1H-pyrrolo[2,3-b]pyridine using the methodology described for 45A/B (amorphous, 3.02 g, mixture of compounds, containing approx. 70% of the anticipated C$_2$-regioisomer). (TLC MeOH/triethylamine (97/3) R$_f$ 0.3). LCMS; R$_t$: 1.44 min, ([M+H]$^+$= 420, 422).

The aforementioned mixture containing (R)-1-Benzenesulfonyl-5-bromo-2-pyrrolidin-2-ylmethyl-1H-pyrrolo[2,3-b]pyridine (3.02 g, approx. 7.1 mmol), was converted to the title compound 52A using the methodology described for 45A/B (repeated flash chromatography), (amorphous, 0.5 g, approx. 25%), which was converted to its salt (free base/fumaric acid (1:1)), $^1$H-NMR (400 MHz, D$_6$DMSO): δ N$_1$—H invisible, 8.16 (d, J=2 Hz, 1H), 8.06 (d, J=2 Hz, 1H), 6.46 (s, 2H), 6.30 (s, 1H), 3.80-3.72 (m, 1H), 3.23-3.03 (m, 4H), 2.06-117 (m, 3H), 1.67-1.57 (m, 1H).

(S)-5-Bromo-2-pyrrolidin-2-ylmethyl-1H-pyrrolo[2,3-b]pyridine (compound 52B) was obtained (from 36) using the methodology described for compound 52A. LCMS; R$_t$: 1.27 min, ([M+H]$^+$=280). $[α]_D^{25}$ +38 (c 1, toluene).

(R)-5-Methyl-2-pyrrolidin-2-ylmethyl-1H-pyrrolo[2,3-b]pyridine. (compound 53A)

5-Methyl-7-azaindole (4.15 g, 31.4 mmol), was converted to 1-benzenesulfonyl-5-methyl-1H-pyrrolo[2,3-b]pyridine using the methodology described for 45A/B (amorphous, 7.07 g, 82%). $^1$H-NMR (400 MHz, CDCl$_3$): δ 8.25 (bd, J=2 Hz, 1H), 8.19-8.15 (m, 2H), 7.66 (d, J=4 Hz, 1H), 7.62 (bd, J=2 Hz, 1H), 7.58-7.43 (m, 3H), 6.51 (d, J=2 Hz, 1H), 2.38 (s, 3H). (TLC diethyl ether R$_f$ 0.52). LCMS; R$_t$: 1.75 min, ([M+H]$^+$=273). 1-Benzenesulfonyl-5-methyl-1H-pyrrolo[2,3-b]pyridine (3.15 g, 11.5 mmol) was converted to (R)-1-benzenesulfonyl-5-methyl-2-pyrrolidin-2-ylmethyl-1H-pyrrolo[2,3-b]pyridine using the methodology described for 45A/B (amorphous, 7.04 g, 61%). LCMS; R$_t$: 1.41 min, ([M+H]$^+$=356).

(R)-1-Benzenesulfonyl-5-methyl-2-pyrrolidin-2-ylmethyl-1H-pyrrolo[2,3-b]pyridine (1.5 g, 4.22 mmol), 3.5 g KOH and I ml hydrazine monohydrate were combined in 2-(2-hydroxy-ethoxy)-ethanol (25 ml) and stirred 1 hour at 100° C. To the cooled reaction was added MeOH and the reaction mixture filtrated over 60 g SCX-2 (MeOH followed by 1 N NH$_3$/MeOH). Subsequent purification by flash chromatography (MeOH/triethylamine (90/2) afforded the title compound 53A (amorphous, 0.46 g, 50%). ([α]$_D^{25}$ –10 (c 1, dioxane), which was reacted with 1 equivalent of fumaric acid in MeOH and concentrated to afford the title compound 53A (amorphous) (free base/fumaric acid (1:1)). $^1$H-NMR (400 MHz, D$_6$DMSO): δ 11.6 (bs, 1H), 7.97 (bs, 1H), 7.63 (bs, 1H), 6.51 (s, 2H), 6.22 (s, 1H), 3.84-3.77 (m, 1H), 3.26-3.03 (m, 4H), 2.33 (s, 3H), 2.07-1.81 (m, 3H), 1.69-1.61 (m, 1H).

2-Pyrrolidin-3-ylmethyl-1H-pyrrolo[2,3-b]pyridine. (compound 66)

8.83 g (91 mmol) methoxymethylamine. (HCl salt) was stirred in 200 ml anhydrous benzene (0° C., under N$_2$). 46.2 ml trimethylaluminium/toluene (2.5M) was added and the mixture was stirred for 2.5 hours at 0° C. Compound 62 (6.73 g, 30.7 mmol) dissolved in 100 ml benzene was added and the resulting mixture was stirred for 1 hour at room temperature. To the mixture was added subsequently saturated NaHCO$_3$ (0° C.) and ethyl acetate. The organic layer was washed three times with a 5% NaHCO$_3$ solution, dried (Na$_2$SO$_4$), filtered and concentrated. The resulting residue was purified by flash chromatography (MeOH/ethyl acetate (1/9)) to give 1-benzyl-pyrrolidine-3-carboxylic acid methoxy-methyl-amide (compound 63, 6.76 g, 88.7%). $^1$H-NMR (400 MHz, CDCl$_3$): δ 7.38-7.22 (m, 5H), 3.69-3.62 (m, 5H), 3.45-3.35 (m, 1H), 3.19-3.18 (2×s, 3H), 3.06-2.99 (m, 1H), 2.88-2.81 (m, 1H), 2.56-2.41 (m, 2H), 2.14-2.03 (m, 2H).

To a solution of anhydrous THF (75 ml) containing compound 17 (7.2 g, 27.1 mmol) was added 13.6 ml LDA (2.0 M in THF/heptane) dropwise at –10° C. under N$_2$, After the addition, the resulting solution was stirred for 30 minutes at –10° C.-0° C. Then the temperature was lowered to –70° C. At this temperature, a solution of 63 (6.72 g, 27 mmol) in 25 ml THF was added dropwise (10 minutes). After the addition of 63, the temperature was raised to –30° C. (0.5 hour) and the resulting solution was stirred for 1 hour at –30° C. Then the mixture was quenched with a saturated NH$_4$Cl solution at –30° C. and allowed to warm to ambient temperature. Ethyl acetate was added and the organic layer was washed with 5% NaHCO$_3$, dried (Na$_2$SO$_4$), filtered and concentrated in vacuo. Purification by flash chromatography (diethyl ether followed by ethyl acetate) afforded compound 64 (amorphous, 5.38 g, 44.6%) LCMS; R$_t$: 1.27 min, ([M+H]$^+$=342).

Compound 64 (1.05 g, 2.35 mmol), 2 g KOH and 3.56 ml hydrazine monohydrate were combined in 2-(2-hydroxy-ethoxy)-ethanol (20 ml) and stirred 30 minutes at 100° C. (under N$_2$), subsequently followed by 45 minutes at 200° C. To the cooled reaction was added ethyl acetate and the resulting organic layer was washed with 2N NaOH, dried (Na$_2$SO$_4$), filtered and concentrated in vacuo. The mixture was dissolved in MeOH and filtrated over 80 g SCX-2 (MeOH followed by 1 N NH$_3$/MeOH). Subsequent purification by flash chromatography (MeOH/ethyl acetate) afforded compound 65 (amorphous, 0.6 g, 83%). $^1$H-NMR (400 MHz, CDCl$_3$) δ 10.65 (bs, 1H), 8.20 (dd, J=5 Hz, 2 Hz, 1H), 7.80 (dd, J=8 Hz, 2 Hz, 1H), 7.37-7.20 (m, 5H), 7.02 (dd, J=8 Hz, 5 Hz, 1H), 6.17 (s, 2H), 3.63 (dd, J gem=13 Hz, 2H), 2.95-2.90 (m, 2H), 2.77-2.54 (m, 4H), 2.43-2.38 (m, 1H), 2.12-2.02 (m, 1H), 1.65-1.55 (m, 1H). LCMS; R$_t$: 1.46 min, ([M+H]$^+$=292). Compound 65 (0.52 g, 1.8 mmol), 0.3 g ammonium formate (4.7 mmol) and 20% Pd(OH)$_2$/C (50 mg) were combined in MeOH (10 ml) and warmed to reflux for 1 hour. The mixture was cooled, filtered, concentrated and dissolved in MeOH. Subsequent filtration over 25 g SCX-2 (MeOH followed by 1 N NH$_3$/MeOH) gave the title compound: 2-Pyrrolidin-3-ylmethyl-1H-pyrrolo[2,3-b]pyridine (compound 66, 0.34 g, 94%) which was reacted with 1 equivalent of fumaric acid in MeOH and concentrated to afford the title compound 66 (amorphous) (free base/fumaric acid (1:1)). $^1$H-NMR (400 MHz, D$_6$DMSO): δ 11.6 (bs, 1H), 8.11 (dd, J=5 Hz, 2 Hz, 1H), 7.81 (dd, J=8 Hz, 2 Hz, 1H), 6.99 (dd, J=8 Hz, 5 Hz, 1H), 6.5 (s, 2H), 6.21 (bs, 1H), 3.29-3.22 (m, 2H), 3.17-3.09 (m, 1H), 2.90-2.76 (m, 3H), 2.72-2.61 (m, 1H), 2.06-1.97 (m, 1H), 1.69-1.59 (m, 1H). (TLC MeOH/triethylamine (97/3) R$_f$ 0.08).

2-(1-Methyl-pyrrolidin-3-ylmethyl)-1H-pyrrolo[2,3-b]pyridine. (compound 68)

Compound 66 (0.3 g, 1.49 mmol) was converted to compound 67, using the methodology described for compound 9. Yield 0.362 g (80.7%). (TLC ether R$_f$ 0.11), which was used as such to generate the title compound (68) using the methodology as described for compound 28. (Yield 0.17 g, 65%), mp 96-97° C. $^1$H-NMR (400 MHz, CDCl$_3$): δ N$_1$—H invisible, 8.16 (dd, J=5 Hz, 2 Hz, 1H), 7.77 (dd, J=8 Hz, 2 Hz, 1H), 6.98 (dd, J=8 Hz, 5 Hz, 1H), 6.16 (bs, 1H), 2.92-2.84 (m, 2H), 2.76-2.64 (m, 2H), 2.62-2.50 (m, 2H), 2.34 (s, 3H), 2.40-2.31 (m, 1H), 2.11-2.01 (m, 1H), 1.63-1.53 (m, 1H). (TLC MeOH/triethylamine (97/3) R$_f$ 0.2).

2-Pyrrolidin-3-yl-1H-pyrrolo[2,3-b]pyridine. (compound 78)

To a solution of anhydrous THF (75 ml) containing compound 17 (6.0 g, 23.2 mmol) was added 12.5 ml (24 mmol) LDA (2.0 M in THF/heptane) dropwise at –10° C. under N$_2$. After the addition, the resulting solution was stirred for 30 minutes at –10° C.-0° C. and subsequently lowered to –70° C.

Anhydrous CeCl$_3$ (6 g, 24.3 mmol) was added to 50 ml anhydrous THF and the resulting mixture was stirred for 0.5 hour at 30° C. (under N$_2$). This mixture was added to the 2-lithioderivate of 17, while keeping the temperature at –70° C. The temperature was raised to –10° C. and stirred for 10 minutes. Subsequently, the temperature was lowered to –50° C. Compound 71 (5 g, 28.5 mmol) dissolved in 50 ml THF was added to the reaction mixture and the resulting mixture was stirred for 2 hours at –30° C. The mixture was allowed to warm to ambient temperature and stirred for another 2 hours. The mixture was concentrated in vacuo, ethyl acetate was added and the organic layer was washed met a 5% NaHCO$_3$ solution, dried (Na$_2$SO$_4$), filtered and concentrated in vacuo. The resulting residue was purified by flash chromatography (diethyl ether/PE gradient 1:1 to pure diethyl ether) to give compound 72: 3-(1-benzenesulfonyl-1H-pyrrolo[2,3-b]pyridine-2-yl)-3-hydroxy-pyrrolidine-1-carboxylic acid t-butyl ester, (amorphous, 6.0 g, 58%). $^1$H-NMR (400 MHz, CDCl$_3$): δ 8.38-8.32 (m, 1H), 8.17-8.12 (m, 2H), 7.80-7.50 (m, 1H), 7.60-7.43 (m, 3H), 7.17-7.12 (m, 1H), 6.55 (s, 1H), 4.90 and 4.85 (2×bs, 1H), 4.24-4.13 (m, 1H), 3.92-3.79 (m, 1H), 3.75-3.48 (m, 2H), 2.68-2.47 (m, 2H), 1.49 (s, 9H). LCMS; R$_t$: 1.83 min, ([M+H]$^+$=444).

Compound 72 (8.6 g, 19.4 mmol), 12 g KOH and 20 ml hydrazine monohydrate were combined in 2-(2-hydroxyethoxy)-ethanol (150 ml) and stirred 30 minutes at 100° C. (under N$_2$). To the cooled reaction was added ethyl acetate and the resulting organic layer was washed several times with 2N NaOH, dried (Na$_2$SO$_4$), filtered and concentrated in vacuo. Subsequent purification by flash chromatography (diethyl ether followed by ethyl acetate) afforded compound 74 (oil, 4.97 g, 84%). $^1$H-NMR (400 MHz, D$_6$DMSO): δ 11.6 (bs, 1H), 8.15 (dd, J=5 Hz, 2 Hz, 1H), 7.87 (dd, J=8 Hz, 2 Hz, 1H), 7.01 (dd, J=8 Hz, 5 Hz, 1H), 6.38 (d, J=2 Hz, 1H), 5.67 (bs, 1H), 3.61-3.41 (m, 4H), 2.37-2.28 (m, 1H), 2.16-2.07 (m, 1H), 1.43 and 1.41 (2×s, 9H). LCMS; R$_t$: 1.48 min, ([M+H]$^+$= 304).

Compound 74 (4.92 g, 16.23 mmol), 100 ml H$_2$O and 100 ml 38% HCl solution were combined and heated to reflux for 12 hours. The mixture was cooled, concentrated and dissolved in MeOH. Filtration over 50 g SCX-2 (MeOH followed by 1 N NH$_3$/MeOH), followed by flash chromatography (MeOH/triethylamine (99/1)) afforded compound 76 (oil, 1.75 g, 58%). $^1$H-NMR (400 MHz, D$_6$DMSO): δ 12.1 (bs, 1H), 8.22 (dd, J=5 Hz, 2 Hz, 1H), 7.92 (dd, J=8 Hz, 2 Hz, 1H), 7.05 (dd, J=8 Hz, 5 Hz, 1H), 6.55-650 (m, 1H), 6.49 (s, 1H), 4.23-4.17 (m, 2H), 4.07-4.02 (m, 2H). LCMS; R$_t$: 0.91 min, ([M+H]$^+$=186).

Compound 76 (1.8 g, 9.73 mmol) and 20% Pd(OH)$_2$/C (180 mg) were combined in MeOH (100 ml). The mixture was hydrogenated at 50 psi for 2 hour. The mixture was filtered, concentrated, re-dissolved in MeOH and filtrated over 50 g SCX-2 (MeOH followed by 1 N NH$_3$/MeOH), followed by flash chromatography (MeOH/triethylamine (98/2)) to afford the title compound: 2-Pyrrolidin-3-yl-1H-pyrrolo[2,3-b]pyridine. (compound 78). (amorphous, 1.09 g, 59%). LCMS; R$_t$: 0.75 min, ([M+H]$^+$=188).

Separation of the enantiopure isomers was achieved using a chiral column (Chiralpak AD 20 um, 250×4.6, 20% MeOH, 20% EtOH, 60% heptane, 2 ml/min, δ=220 nm, R$_t$: 6.0 min (78A), ([α]$_D^{25}$−10 (c 1, MeOH) and R$_t$: 7.9 min (78B), ([α]$_D^{25}$+12 (c 1, MeOH).

Both isomers were reacted with 1 equivalent of fumaric acid in MeOH and concentrated to afford the salt of the title compound. mp 130-133° C. (free base/fumaric acid (1:1.5)). $^1$H-NMR (400 MHz, D$_6$DMSO): δ 11.7 (bs, 1H), 8.08 (dd, J=5 Hz, 2 Hz, 1H), 7.78 (dd, J=8 Hz, 2 Hz, 1H), 6.95 (dd, J=8 Hz, 5 Hz, 1H), 6.4 (s, 3H), 6.27 (bs, 1H), 3.63-3.53 (m, 2H), 3.33-3.15 (m, 3H), 2.36-2.25 (m, 1H), 2.08-1.97 (m, 1H).

2-Pyrrolidin-3-yl-1H-pyrrolo[3,2-b]pyridine. (compound 79)

Compound 69 (commercially available) was reacted with benzenesulfonylchloride as described for 45A/B, or described in Eur. J. of Med. Chem (2004). Yield 80-90%. Compound was 70 was obtained as an oil which crystallized on standing. $^1$H-NMR (400 MHz, CDCl$_3$): δ 8.54 (dd, J=5 Hz, 2 Hz, 1H), 8.27 (bd, J=8 Hz, 1H), 8.0-7.85 (m, 2H), 7.81 (d, J=4 Hz, 1H), 7.60-7.54 (m, 1H), 7.49-7.43 (m, 2H), 7.24 (dd, J=8 Hz, 5 Hz, 1H), 6.88 (bd, J=4 Hz, 1H).

Compound 70 (2.58 g, 10 mmol) was reacted with compound 71 using the methodology described for the synthesis of the aforementioned compound 72 to generate compound 73.

Compound 73: 3-(1-Benzenesulfonyl-1H-pyrrolo[3,2-b]pyridine-2-yl)-3-hydroxy-pyrrolidine-1-carboxylic acid t-butyl ester), (amorphous, 1.23 g, 28%). $^1$H-NMR (400 MHz, CDCl$_3$): δ 8.52-8.48 (m, 1H), 8.28-8.21 (m, 2H), 7.82-7.78 (m, 2H), 7.58-7.51 (m, 1H), 7.45-7.39 (m, 2H), 7.23-7.17 (m, 1H), 6.93 (bs, 1H), 4.58 and 4.53 (2×bs, 1H), 4.14-4.08 (m, 1H), 3.81-3.50 (m, 3H), 2.64-2.45 (m, 2H), 1.49 (s, 9H).

Compound 75: 3-Hydroxy-3-(1H-pyrrolo[3,2-b]pyridine-2-yl)-3-hydroxy-pyrrolidine-1-carboxylic acid t-butyl ester was obtained from compound 73 (1.2 g, 2.7 mmol) using the methodology described for the synthesis of the aforementioned compound 74.

Compound 75, (amorphous, 0.42 g, 51%). $^1$H-NMR (400 MHz, CDCl$_3$) showed rotational isomers (important ones described): δ 9.02 en 9.0 (2×s, 1H), 8.40-8.32 (m, 1H), 7.66-7.59 (m, 1H), 7.08-7.02 (bdd, J=8 Hz, 5 Hz, 1H), 6.41 and 6.33 (2×bs, 1H).

Compound 77: 2-(2,5-Dihydro-1H-pyrrol-3-yl)-1H-pyrrolo[3,2]pyridine was obtained from compound 75, (0.42 g, 1.38 mmol) using the methodology described for the synthesis of the aforementioned compound 76.

Compound 77, (amorphous, 0.2 g, 78%). $^1$H-NMR (400 MHz, D$_6$DMSO): δ 11.4 (bs, 1H), 8.19 (bd, J=5 Hz, 1H), 7.61 (bd, J=8 Hz,1H), 7.0 (dd, J=8 Hz, 5 Hz, 1H), 6.43-6.38 (m, 2H), 3.93-3.88 (m, 2H), 3.77-3.72 (m, 2H).

The title compound: 2-Pyrrolidin-3-yl-1H-pyrrolo[3,2-b]pyridine. (compound 79) was obtained from compound 77 (0.19 g, 1.02 mmol) using the methodology described for the synthesis of the aforementioned compound 78.

Compound 79, (amorphous, 0.16 g, 83%), was reacted with 1 equivalent of fumaric acid in MeOH and concentrated to afford the salt of the title compound. (amorphous, free base/fumaric acid (1:1.5)). $^1$H-NMR (400 MHz, D$_6$DMSO): δ 11.6 (bs, 1H), 8.26 (bd, J=5 Hz, 1H), 7.69 (bd, J=8 Hz, 1H), 7.05 (bdd, J=8 Hz, 5 Hz, 1H), 6.54 (s, 3H), 6.48 (bs, 1H), 3.74-3.62 (m, 2H), 3.40-3.25 (m, 2H), 2.44-2.37 (m, 1H), 2.09-1.97 (m, 1H).

(R)-2-Pyrrolidin-2-ylmethyl-1H-pyrrolo[3,2-b]pyridine. (compound 81A) and (S)-2-Pyrrolidin-2-ylmethyl-1H-pyrrolo[3,2-b]pyridine. (compound 81B)

Lithiation (LDA) of compound 70 (1.42 g, 5.05 mmol) and subsequent reaction with 35 was done using the methodology described for the synthesis (first step) of compound 39A. Compound 80A: (R)-1-Benzenesulfonyl-2-pyrrolidin-2-yl-methyl-1H-pyrrolo[3,2-b]pyridine. (1.32 g, 70%). $^1$H-NMR (400 MHz, CDCl$_3$): δ 8.48 (dd, J=5 Hz, 2 Hz, 1H), 8.40 (bd, J=8 Hz, 1H), 7.73-7.70 (m, 2H), 7.57-7.53 (m, 1H), 7.44-7.40 (m, 2H), 7.18 (dd, J=8 Hz, 5 Hz, 1H), 3.62-3.55 (m, 1H), 3.23-3.13 (m, 2H), 3.08-3.02 (m, 1H), 2.95-2.88 (m, 1H), 2.0-1.95 (m, 1H), 1.90-1.75 (m, 1H), 1.51-1.42 (m, 1H).

A solution of 247 mg KOt-Bu (1.1 eq) in 40 ml MeOH was prepared and stirred for 30 min under N$_2$. Compound 80A (683 mg, 2 mmol) was added and the mixture was stirred for 20 hour at 50° C. The mixture was cooled, filtered, concentrated and re-dissolved in MeOH. Filtration over 25 g SCX-2 (MeOH followed by 1 N NH$_3$/MeOH) followed by flash chromatography (MeOH/triethylamine (97/3)) afforded the title compound: (R)-2-Pyrrolidin-2-ylmethyl-1H-pyrrolo[3,2-b]pyridine. (compound 81A). ([α]$_D^{25}$−74 (c 1, toluene). $^1$H-NMR (400 MHz, D$_6$DMSO): δ 11.0 (bs, 1H), 8.20 (bd, J=5 Hz, 1H), 7.62 (bd, J=8 Hz, 1H), 6.98 (dd, J=8 Hz, 5 Hz, 1H), 6.30 (bs, 1H), 3.37-3.28 (m, 1H), 2.90-2.70 (m, 4H), 1.82-1.55 (m, 3H), 1.37-1.28 (m, 1H).

(S)-2-Pyrrolidin-2-ylmethyl-1H-pyrrolo[3,2-b]pyridine (compound 81B) was obtained using the methodology described for compound 81A, by using the sulphamidate 36. ($[\alpha]_D^{25}$+74 (c 1, toluene).

(R)-5-Methoxy-2-pyrrolidin-2-ylmethyl-1H-pyrrolo[3,2-b]pyridine. (compound 85)

To a solution of 9.5 ml (59 mmol) TMEDA in anhydrous THF (60 ml) was added 10.5 ml t-butyl-lithium (1.5 M in pentane) dropwise at −70° C. under $N_2$. After the addition, the resulting solution was stirred for 15 minutes at −70° C. At this temperature, a solution of 83 (3.7 g, 14.3 mmol) in 25 ml THF was added dropwise (10 minutes). The mixture was stirred for 60 minutes at −70° C. At this temperature, a solution of 35 (2.33 g, 14.3 mmol) in 30 ml anhydrous THF was added and the mixture was stirred for 30 minutes at −70° C. and subsequently raised to −20° C. The mixture was allowed to warm to ambient temperature and stirred for another 20 hours.

The reaction mixture was concentrated and the residue was dissolved in 100 ml 1N HCl, and 100 ml THF. The mixture was stirred at 70° C. for 20 hours. The reaction mixture was concentrated in vacuo. The resulting residue was taken up in ethyl acetate, washed with 2N NaOH, dried ($Na_2SO_4$), filtered and concentrated in vacuo. Purification by flash chromatography (MeOH/triethylamine (97/3)) afforded compound 84 (solid, 2.83 g, 53%). mp 101-103° C. $^1$H-NMR (400 MHz, $CDCl_3$): δ 8.30 (d, J=9 Hz, 1H), 7.71-7.65 (m, 2H), 7.57-7.50 (m, 1H), 7.45-7.35 (m, 2H), 6.65 (d, J=9 Hz,1H), 6.54 (s, 1H), 3.94 (s, 3H), 3.56-3.47 (m, 1H), 3.15-2.98 (m, 4H), 2.05-1.65 (m, 3H), 1.48-1.37 (m, 1H).

Compound 84 was converted to the title compound (85) using the methodology used for the synthesis of 39A. The title compound: (R)-5-Methoxy-2-pyrrolidin-2-ylmethyl-1H-pyrrolo[3,2-b]pyridine was obtained as a syrup (1.18 g, 68%), $[\alpha]_D^{25}$−42 (c 1, $CHCl_3$), which was reacted with 1 equivalent of fumaric acid in MeOH and concentrated to afford the title compound 95 (amorphous) (free base/fumaric acid (1:1)). mp 180-182° C.

(R)-3-Pyrrolidin-2-ylmethyl-1H-pyrrolo[3,2-b]pyridine. (compound 88)

4.6 g (25.8 mmol) NBS was added to 3.05 g (25.8 mmol) 4-azaindole in 40 ml of DMF (0° C).). The mixture was stirred for 30 minutes at 0° C. MeOH was added and the mixture was filtrated over SCX-2, followed by flash chromatography (ethyl acetate followed by MeOH) afforded 3-bromo-1H-[3,2-b]pyridine (86) as a solid. mp 241° C. (4.52 g, 89%). $^1$H-NMR (400 MHz, $D_6$DMSO): δ 11.7 (bs, 1H), 8.39 (dd, J=5 Hz, 2 Hz, 1H), 7.85 (s, 1H), 7.82 (dd, J=8 Hz, 2 Hz, 1H), 7.19 (dd J=8 Hz, 5 Hz, 1H).

To a solution of anhydrous THF (75 ml) containing compound 86 (2.28 g, 11.6 mmol) was added 4.6 ml n-BuLi (2.5 M in hexane) dropwise at −78° C. under $N_2$. After the addition, the resulting solution was stirred for 45 minutes at −78° C. At this temperature, a solution of TIPS-Cl (2.73 ml) in 10 ml THF was added dropwise. After the addition, the resulting solution was stirred for 1 hour at −78° C. Then mixture was allowed to warm to ambient temperature. The reaction mixture was concentrated and the resulting residue was taken up in ethyl acetate, washed with a 5% $NaHCO_3$ solution, dried ($Na_2SO_4$), filtered and concentrated in vacuo. Purification by flash chromatography (diethyl ether/PE (1/1)) afforded 3-bromo-1-tri-tert-butylsilanyl-1H-pyrrolo[3,2-b]pyridine (87) as a solid. mp 79-80° C. (3.52 g, 86%). $^1$H-NMR (400 MHz, $CDCl_3$): δ 8.55 (dd, J=5 Hz, 2 Hz, 1H), 7.76 (dd, J=8 Hz, 2 Hz, 1H), 7.49 (s, 1H), 7.13 (dd, J=8 Hz, 5 Hz, 1H), 1.73-1.60 (m, 3H), 1.15 and 1.13 (2×s, 18H).

To a solution of anhydrous THF (100 ml) containing compound 87 (3.42 g, 9.69 mmol) was added 3.9 ml n-BuLi (2.5 M in hexane) dropwise (−78° C. under $N_2$). After the addition, the resulting solution was stirred for 60 minutes at −78° C. At this temperature, a solution of 35 (1.58 g, 9.69 mmol) in 10 ml THF was added dropwise (5 minutes). After the addition of 35, the temperature was raised to −20° C. and the resulting solution was stirred for 2 hours. The mixture was allowed to warm to ambient temperature and stirred for another 2 hours.

The reaction mixture was concentrated and the residue was dissolved in 40 ml 1N HCl, 40 ml EtOH and 40 ml THF. The mixture was stirred at 80° C. for 18 hours. The reaction mixture was concentrated in vacuo. MeOH (25 ml) was added and the mixture was concentrated on 25 g $SiO_2$. Subsequent flash chromatography (MeOH/triethylamine (98/2) afforded the title compound: (R)-3-Pyrrolidin-2-ylmethyl-1H-pyrrolo[3,2-b]pyridine. (compound 88), (amorphous, 0.32 g, 0.72 mmol, 9.3%). $^1$H-NMR (400 MHz, $CDCl_3$) δ 9.1 (bs, 1H), 8.42 (dd, J=5 Hz, 2 Hz, 1H), 7.58 (dd, J=8 Hz, 2 Hz, 1H), 7.20 (s, 1H), 7.06 (dd, J=8 Hz, 5 Hz, 1H), 3.59-3.51 (m, 1H), 3.14-3.02 (m, 2H), 2.97-2.85 (m, 2H), 2.0-1.90 (m, 1H), 1.86-1.71 (m, 2H), 1.54-1.43 (m, 1H). LCMS: $R_t$; 0.64 min, ([M+H]$^+$=202). $[\alpha]_D^{25}$−10 (c 1, dioxane).

(R)-6-Pyrrolidin-2-ylmethyl-7H-pyrrolo[2,3-d]pyrimidine. (compound 95)

Commercially available 6-chloro-7-deazapurine (1.58 g, 10.3 mmol), 3.25 g ammonium formate (51.6 mmol) and 20% Pd(OH)$_2$/C (140 mg) were combined in MeOH (50 ml) and warmed to reflux for 2 hours. The mixture was cooled, filtered, concentrated and re-dissolved in MeOH. Filtration over 25 g SCX-2 (MeOH followed by 1 N $NH_3$/MeOH), followed by flash chromatography (ethyl acetate/MeOH (9/1)) afforded compound 90 (1.2 g, 4.02 mmol, 97%) amorphous material. $^1$H-NMR (400 MHz, $CDCl_3$): δ 11.1 (bs, 1H), 9.1 (bs, 1H), 9.0 (bs, 1H), 7.45-7.40 (m, 1H), 6.68-6.62 (m, 1H).

7H-Pyrrolo[2,3-d]pyrimidine (1.16 g, 9.74 mmol), was dissolved in 100 ml anhydrous THF under $N_2$. At 0° C., a 60% dispersion of NaH 0.51 g in mineral oil was added. The mixture was stirred at ambient temperature and 2.93 ml (9.8 mmol) (2-chloromethoxy-ethyl)-trimethyl-silane dissolved in 15 ml anhydrous THF was added. The reaction mixture was stirred at room temperature for 2 hour and subsequently concentrated in vacuo. Ethyl acetate was added to the mixture and the organic layer was washed three times with a saturated $NaHCO_3$ solution, dried ($Na_2SO_4$), filtered and concentrated. The resulting residue was purified by flash chromatography (diethyl ether) to afford 7-(2-trimethylsilanyl-ethoxymethyl-7H-pyrrolo[2,3-d]pyrimidine (compound 91), (amorphous, 0.84 g, 35%). $^1$H-NMR (400 MHz, $CDCl_3$): δ 9.1 (bs, 1H), 9.0 (bs, 1H), 7.43 (bd, J=4 Hz, 1H), 6.68 (bd, J=4 Hz, 1H), 5.73 (s, 1H), 3.6 (t, J=8 Hz, 2H), 0.97 (t, J=8 Hz, 2H), 0.1 (s, 9H).

Under nitrogen, 0.62 ml (3.7 mmol) 2,2,6,6-tetramethylpiperidine was added to 20 ml anhydrous THF (−78° C.). n-BuLi 1.3 ml (2.5 M, 3.33 mmol) was added and the reaction mixture was stirred for 30 minutes. Compound 91 (0.83 g, 2.16 mmol), dissolved in 10 ml THF was added and the mixture was stirred for 30 minutes. Compound 35 (557 mg, 2.16 mmol) dissolved in 5 ml THF was added. After the addition of 35, the temperature was raised to −30° C. and the resulting solution was stirred for 2 hours. The mixture was allowed to warm to ambient temperature and stirred for another 2 hours. A saturated NH$_4$Cl solution (5 ml) was added to the reaction mixture followed by 25 g SiO$_2$ and the mixture was subsequently concentrated in vacuo. The resulting residue was purified by flash chromatography (dichloromethane/MeOH/NH$_4$OH) (90/10/1) to give compound 93 (0.4 g, 44.9%). LCMS; R$_t$: 1.38 min, ([M+H]$^+$=413).

Compound 93 (0.63 g, 1.53 mmol), 11.4 ml tetrabutylammonium fluoride (1M in THF) and 25 ml THF were combined and the mixture was heated to reflux (36 hours).

The mixture was cooled, 25 g SiO$_2$ was added and subsequently concentrated in vacuo. The resulting residue was purified by flash chromatography (dichloromethane/MeOH/NH$_4$OH) (90/10/0.5) to give compound 94 (0.35 g, 81%). $^1$H-NMR (400 MHz, CDCl$_3$): δ 11.3 (bs, 1H), 8.80 (bs, 1H), 8.65 (bs, 1H), 6.2 (bs, 1H), 3.95-3.88 (m, 1H), 3.65-3.58 (m, 1H), 3.24-3.17 (m, 2H), 2.89-2.82 (m, 1H), 2.05-1.96 (m, 2H), 1.74-1.6 (m, 2H).

Compound 94 (0.35 g, 1.24 mmol), 10 ml 1N HCl and 10 ml EtOH were combined and heated to reflux for 18 hours. The reaction mixture was cooled and concentrated in vacuo. The resulting residue was taken up in ethyl acetate, washed with a 2N NaOH solution, dried (Na$_2$SO$_4$), filtered and concentrated in vacuo. Purification by flash chromatography (MeOH/triethylamine 97/3)) afforded the title compound: (R)-6-pyrrolidin-2-ylmethyl-7H-pyrrolo[2,3-d]pyrimidine. (95), (amorphous, 70 mg, 27.9%). LCMS; R$_t$: 0.68 min, ([M+H]$^+$=203), which was reacted with 1 equivalent of fumaric acid in MeOH and concentrated to afford the title compound 95 (amorphous) (free base/fumaric acid (1:2)). $^1$H-NMR (400 MHz, D$_6$DMSO): δ 12.8-11.8 (bs, 1H), 8.86 (s, 1H), 8.68 (s, 1H), 6.54 (s, 4H), 6.45 (s, 1H), 3.85-3.79 (m, 1H), 3.25-3.19 (m, 2H), 3.17-3.09 (m, 2H), 2.10-2.03 (m, 1H), 2.00-1.92 (m, 1H)), 1.90-1.82 (m, 1H), 1.69-1.62 (m, 1H).

Structures of the compounds of the invention of which the syntheses are described above are given in the table below.

(I)

| Cmp | X | Y | Z | n | m | R$_2$ | R$_3$ | R$_4$ | R$_5$ | R$_6$ |
|---|---|---|---|---|---|---|---|---|---|---|
| 79 | C | N | C | 0 | 0 | 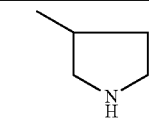 | H | H | H | H |
| 78 | N | C | C | 0 | 0 | | H | H | H | H |
| 78A | N | C | C | 0 | 0 | 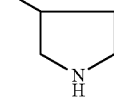 (S) | H | H | H | H |
| 78B | N | C | C | 0 | 0 | 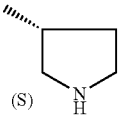 (R) | H | H | H | H |
| 26 | N | C | C | 0 | 0 | 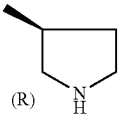 | H | H | H | H |
| 29B | N↓O | C | C | 0 | 0 | 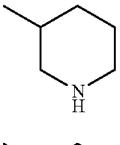 | H | H | H | H |
| 26A | N | C | C | 0 | 0 |  (S) | H | H | H | H |
| 26B | N | C | C | 0 | 0 | 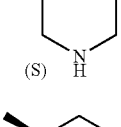 (R) | H | H | H | H |

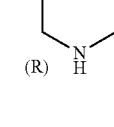

-continued

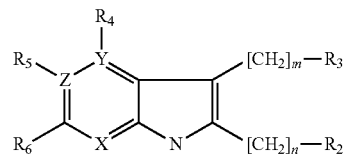
(I)

| Cmp | X | Y | Z | n | m | R$_2$ | R$_3$ | R$_4$ | R$_5$ | R$_6$ |
|---|---|---|---|---|---|---|---|---|---|---|
| 6 | N | C | C | 0 | 0 | H | 3-methylpiperidine (NH) | H | H | H |
| 10B | N→O | C | C | 0 | 0 | H | 3-methylpiperidine (NH) | H | H | H |
| 33 | N | C | C | 0 | 0 | 3-methylpiperidine (NH) | H | Cl | H | H |
| 32 | N | C | C | 0 | 0 | 3-methylpiperidine (NH) | H | H | H | Cl |
| 32A | N | C | C | 0 | 0 | (S)-3-methylpiperidine | H | H | H | Cl |
| 32B | N | C | C | 0 | 0 | (R)-3-methylpiperidine | H | H | H | Cl |
| 13 | N | C | C | 0 | 0 | H | 3-methylpiperidine (NH) | H | H | Cl |
| 28 | N | C | C | 0 | 0 | 1,3-dimethylpiperidine | H | H | H | H |
| 25 | N | C | C | 0 | 0 | 3-methyl-1,2,5,6-tetrahydropyridine | H | H | H | H |
| 24 | N | C | C | 0 | 0 | 3-hydroxy-3-methylpiperidine | H | H | H | H |
| 19 | N | C | C | 0 | 0 | 3-hydroxy-3-methyl bicyclic amine | H | H | H | H |

-continued

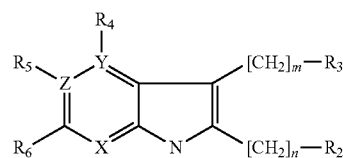

(I)

| Cmp | X | Y | Z | n | m | R₂ | R₃ | R₄ | R₅ | R₆ |
|---|---|---|---|---|---|---|---|---|---|---|
| 21 | N | C | C | 0 | 0 | 3-methyl-1-azabicyclic amine | H | H | H | H |
| 10A | N | C | C | 0 | 0 | H | 3-hydroxy-3-methylpiperidine | H | H | H |
| 16 | N | C | C | 0 | 0 | H | methyl-bridged bicyclic amine | H | H | H |
| 20 | N | C | C | 0 | 0 | H | methyl-bridged bicyclic amine | H | H | H |
| 39 | N | C | C | 1 | 0 | 2-methylpyrrolidine (R)/(S) 1:9 | H | H | H | H |
| 39A | N | C | C | 1 | 0 | 2-methylpyrrolidine | H | H | H | H |
| 95 | N | C | N | 1 | 0 | 2-methylpyrrolidine | H | H | H | H |
| 52A | N | C | C | 1 | 0 | 2-methylpyrrolidine | H | H | Br | H |
| 53A | N | C | C | 1 | 0 | 2-methylpyrrolidine | H | H | CH₃ | H |
| 85 | C | N | C | 1 | 0 | (R) 2-methylpyrrolidine | H | H | OCH₃ | H |
| 81A | C | N | C | 1 | 0 | 2-methylpyrrolidine | H | H | H | H |
| 88 | C | N | C | 0 | 1 | H | (R) 2-methylpyrrolidine | H | H | H |
| 81B | C | N | C | 1 | 0 | (S) 2-methylpyrrolidine | H | H | H | H |
| 47A | N | C | C | 1 | 0 | (R) 2-methylpyrrolidine | H | H | H | F |
| 45A | N | C | C | 1 | 0 | (R) 2-methylpyrrolidine | H | H | H | Cl |
| 46A | N | C | C | 1 | 0 | (R) 2-methylpyrrolidine | H | H | H | Br |

-continued

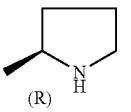

| Cmp | X | Y | Z | n | m | R₂ | R₃ | R₄ | R₅ | R₆ |
|---|---|---|---|---|---|---|---|---|---|---|
| 49 | N | C | C | 1 | 0 | 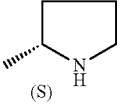 (R) | H | H | H | OCH₃ |
| 39B | N | C | C | 1 | 0 | 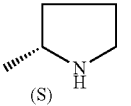 (S) | H | H | H | H |
| 52B | N | C | C | 1 | 0 | 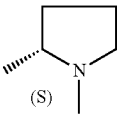 (S) | H | H | Br | H |
| 41B | N | C | C | 1 | 0 | 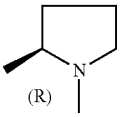 (S) | H | H | H | H |
| 47B | N | C | C | 1 | 0 | | H | H | H | F |
| 45B | N | C | C | 1 | 0 | | H | H | H | Cl |
| 46B | N | C | C | 1 | 0 | | H | H | H | Br |
| 41A | N | C | C | 1 | 0 | 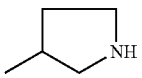 (R) | H | H | H | H |
| 66 | N | C | C | 1 | 0 | 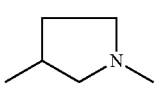 | H | H | H | H |
| 68 | N | C | C | 1 | 0 | | H | H | H | H |
| 65 | N | C | C | 1 | 0 | 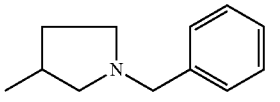 | H | H | H | H |

The names of the compounds are listed in the table below:

| Compound | Name |
|---|---|
| 6 | 3-piperidin-3-yl-1H-pyrrolo[2,3-b]pyridine |
| 10A | 3-(1H-pyrrolo[2,3-b]pyridine-3-yl)-piperidin-3-ol |
| 10B | 3-piperidin-3-yl-1H-pyrrolo[2,3-b]pyridine 7-oxide |
| 13 | 6-chloro-3-piperidin-3-yl-1H-pyrrolo[2,3-b]pyridine |
| 16 | 3-(1H-pyrrolo[2,3-b]pyridine-3-yl)-1-aza-bicyclo[2.2.2]octane |
| 19 | 3-(1H-pyrrolo[2,3-b]pyridine-2-yl)-1-aza-bicyclo[2.2.2]octan-3-ol |
| 20 | 3-(1H-pyrrolo[2,3-b]pyridine-3-yl)-1-aza-bicyclo[2.2.2]oct-2-ene |
| 21 | 3-(1H-pyrrolo[2,3-b]pyridine-2-yl)-1-aza-bicyclo[2.2.2]octane |
| 24 | 3-(1H-pyrrolo[2,3-b]pyridine-2yl)-piperidin-3-ol |
| 25 | 2-(1,2,5,6-tetrahydro-pyridin-3-yl)-1H-pyrrolo[2,3-b]pyridine |
| 26 | 2-piperidin-3-yl-1H-pyrrolo[2,3-b]pyridine |
| 26A | (S)-2-piperidin-3-yl-1H-pyrrolo[2,3-b]pyridine |
| 26B | (R)-2-piperidin-3-yl-1H-pyrrolo[2,3-b]pyridine |
| 28 | 2-(1-methyl-piperidin-3-yl)-1H-pyrrolo[2,3-b]pyridine |
| 29B | 2-piperidin-3-yl-1H-pyrrolo[2,3-b]pyridine 7-oxide |
| 32 | 6-chloro-2-piperidin-3-yl-1H-pyrrolo[2,3-b]pyridine |
| 32A | (S)-6-chloro-2-piperidin-3-yl-1H-pyrrolo[2,3-b]pyridine |
| 32B | (R)-6-chloro-2-piperidin-3-yl-1H-pyrrolo[2,3-b]pyridine |
| 33 | 4-chloro-2-piperidin-3-yl-1H-pyrrolo[2,3-b]pyridine |
| 39 | 2-pyrrolidin-2-ylmethyl-1H-pyrrolo[2,3-b]pyridine |
| 39A | (R)-2-pyrrolidin-2-ylmethyl-1H-pyrrolo[2,3-b]pyridine |
| 39B | (S)-2-pyrrolidin-2-ylmethyl-1H-pyrrolo[2,3-b]pyridine |
| 41A | (S)-2-(1-methyl-pyrrolidin-2-ylmethyl)-1H-pyrrolo[2,3-b]pyridine |
| 41B | (R)-2-(1-methyl-pyrrolidin-2-ylmethyl)-1H-pyrrolo[2,3-b]pyridine |

-continued

| Compound | Name |
|---|---|
| 45A | (R)-6-chloro-2-pyrrolidin-2-ylmethyl-1H-pyrrolo[2,3-b]pyridine |
| 45B | (S)-6-chloro-2-pyrrolidin-2-ylmethyl-1H-pyrrolo[2,3-b]pyridine |
| 46A | (R)-6-bromo-2-pyrrolidin-2-ylmethyl-1H-pyrrolo[2,3-b]pyridine |
| 46B | (S)-6-bromo-2-pyrrolidin-2-ylmethyl-1H-pyrrolo[2,3-b]pyridine |
| 47A | (R)-6-fluoro-2-pyrrolidin-2-ylmethyl-1H-pyrrolo[2,3-b]pyridine |
| 47B | (S)-6-fluoro-2-pyrrolidin-2-ylmethyl-1H-pyrrolo[2,3-b]pyridine |
| 49 | (R)-6-methoxy-2-pyrrolidin-2-ylmethyl-1H-pyrrolo[2,3-b]pyridine |
| 52A | (R)-5-bromo-2-pyrrolidin-2-ylmethyl-1H-pyrrolo[2,3-b]pyridine |
| 52B | (S)-5-bromo-2-pyrrolidin-2-ylmethyl-1H-pyrrolo[2,3-b]pyridine |
| 53A | (R)-5-methyl-2-pyrrolidin-2-ylmethyl-1H-pyrrolo[2,3-b]pyridine |
| 65 | 2-(1-benzyl-pyrrolidin-3-ylmethyl)-1H-pyrrolo[2,3-b]pyridine |
| 66 | 2-pyrrolidin-3-ylmethyl-1H-pyrrolo[2,3-b]pyridine |
| 68 | 2-(1-methyl-pyrrolidin-3-ylmethyl)-1H-pyrrolo[2,3-b]pyridine |
| 78 | 2-pyrrolidin-3-yl-1H-pyrrolo[2,3-b]pyridine |
| 78A | (S)-2-pyrrolidin-3-yl-1H-pyrrolo[2,3-b]pyridine |
| 78B | (R)-2-pyrrolidin-3-yl-1H-pyrrolo[2,3-b]pyridine |
| 79 | 2-pyrrolidin-3-yl-1H-pyrrolo[3,2-b]pyridine |
| 81A | (R)-2-pyrrolidin-2-ylmethyl-1H-pyrrolo[3,2-b]pyridine |
| 81B | (S)-2-pyrrolidin-2-ylmethyl-1H-pyrrolo[3,2-b]pyridine |
| 85 | (R)-5-methoxy-2-pyrrolidin-2-ylmethyl-1H-pyrrolo[3,2-b]pyridine |
| 88 | (R)-3-pyrrolidin-2-ylmethyl-1H-pyrrolo[3,2-b]pyridine |
| 95 | (R)-6-pyrrolidin-2-ylmethyl-7H-pyrrolo[2,3-d]pyrimidine |

Example 4

Synthesis of Compounds Disclosed in EP 1 178 045

(R)-3-Pyrrolidin-2-ylmethyl-1H-pyrrolo[2,3-b]pyridine. (compound 96) and (S)-3-Pyrrolidin-2-ylmethyl-1H-pyrrolo[2,3-b]pyridine. (comp. 97)

Metalation of 3-bromo-7-azaindole with 2.2 equivalents of n-Buli (*J. Heterocyclic Chem.*, 1984) gave the di-lithioderivate which was trapped the sulphamidate 35 (−30° C. under N$_2$). Work up using the methodology described for 39A afforded the title compound 96: (R)-3-pyrrolidin-2-ylmethyl-1H-pyrrolo[2,3-b]pyridine (46%). LCMS; R$_t$; 0.91 min, ([M+H]$^+$=202). [α]$_D^{25}$−8 (c 1, MeOH), which was converted to its salt (free base/fumaric acid (1:1)), (amorphous). $^1$H-NMR (400 MHz, D$_6$DMSO): δ 11.5 (bs, 1H), 8.21 (dd, J=5 Hz, 2 Hz, 1H), 8.02 (dd, J=8 Hz, 2 Hz, 1H), 7.42 (s, 1H), 7.05 (dd, J=8 Hz, 2 Hz, 1H), 3.79-3.71 (m, 1H), 3.27-3.21 (m, 1H), 3.19-3.09 (m, 2H), 3.05-2.99 (m, 1H), 2.03-1.79 (m, 3H), 1.69-1.61 (m, 1H).

(S)-3-Pyrrolidin-2-ylmethyl-1H-pyrrolo[2,3-b]pyridine. (comp. 97) was obtained (from 36) using the methodology described for compound 96. ([α]$_D^{25}$+8 (c 1, MeOH).

(R)-3-(1-Methyl-pyrrolidin-2-ylmethyl)-1H-pyrrolo[2,3-b]pyridine. (compound 98) and (S)-3-(1-Methyl-pyrrolidin-2-ylmethyl)-1H-pyrrolo[2,3-b]pyridine. (comp. 99)

Compound 96 and 97 were converted to the title compounds 98 and 99 as described in EP 1 178 045. Compound 98: LCMS; R$_t$; 0.94 min, ([M+H]$^+$=216). [α]$_D^{25}$+68 (c 1, dioxane). Compound 99: [α]$_D^{25}$−68 (c 1, dioxane).

Structures of the four compounds described above are listed in the table below:

| Cp | Structure | name | EP 1178045 |
|---|---|---|---|
| 96 | 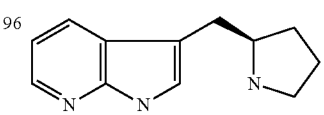 | (R)-3-pyrrolidin-2-ylmethyl-1H-pyrrolo-[2,3-b]pyridine | Ex.11(rac) |
| 97 | 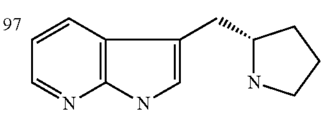 | (S)-3-pyrrolidin-2-ylmethyl-1H-pyrrolo-2,3-b]pyridine | Ex.11(rac) |
| 98 | 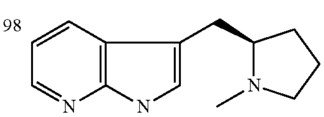 | (R)-3-(1-methyl-pyrrolidin-2-ylmethyl-1H-pyrrolo[2,3-b]pyridine | Ex.13(rac) |
| 99 | 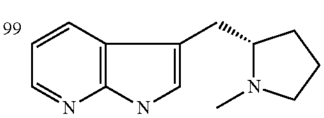 | (S)-3-(1-methyl-pyrrolidin-2-ylmethyl-1H-pyrrolo[2,3-b]pyridine | Ex.13(rac) |

Ex.11(rac) denotes: example number 11 in EP 1 178 045, disclosed as racemate

Example 5

Pharmacological Methods

In vitro Affinity for Rat Nicotinic Cholinergic Receptors

Affinity of the compounds for nicotine receptors in rat brain receptors was determined by CEREP (Celle IÉvescault, France), using a known assay (Pabreza, 1991).

In vitro Affinity for Human Nicotinic Cholinergic Receptors

Affinity of the compounds for human nicotine receptors cloned into SK-N-F1 neuroblastoma cells was determined by Novascreen (Hanover, Md., U.S.A.), using a known assay (Perry, 1995).

in vitro [$^3$H]-Dopamine Release

Dopamine release was measured using rat striatal slices, as described (Stoof, 1980). Male rats (Wistar Hsd/Cpb: WU; 175-200 g) were decapitated and the striatum was rapidly removed from the brain. Slices (0.3×0.3×2.00 mm) were prepared by using a McIlwain chopper. Striatal slices of 6 rats were pooled and incubated for 15 min in 5 ml Krebs-Ringer bicarbonate medium, containing 0.37 MBq [$^3$H]-DA. After labeling, the slices were transferred to each of the 24 chambers (10 mg tissue per chamber; 0.20 ml volume) of a superfusion apparatus and subsequently superfused (0.20 ml/min) with medium. All superfusion experiments were performed in Kreb's bicarbonate buffer of the following composition: 118 mM NaCl, 2.4 mM KCl, 2.4 mM $CaCl_2.2H_2O$, 1.2 mM $MgSO_4.7H_2O$, 1.2 mM $KH_2PO_4$, 25 mM $NaHCO_3$ and 10 mM glucose buffered to pH 7.4, saturated with 95% $O_2$/5% $CO_2$. After a pre-superfusion period of 45 min thirteen 10 min-fractions were collected (starting at t=0). Calcium-dependent neurotransmitter release was induced during superfusion at t=10 (S1), t=50 (S2) and t=90 min (S3) for 5 min by exposing the slices to medium in which the $K^+$ concentration had been raised to 10 mM; the NaCl concentration was decreased accordingly to maintain osmolarity.

Test compounds or epibatidine were added together with the $K^+$ pulse to the medium at t=50 ($10^{-8}$ M) and t=90 min ($10^{-6}$ M) for 5 min. In parallel responses of test compound were determined in the presence of the a specific nicotine receptor antagonist mecamylamine ($10^{-5}$ M) or the specific $\alpha_4\beta_2$ n-Acetylcholine receptor antagonist DHBE ($10^{-6}$ M). At the end of the experiment the remaining radioactivity was extracted from the tissue with 0.1 M HCl.

The radioactivity in superfusion fractions and tissue extract was determined by liquid scintillation counting. The efflux of radioactivity during each collection period was expressed as the percentage of the amount of radioactivity in the slices at the beginning of the respective collection period. In order to calculate the induced [$^3$H]-dopamine release, the spontaneous efflux of radioactivity was subtracted from the total overflow of radioactivity during stimulation and the next 15 min.

The spontaneous release of radioactivity was calculated, assuming a linear decline from the 10 min interval before, to the interval 20-30-min after the start of stimulation. The ratios S2/S1 and S3/S1 were used as index for the stimulated release. Effects of test compounds were calculated as percentages of the control group. Mecamylamine or DHBE sensitive release was expressed as percentage inhibition of evoked [$^3$H]-dopamine release in response to test compound. Within each assay, each test compound was replicated using 2-3 chambers; replicates were averaged.

In vitro [$^3$H]-Dopamine Uptake

Male rats (Wistar Hsd/Cpb: WU; 175-200 g) were decapitated; the striatum was rapidly removed and a crude synaptosomal fraction (P2) was prepared by homogenization and centrifugation. Synaptosomes were pre-incubated in absence or presence of the test compound for 15 min at 37° C., in a medium containing the monoamine oxidase inhibitor pargyline (7×$10^{-6}$ M) (Coyle, 1969). Subsequently, [$^3$H]-dopamine (2×$10^{-7}$ M final concentration) was added and incubation was continued for 10 min. [$^3$H]-dopamine uptake was stopped by filtration and the synaptosomes were washed four times with phosphate buffered saline. The amount of [$^3$H]-dopamine in the synaptosomes was determined by Beta-plate liquid scintillation counting. Compounds were tested in a concentration range of $10^{-9}$ to $10^{-5}$ M. Inhibitory effects on the uptake of [$^3$H]-dopamine were expressed using the $pIC_{50}$ value (the negative logarithm of the concentration at which the drug caused 50% uptake inhibition). Inhibition of DA uptake was performed in duplicate.

Example 6

Pharmacological Test Results

In vitro pharmacological test results were obtained according to the protocols given above are shown in the table below.

| | in vitro pharmacology | | | |
|---|---|---|---|---|
| | Receptor binding | | Functional activity | |
| | displacement | | release | |
| | [$^3$H]-cytisine $pK_i$ | [$^3$H]-epibatidin $pK_i$ | [$^3$H]-Dopamine % of control | re-uptake [$^3$H]-Dopamine $pIC_{50}$ |
| references | | | | |
| nicotine | 8.2 | 7.3 | 180 | <* |
| cytisine | 8.7 | 7.5 | 136 | < |
| nomifensin | | | | 6.6 |
| bupropion | | | 124 | 5.4 |
| GBR 12909 | | | | 7.0 |
| Compound | | | | |
| 96 | 5.6 | | 124 | < |
| 97 | 5.2 | | 122 | < |
| 98 | < | | 132 | < |
| 99 | 5.9 | | 112 | < |
| Comp. | | | | |
| 6 | 5.5 | < | 139 | 5.4 |
| 13 | 5.5 | < | 174 | 5.8 |
| 16 | 5.4 | 6.8 | | |
| 21 | 5.3 | 6.8 | | |
| 26A | < | < | 139 | 5.6 |
| 26B | 5.3 | 6.0 | 121 | 6.2 |
| 32 | < | | 173 | |
| 32B | 5.3 | < | 170 | 6.4 |
| 39A | 6.9 | 6.1 | 151 | 5.1 |
| 39B | 5.5 | < | 133 | |
| 41A | 5.4 | < | 100 | |
| 45A | 6.9 | 6.0 | 115 | |
| 45B | 5.4 | 6.0 | 153 | 5.6 |
| 46A | 6.1 | 5.9 | 92 | |
| 46B | < | 5.9 | 123 | |
| 47A | 6.3 | | 137 | |
| 47B | 6.0 | | 128 | 5.4 |
| 49 | < | < | 160 | 5.2 |
| 52A | 5.0 | < | 135 | 5.4 |
| 78 | 7.7 | 7.8 | 154 | 5.7 |
| 78A | 6.6 | 6.4 | 109 | 5.4 |
| 78B | 7.9 | 8.0 | 187 | 5.8 |
| 79 | 6.9 | 6.3 | 119 | 5.2 |
| 81A | 5.8 | < | 153 | 5.0 |
| 81B | 5.2 | < | 120 | 5.2 |
| 85 | | | 131 | 5.1 |
| 88 | | < | 110 | 5.1 |

<* denotes: <5.0 (inactive at $10^{-5}$ M)

From the data given in the table above it is evident that the compounds of the invention, that is, the compounds of general formula (I) combine a high affinity for nicotinic acetylcholine receptors, an affinity comparable with that of nicotine or cytosine, with activity as inhibitor of dopamine reuptake comparable to the standard dopamine reuptake inhibitors nomifensine and bupropion. This is in contrast with the compounds that are structurally very close: those disclosed in EP 1 178 045, which are inactive as dopamine reuptake inhibitors.

When comparing enantiomeric pairs (table above in combination with the table with structural data), it is evident that the (R)-enantiomers are more potent than the (S)-enantiomers.

Example 7

Pharmaceutical Preparations

For clinical use, compounds of formula (I) are formulated into a pharmaceutical compositions that are important and novel embodiments of the invention because they contain the compounds, more particularly specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein or apparent to a person skilled in the art from the specification and general knowledge in the art. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (I) in admixture with a pharmaceutically acceptable adjuvant, diluent and/or carrier. The total amount of active ingredients is in the range of from about 0.1% (w/w) to about 95% (w/w) of the formulation, for example, from 0.5% to 50% (w/w) or from 1% to 25% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin. Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating a condition in which activation of dopamine receptors and/or inhibition of dopamine uptake is required or desired, and methods of medical treatment or comprising the administration of a therapeutically effective total amount of at least one compound of formula (I) to a patient suffering from, or susceptible to, a condition in which activation of dopamine receptors and/or inhibition of dopamine uptake is required or desired.

REFERENCES

Bannon et al., *Science* 279: 77 (1998).
Bencherif and Schmitt, *Current Drug Targets*: CNS and Neurological Disorders, 1, 349-57 (2002).
Bickel, M. H., "*The pharmacology and Biochemistry of N-oxides*", *Pharmacological Reviews,* 21(4), 325-355 (1969).
Bioorganic & Medicinal Chemistry Letters, 12, 307-310 (2002).
Blum et al., *Pharmacogenetics* 5:121-141 (1995).
Breining et al., "*Neuronal nicotinic acetylcoline receptor modulators: recent advances and therapeutic potential*", Annual reports in medicinal chemistry, 40, 3-16 (2005).
Brioni et al., *Adv. Pharmacol.* 37, 153 (1997).
Bundgaard, H. (editor), "*Design of Prodrugs*", Elsevier (1985).
Chem. Pharm. Bull., 35, 1823-1828 (1987).
Coyle and Snyder, *Catecholamine uptake by synaptosomes in homogenates of rat brain; stereospecificity in different areas*, J. Pharmacol. Exp. Ther., 170, 221-231 (1969).
Current Organic Chemistry, 5, 471-506 (2001).
Damaj et al., *J. Pharmacol. Exp. Ther.* 291:390 (1999).

DeVries et al., "Heteroaromatic analogs of 1-[2-(diphenyl-methoxy)ethyl]- and 1-[2-[bis(4-fluorophenyl)metho-xy]ethyl]-4-(3-phenyl-propyl)piperazines (GBR 12935 and 12909) as High-Affinity Dopamine Reuptake Inhibitors", J. Med. Chem., 40, 705-716 (1997).
Dutta, K. et al., "Positional importance of the Nitrogen Atom in Novel Piperidine Analogs of GBR 12909: Affinity and Selectivity for the Dopamine Transporter", MED. CHEM. RES., 3, 209-222 (1993).
Ettmayer, P. et al., "Lessons learned from marketed and investigational prodrugs", J. Med. Chem., 47, 2393-2404 (2004).
European Journal of Medicinal Chemistry, 39, 515-526 (2004).
Greene, T. W. and P. G. M. Wuts, "Protective Groups in Organic Synthesis", third edition, John Wiley & Sons, Inc., New York (1999).
Helvetica Chimica Acta, 76, 2356-2366 (1993).
Heterocycles, 50, 1065-1080 (1999).
Heterocycles, 50, 1145-1150 (2000).
Järvinen, T. et al., "Design and Pharmaceutical applications of prodrugs", pages 733-796 in: S. C. Gad (editor): "Drug Discovery Handbook", John Wiley & Sons Inc., New Jersey, U.S.A. (2005).
J. Heterocyclic Chem., 21, 421, (1984)
J. Med. Chem., 45, 3972-3983 (2002).
King, F. D., (editor), page 215 in: "Medicinal Chemistry: Principles and Practice", ISBN 0-85186-494-5 (1994).
Levin and Rezvani, Current Drug Targets: CNS and Neurological Disorders 1, 423-431, (2002).
Onaivi et al., Life Sci. 54(3):193 (1994).
O'Neill, et al., Current Drug Targets: CNS and Neurological Disorders 1(4): 399-41 (2002).
Pabreza et al.: "[$^3$H]-Cytosine binding to nicotinic cholinergic receptors in brain", Mol. Pharmacol., 39, 9-12 (1991).
Perry and Kellar: "[$^3$H]-Epibatidine labels nicotinic receptors in rat brain: an autoradiographic study", J. Pharmacol. Exp. Ther., 275, 1030-1034 (1995).
Pullan et al., N. Engl. J. Med. 330, 811-815 (1994).
Sjak-shie et al., Brain Res. 624:295(1993).
Stella, J., "Prodrugs as therapeutics", Expert Opin. Ther. Patents, 14(3), 277-280 (2004).
Stoof et al., Brain Research 196: 276-28, (1980).
Synthesis, 7, 661-663, (1992).
Synthesis, 15, 2503-2506 (2005[1]).
Synthesis, 20, 3581-3588 (2005[2]).
Teng. et al., "Lobeline and nicotine evoke [$^3$H]-overflow from rat striatal slices preloaded with [$^3$H]dopamine: differential inhibition of synaptosomal and vesicular [$^3$H]dopamine uptake" J. Pharmacol. Exp. Therap., 80: 1432-1444 (1997).
Teng et al, "Lobeline displaces [$^3$H]dihydrotetrabenazine binding and releases$^3$H]dopamine from rat sriatal synaptic vesicles,"J. Neurochem., 71, 258-265 (1998).
Tetrahedron, 53, 3637-3648 (1997).
Tetrahedron, 58, 489-493 (2002).
Tetrahedron Asymmetry, 1, 885-894 (1990).
Tetrahedron Letters, 1909-1912 (1969).
Tetrahedron Letters, 38, 7511-7514 (1997).
Tetrahedron Letters, 40, 3673-3676 (1999).
Toth et al., Neurochem Res. 17, 265 (1992).
Cited Patents and Patent Applications
EP 0 870 768, EP 1 178 045.
U.S. Publication No. 2002/0061892, U.S. Publication No. 2003/0100547, U.S. Publication No. 2004/0266824.
WO 2003/053970, WO 2004/078757.

What is claimed is:

1. A method for preparing a pharmaceutical composition, the method comprising combining a compound of formula (I):

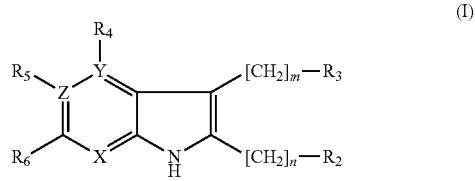

or a tautomer, stereoisomer, or N-oxide thereof, or a pharmacologically acceptable salt of any of the foregoing,
wherein
X is N, and Y and Z are C;
m is 0, and n is chosen from 0 and 1;
$R_2$ is chosen from a piperidinyl group, a pyrrolidinyl group, a tetrahydropyridinyl group, a morpholinyl group, a azepanyl group, a 1-aza-bicyclo[2.2.2]octanyl group, and a 1-aza-bicyclo[2.2.2]-oct-2-enyl group, which group is either unsubstituted or substituted with at least one substituent chosen from a halogen atom, a $(C_{1-3})$ alkyl group, a phenyl group and a benzyl group;
$R_3$ is hydrogen; and
$R_4$, $R_5$ and $R_6$, which are the same or different, are chosen from a hydrogen atom, a halogen atom, a $(C_{1-3})$alkyl group, a $(C_{2-3})$alkynyl group, a $CF_3$ group, a $NH(C_{1-3})$ alkyl group, a hydroxyl group and a $(C_{1-3})$alkyloxy group with the proviso that when X is N, Y and Z are C, m is 0, n is 1, $R_3$, $R_4$, $R_5$ and $R_6$ are H, $R_2$ is not a piperidinyl group, with
a pharmaceutically acceptable carrier and/or at least one pharmaceutically acceptable auxiliary substance.

2. A method for preparing a medicament, the method comprising combining a compound of formula (I):

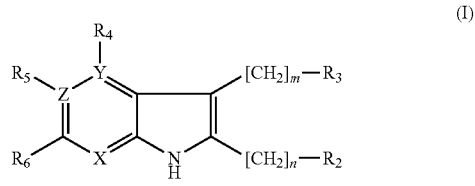

or a tautomer, stereoisomer, or N-oxide thereof, or a pharmacologically acceptable salt of any of the foregoing,
wherein
X is N, and Y and Z are C;
m is 0, and n is chosen from 0 and 1;
$R_2$ is chosen from a piperidinyl group, a pyrrolidinyl group, a tetrahydropyridinyl group, a morpholinyl group, a azepanyl group, a 1-aza-bicyclo[2.2.2]octanyl group, and a 1-aza-bicyclo[2.2.2]-oct-2-enyl group, which group is either unsubstituted or substituted with at least one substituent chosen from a halogen atom, a $(C_{1-3})$ alkyl group, a phenyl group and a benzyl group;
$R_3$ is hydrogen; and
$R_4$, $R_5$ and $R_6$, which are the same or different, are chosen from a hydrogen atom, a halogen atom, a $(C_{1-3})$alkyl group, a $(C_{2-3})$alkynyl group, a $CF_3$ group, a $NH(C_{1-3})$ alkyl group, a hydroxyl group and a $(C_{1-3})$alkyloxy group with the proviso that when X is N, Y and Z are C, m is 0, n is 1, $R_3$, $R_4$, $R_5$ and $R_6$ are H, $R_2$ is not a piperidinyl group, with a pharmaceutically acceptable carrier and/or at least one pharmaceutically acceptable auxiliary substance.

3. A method for preparation of a pharmaceutical composition for the treatment of at least one CNS disorder chosen from neuroendocrine, neurological and neuropsychiatric disorders, schizophrenia, memory and learning disabilities, attention deficit hyperactivity disorder, anxiety disorders, depressive disorders, neurodegenerative disorders, Alzheimer's disease, addiction disorders, nicotine addiction, cocaine addiction, amphetamine addiction, eating disorders pain, inflammatory processes, convulsive disorders, ocular disorders, glaucoma, macular degeneration, diabetic retinopathy, cardiovascular and gastrointestinal disorders and cancer, the method comprising combining a compound of formula (I):

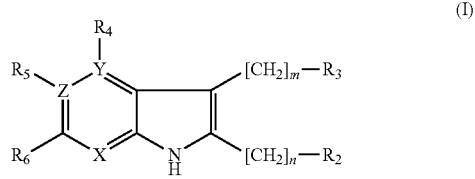

(I)

or a tautomer, stereoisomer, or N-oxide thereof, or a pharmacologically acceptable salt of any of the foregoing, wherein X is N, and Y and Z are C;

m is 0, and n is chosen from 0 and 1;

$R_2$ is chosen from a piperidinyl group, a pyrrolidinyl group, a tetrahydropyridinyl group, a morpholinyl group, a azepanyl group, a 1-aza-bicyclo[2.2.2]octanyl group, and a 1-aza-bicyclo[2.2.2]-oct-2-enyl group, which group is either unsubstituted or substituted with at least one substituent chosen from a halogen atom, a $(C_{1-3})$ alkyl group, a phenyl group and a benzyl group;

$R_3$ is hydrogen; and $R_4$, $R_5$ and $R_6$, which are the same or different, are chosen from a hydrogen atom, a halogen atom, a $(C_{1-3})$alkyl group, a $(C_{2-3})$alkynyl group, a $CF_3$ group, a $NH(C_{1-3})$ alkyl group, a hydroxyl group and a $(C_{1-3})$alkyloxy group with the proviso that when X is N, Y and Z are C, m is 0, n is 1, $R_3$, $R_4$, $R_5$ and $R_6$ are H, $R_2$ is not a piperidinyl group, with a pharmaceutically acceptable carrier and/or at least one pharmaceutically acceptable auxiliary substance.

4. A method for preparation of a pharmaceutical composition for the treatment of at least one addiction disorder chosen from nicotine addiction, cocaine addiction and amphetamine addiction, the method comprising combining a compound of formula (I):

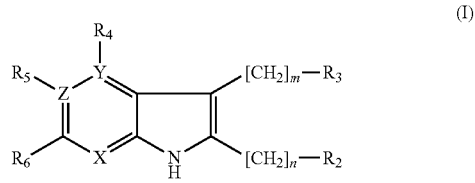

(I)

or a tautomer, stereoisomer, or N-oxide thereof, or a pharmacologically acceptable salt of any of the foregoing, wherein X is N, and Y and Z are C;

m is 0, and n is chosen from 0 and 1;

$R_2$ is chosen from a piperidinyl group, a pyrrolidinyl group, a tetrahydropyridinyl group, a morpholinyl group, a azepanyl group, a 1-aza-bicyclo[2.2.2]octanyl group, and a 1-aza-bicyclo[2.2.2]-oct -2-enyl group, which group is either unsubstituted or substituted with at least one substituent chosen from a halogen atom, a $(C_{1-3})$ alkyl group, a phenyl group and a benzyl group;

$R_3$ is hydrogen; and $R_4$, $R_5$ and $R_6$, which are the same or different, are chosen from a hydrogen atom, a halogen atom, a $(C_{1-3})$alkyl group, a $(C_{2-3})$alkynyl group, a $CF_3$ group, a $NH(C_{1-3})$ alkyl group, a hydroxyl group and a $(C_{1-3})$alkyloxy group with the proviso that when X is N, Y and Z are C, m is 0, n is 1, $R_3$, $R_4$, $R_5$ and $R_6$ are H, $R_2$ is not a piperidinyl group, with a pharmaceutically acceptable carrier and/or at least one pharmaceutically acceptable auxiliary substance.

* * * * *